(12) United States Patent
Bashkirov et al.

(10) Patent No.: US 11,034,998 B2
(45) Date of Patent: Jun. 15, 2021

(54) METHOD FOR LABEL-FREE SINGLE-MOLECULE DNA SEQUENCING AND DEVICE FOR IMPLEMENTING SAME

(71) Applicant: LIMITED LIABILITY COMPANY "GAMMA-DNA" [RU/RU], Moscow (RU)

(72) Inventors: Vladimir Ivanovich Bashkirov, Moscow (RU); Anton Vladimirovich Grigoriev, Saratov (RU); Mikhail Alexandrovich Gutorov, Moscow (RU); Eduard Anatolievich Ilichev, Moscow (RU); Vladimir Vladimirovich Kolesov, Moscow (RU); Konstantin Valerievich Krutovsky, Göttingen (DE); Alexey Olegovich Manturov, Saratov (RU)

(73) Assignee: LIMITED LIABILITY COMPANY "GAMMA-DNA", Moscow (RU)

( * ) Notice: Subject to any disclaimer, the term of this patent is extended or adjusted under 35 U.S.C. 154(b) by 0 days.

(21) Appl. No.: 16/484,461

(22) PCT Filed: Mar. 29, 2018

(86) PCT No.: PCT/RU2018/000202
§ 371 (c)(1),
(2) Date: Aug. 8, 2019

(87) PCT Pub. No.: WO2019/132713
PCT Pub. Date: Apr. 7, 2019

(65) Prior Publication Data
US 2019/0360039 A1    Nov. 28, 2019

(30) Foreign Application Priority Data

Dec. 26, 2017  (RU) .......................... RU2017135756

(51) Int. Cl.
C12Q 1/6869   (2018.01)
B01L 3/00     (2006.01)
B01L 7/00     (2006.01)

(52) U.S. Cl.
CPC ...... *C12Q 1/6869* (2013.01); *B01L 3/502715* (2013.01); *B01L 7/52* (2013.01);
(Continued)

(58) Field of Classification Search
None
See application file for complete search history.

(56) References Cited

U.S. PATENT DOCUMENTS 6,770,472 B2   8/2004  Manalis
7,556,922 B2   7/2009  Block et al.
(Continued)

FOREIGN PATENT DOCUMENTS

RU   2539038 C1   1/2015
RU   2685953 C1   4/2019

OTHER PUBLICATIONS

English Translation of RU 2539038 C1 [online] Jan. 10, 2015 [retrieved on Jan. 20, 2020] retrieved from https://patents.google.com/patent/RU2539038C1/en. (Year: 2015).*
(Continued)

*Primary Examiner* — Samuel C Woolwine
(74) *Attorney, Agent, or Firm* — Dmitry S. Kryndushkin

(57) ABSTRACT

A method and a device for determining a nucleotide sequence are proposed. The method comprises immobilising looped fragments of a nucleic acid and a polymerase on a sensor surface and adding a mixture of unlabelled nucleotides onto the sensor surface. Moreover, in the mixture added, one nucleotide type is present at a much lower concentration compared to the other nucleotides. Time intervals between each of the charge separation events are
(Continued)

determined and the mixture addition and the registration steps are repeated. Moreover, at each repetition, the nucleotide type present at a much lower concentration compared to the other nucleotides in the mixture added is changed. The nucleotide sequence of a nucleic acid molecule is determined by the analysis of the time intervals between each of the charge separation events registered, which result from the insertion, facilitated by the polymerase, of said unlabelled nucleotides into the growing nucleic acid chain. The device comprises a matrix having a plurality of sensor cells, and a digital-analog circuit, a microfluidic apparatus for feeding working solutions to the sensors, and data processing and display means.

17 Claims, 26 Drawing Sheets

Specification includes a Sequence Listing.

(52) U.S. Cl.
CPC ... *B01L 2200/027* (2013.01); *B01L 2200/147* (2013.01); *B01L 2300/023* (2013.01); *B01L 2300/027* (2013.01); *B01L 2300/0627* (2013.01); *B01L 2300/18* (2013.01)

(56) References Cited

U.S. PATENT DOCUMENTS

| | | |
|---|---|---|
| 10,036,064 B2 | 7/2018 | Merriman et al. |
| 2011/0183320 A1* | 7/2011 | Flusberg .............. C12Q 1/6869 435/6.1 |
| 2013/0078622 A1* | 3/2013 | Collins ................. G01N 27/26 435/6.1 |
| 2015/0065353 A1 | 3/2015 | Turner et al. |
| 2017/0038333 A1 | 2/2017 | Turner et al. |
| 2018/0155773 A1* | 6/2018 | Gunderson .......... C12Q 1/6869 |
| 2018/0305727 A1 | 10/2018 | Merriman et al. |
| 2019/0004003 A1 | 1/2019 | Merriman et al. |
| 2019/0039065 A1 | 2/2019 | Choi et al. |
| 2019/0041355 A1 | 2/2019 | Merriman et al. |

OTHER PUBLICATIONS

Veigas et al. Field Effect Sensors for Nucleic Acid Detection: Recent Advances and Future Perspectives. Sensors 15:10380-10398. (Year: 2015).*

Pourmand et al. Direct electrical detection of DNA synthesis. PNAS 103(17):6466-6470. (Year: 2006).*

Lee et al. Aptamers as molecular recognition elements for electrical nanobiosensors. Anal. Bioanal. Chem. 390:1023-1032. (Year: 2008).*

Poghossian et al. Label-free sensing of biomolecules with field-effect devices for clinical applications. Electroanalysis 26:1197-1213. (Year: 2014).*

Takahashi et al. Preparation of Phi29 DNA polymerase free of amplifiable DNA using ethidium monoazide, an ultraviolet-free light-emmitting diode lamp and trehalose. PLoS ONE 9(2):e82624 (9 pages). (Year: 2014).*

Erickson, H. Size and shape of protein molecules at the nanometer level determined by sedimentation, gel filtration, and electron microscopy, in: Biological Procedures Online, vol. 11, No. 1, pp. 32-51. (Year: 2009).*

Maekawa et al. "Effect of double-stranded DNA on electrical double layer structure atoxide/electrolyte interface in classical molecular dynamics simulation" Chemical Physics Letters, 2014,619 (2015) 152-157.

* cited by examiner

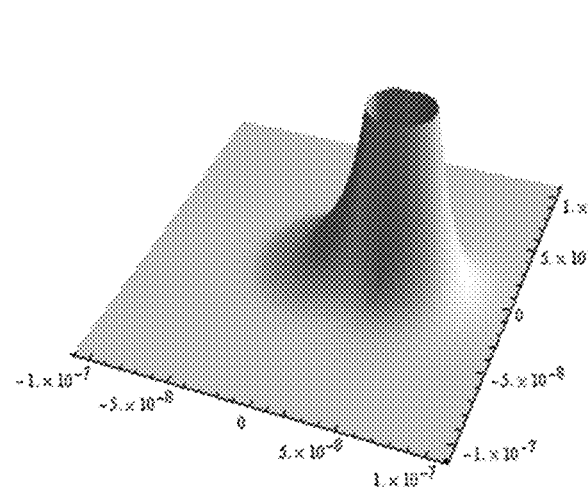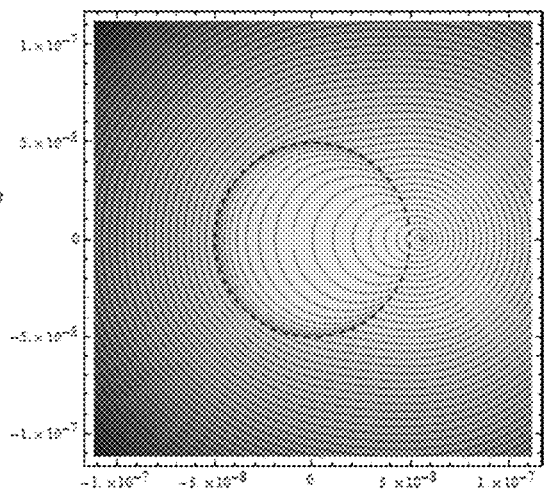
Fig. 17A.                               Fig. 17B.
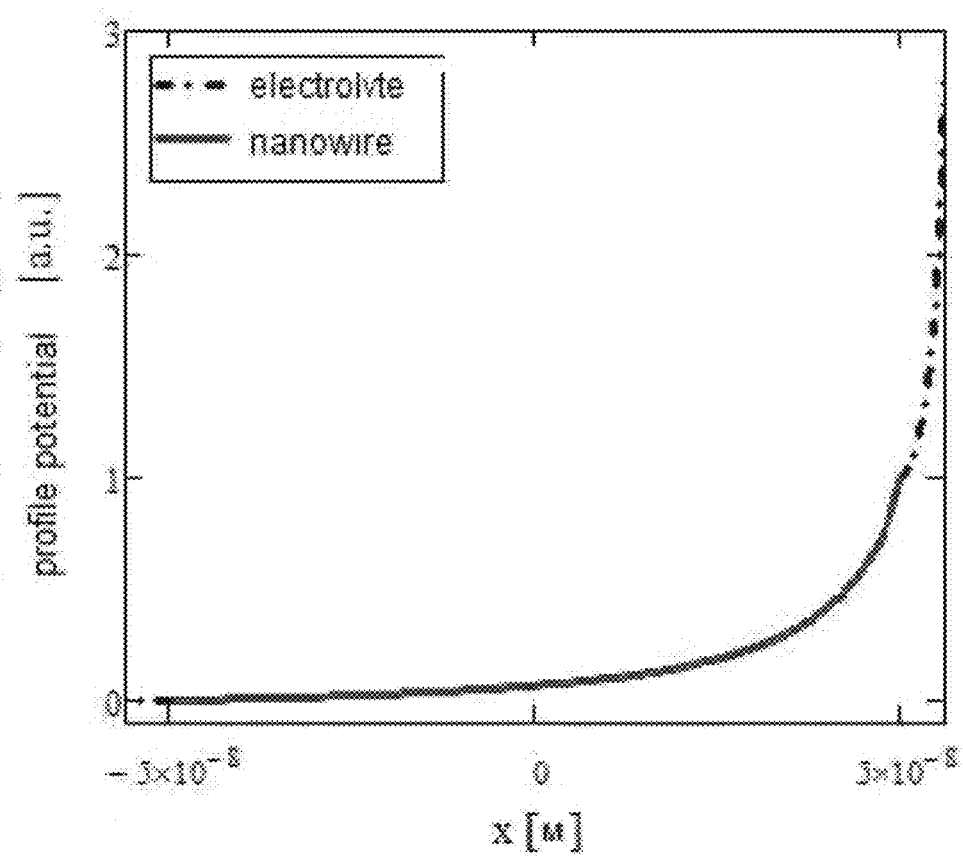
Fig. 18.

SEQUENCE LISTING

```
<160> NUMBER OF SEQ ID NOS: 5

<210> SEQ ID NO 1
<211> LENGTH: 177
<212> TYPE: DNA
<213> ORGANISM: Artificial Sequence
<220> FEATURE:
<223> OTHER INFORMATION: ultramer-oligonucleotide used for obtaining a
      single-stranded circular DNA

<400> SEQUENCE: 1
catgtagtgt acgatccgac tttacttcag cgtccgtcgc aaggaaatct agccgtcgag      60
gcgctattgg agactagctg acaccaccgt gccaactgaa gaagggcagc tatgcgtcct    120
gttgacaatt atctttaact cgtttattgg ttagtcaagg tccaagcctg ctatgga       177

<210> SEQ ID NO 2
<211> LENGTH: 22
<212> TYPE: DNA
<213> ORGANISM: Artificial Sequence
<220> FEATURE:
<223> OTHER INFORMATION: Direct PCR primer

<400> SEQUENCE: 2
catgtagtgt acgatccgac tt                                              22

<210> SEQ ID NO 3
<211> LENGTH: 20
<212> TYPE: DNA
<213> ORGANISM: Artificial Sequence
```

-continued

```
<220> FEATURE:
<223> OTHER INFORMATION: Reverse PCR primer

<400> SEQUENCE: 3
tccatagcag gcttggacct                                               20

<210> SEQ ID NO 4
<211> LENGTH: 27
<212> TYPE: DNA
<213> ORGANISM: Artificial Sequence
<220> FEATURE:
<223> OTHER INFORMATION: Oligonucleotide-bridge

<400> SEQUENCE: 4
gtacactaca tgtccatagc aggcttg                                       27

<210> SEQ ID NO 5
<211> LENGTH: 23
<212> TYPE: DNA
<213> ORGANISM: Artificial Sequence
<220> FEATURE:
<223> OTHER INFORMATION: an example of a DNA sequence for a method
      embodiment

<400> SEQUENCE: 5
aacgtcttca gggctagcac cat                                           23
```

METHOD FOR LABEL-FREE SINGLE-MOLECULE DNA SEQUENCING AND DEVICE FOR IMPLEMENTING SAME

SEQUENCE LISTING

The instant application contains a Sequence Listing which has been filed electronically under name "Sequence_listing" on Aug. 8, 2019 in ASCII format and contains 2 kB.

TECHNICAL FIELD

The group of inventions is related to the field of technology of determination of nucleotide sequence of DNA and RNA, or sequencing of nucleic acids. The disclosed invention may find application in genetic diagnostics of various humans and animal diseases, as well as in other areas of applied and fundamental science.

BACKGROUND

New methods of highly efficient sequencing of nucleic acids have been developed during last two decades, and some of them are currently widely used in medicine, agriculture, human identification and security, food industry and biotechnology. These techniques fall into three major groups of technologies: (1) sequencing by ligation methods (e.g. SOLiD sequencing of Life Technologies/Thermo Fisher, and Combinatorial Probe-Anchor Ligation™ (cPAL™) method used by BGI/Complete Genomics); (2) sequencing by synthesis methods, comprising: (a) cyclic sequencing used by Illumina Inc. and Qiagen Inc., (b) real-time single-molecule virtual terminator method developed by Helicos BioSciences, (c) method of sequential incorporation of single nucleotide, which includes 454 pyrosequencing by Roche Inc., and a method based on ion-sensitive field transistor with an electronic readout developed by Ion Torrent/Thermo Fisher; (3) real-time single-molecule sequencing methods capable of reading long continuous nucleic acid sequences (long reads) from one reaction: (a) single-molecule sequencing in real-time (SMRT) by Pacific Biosciences, based on fluorophore-labeled nucleotide detection and identification in waveguides smaller than the wavelength (ZMW), and (b) label-free sequencing method that uses an electronic means of reading the signals when threading the nucleic acid (DNA) fragment through the nanopore used by Oxford Nanopore Technologies. The first (1) and second (2) group of technologies mentioned above are collectively called the Second-Generation Sequencing (SGS) technologies, while the third (3) group—Third Generation Sequencing (TGS) technologies.

Ligation-based sequencing methods (SOLiD and cPAL) use expensive fluorophore-labeled probes, and their sequencing speed, as well as the read length, are limited by the intrinsic properties of DNA-ligases. Sequencing by synthesis methods from Illumina and Qiagen are way faster in comparison with the ligation methods and can generate reads up to 300 base pairs (bp), but are still dependent on expensive fluorescently-labeled terminator nucleotides. Currently the semiconductor sequencing from Ion Torrent/Fisher Scientific is the only commercially available label-free sequencing method, but it still relies on cycles of addition of single nucleotides, unlike the single-molecule real-time sequencing (SMRT-method) driven by highly productive DNA-polymerase. The latter method is the only commercially available fast sequencing method producing long reads in real-time. The disadvantages of SMRT method are the use of fluorophore-labeled nucleotides, cumbersome expensive optics, high error rate, sensitivity to carryover of impurities, and lower throughput compared to, for example, the methods of Illumina, SOLiD, Ion Torrent/Thermo Fisher, and BGI/Complete Genomics. These disadvantages of SMRT method result in high instrument and sequencing cost.

SGS sequencing platforms, except the method of virtual terminators from Helicos Biosciences, operates by sequencing of clusters (ensembles of clonally amplified by DNA polymerase DNA molecules), whereas TGS technologies directly determines the nucleotide sequence of the individual molecules. In addition, the SGS platforms use methods of "flushing and scanning" (e.g. Illumina), or "flushing and measurement" of the electric signal (Ion Torrent), while TGS platforms represents streamline technologies without having to stop between the reading steps. TGS sequencing is very fast, and the speed is determined by the rate of synthesis by polymerase, or by the speed of the DNA translocation through the nanopore. Furthermore, TGS technologies do not require the pre-amplification of DNA (during library preparation or cluster generation), thereby simplifying the complexity associated with amplification (such as error occurrence, and discrimination against DNA library fragments with the high GC and/or AT content). Long continuous sequences of nucleic acids obtained by TGS methods (long reads), significantly help in genome phasing, and, thereby, reduce the need for additional methods for genome assembly.

Despite the fact that TGS technologies provide short cycle time of data processing, their major competitive drawbacks compared to SGS are the high error rate, a lower data yield from single sequencing cell and the high cost per sequenced molecule. To expand the biomedical applications of TGS technologies it is necessary to minimize the number of errors, increase sequencing throughput, and reduce the cost. The present disclosure provides methods, devices and compositions for low cost, high performance label-free single-molecule real-time sequencing with an electronic readout. These methods represent a novel technology of nucleic acid sequencing and can be used in variety of biomedical, agricultural and biological applications.

Definitions and Terms

For a better understanding of the present invention the terms and definitions used in disclosure of the invention are listed below.

In the description of this invention the words "comprises" and "comprising" are interpreted to mean "includes, among other things". These words hereafter, except where otherwise indicated, are not intended to be construed as "consists of only".

Under nucleotide in the description of the invention is to be understood, depending on the embodiment, as ribonucleotides, e.g. adenosine triphosphate, guanosine triphosphate, cytidine triphosphate, and uridine triphosphate (denoted ATP, GTP, CTP, UTP), and deoxyribonucleotides, such as deoxyadenosine triphosphate, deoxyguanosine triphosphate, deoxycytidine triphosphate, and deoxythymidine triphosphate (dATP, dGTP, dCTP, dTTP). In preferred embodiments, the nucleotides are used that do not contain labels and modifications.

Under the reaction mixture is meant an aqueous solution containing all the necessary materials to ensure that the polymerization reaction, single-stranded DNA fragments are in the "fragment DNA-polymerase" complex immobilized on the on the surface of the sensor of the cell of the microchip array.

Under the charge separation that occurs as a result of the nucleotide incorporation by the polymerase into the growing nucleic acid chain, it will be understood the separation of a pair of charges (electron attachment to the growing chain of nucleic acid, and release of hydrogen ion in the solution), which objectively occurs whenever there is incorporation of a nucleotide into a polymerizable DNA or RNA fragment Sensor called electronic device, one or more electrical characteristics of which are modulated by the formation of one pair of unbound charges occurring in the vicinity of the sensor surface, as a result of the incorporation of a nucleotide by the polymerase into a polymerizable DNA fragment.

Cell is called an electronic device including a sensor and an analog-digital circuit, which in each discrete time interval converts the modulating characteristics of the sensor to a logical "0" or "1" depending on its magnitude.

The array of the cells of sensors is an ordered plurality of cells, arranged in rows and columns, typically in the form of a square or rectangle having vertical and horizontal shift registers providing the output of digital data from each cell of the array of its border, for subsequent, for example, computer processing.

The microcircuit of the array of sensor cells is the collection of the array of the sensor cells and the analog-to-digital circuit including a clock generator, a reference voltage source, the controller of operating modes of the cells, which provides the functionality of cells and registers of the array are manufactured in one technological cycle or in several technological cycles.

The bias electrode is called the metallic conductor of one form or another, e.g. in the form of a grid, and fixed one way or another on the lid of integrated circuit (made of non-conductive material), in the operating condition is in the working solution, galvanically connected to a source of the reference voltage of the microcircuit, providing the voltage bias to the electrode of each cell of the array in the presence the electric field in solution, which facilitates the rapid removal of hydrogen ion from the space in which a pair of charges is splitting up during the incorporation of the nucleotide into the polymerizable DNA fragment.

Cyclogramm herein called a sequence of the discrete time intervals, wherein a logical unit of "1" denotes those discrete intervals of time, during which the analog-to-digital circuit of the cell registers the events of the charge separation during nucleotide incorporation by polymerase, and logic zeros "0" denote the discrete time intervals, when no such events have been recorded. A discrete time interval called the period of clock pulses that provide the functioning of analog-to-digital cell circuit.

Processivity—the ability of the enzyme to carry out a sequence of chemical reactions without releasing the substrate. In case of the polymerase the processivity is the average number of nucleotides added to the growing chain by the enzyme per single event of binding to the array surface.

If not specified separately, technical and scientific terms herein have the standard meanings generally accepted in the scientific and technical literature.

SUMMARY OF THE INVENTION

The objective of the present invention is to provide a rapid, highly accurate, and inexpensive method for determining the nucleotide sequence, or sequencing of nucleic acids. In the present invention this objective is achieved by implementing several technical solutions. Three basic positions are implemented together, allowing to provide technical result: (1) a minimum of manipulation with DNA and reagents that participate in biochemical reactions; (2) the registration by an electronic sensor of the useful signal resulting from events of separation of one pair of the charges that occur as a result of incorporation of each nucleotide by DNA polymerase into a growing DNA strand; (3) unique sequencing algorithm which allows to separate in time the procedure of forming the useful signals and the target information forming process, as a result of processing of useful signals,—that eliminates the need for labeled nucleotides.

The objective is achieved by providing a method for determining the nucleotide sequence of a nucleic acid molecule comprising at least the following steps:

(a) obtaining a nucleic acid sample comprising a plurality of circularized nucleic acid fragments; (b) immobilization of complexes comprising at least the said circularized nucleic acid fragments and the polymerase, having an affinity for nucleic acid, on the solid support, wherein the solid support is the sensor surface, and immobilization retains the functionality of the polymerase and ensures that the polymerase is near a sensor surface within the entire process of determining the nucleotide sequence; (c) providing conditions for the functional activity of said polymerase, consisting in catalyzing the nucleotide addition to the growing nucleic acid strand, wherein the conditions for functional activity of said polymerase include: the addition to the sensor surface of the mixture of two or more kinds of unlabeled deoxyribonucleotides selected from the group consisting of deoxyadenosine triphosphate, deoxyguanosine triphosphate, deoxycytidine triphosphate, and deoxythymidine triphosphate, or addition on the sensor surface of the mixture of two or more kinds of unlabeled ribonucleotides selected from the group consisting of adenosine triphosphate, guanosine triphosphate, cytidine triphosphate, and uridine triphosphate, wherein one kind of triphosphates in said mixture is present in much lower concentrations than other types of nucleotides; (d) registration by the sensor of the charge separation event that occurs as a result of incorporation by polymerase of nucleotide into a growing nucleic acid chain, and determining the time intervals between each successive recorded event of charge separation; (e) at least one time repeating steps (c) and (d) wherein at each repetition the type of nucleotide present in the added nucleotide mix in much smaller concentration, as compared with other kinds of nucleotides, is changed; (f) determining the nucleotide sequence of said nucleic acid molecules based on an analysis of the time intervals between each registered event of charge separation determined at steps (d) and (e), where charge separation occurred as a result of embedding by polymerase of said unlabeled nucleotides into the growing strand of the nucleic acid.

Some embodiments of the invention include a method as described above, wherein the circularized fragments of nucleic acid of step (a) share at least one single-stranded region (see FIGS. 1A and 1B); the complexes of steps (b) and (c) further include the sequencing primer having a nucleotide sequence complementary to said single-stranded portion; and conditions for the functional activity of the polymerase further include conditions ensuring the formation of duplex between sequencing primer and said complementary single-stranded portion of the circularized nucleic acid fragment (see FIGS. 1A and 1B).

In some embodiments of the invention, said circularized fragments of step (a) do not have single stranded regions capable of forming a duplex with sequencing primers (see FIG. 1C), so that said complexes of steps (b) and (c) do not include a sequencing primer (see FIG. 1C); and the synthesis of DNA is initiated by polymerase from the artificially created free 3' end in one of the strands of double-stranded circularized fragment.

Some embodiments of the invention include the above-described method in which the nucleic acid is the deoxyribonucleic acid (DNA); the polymerase having an affinity for nucleic acid is a DNA polymerase and the nucleotide triphosphates added in steps (c) and (e) are deoxyadenosine triphosphate, deoxyguanosine triphosphate, deoxycytidine triphosphate, and deoxythymidine triphosphate. DNA polymerase suitable for carrying out the said method comprises at least the following enzymes: phage Phi29 DNA polymerase, large fragment of Bst DNA polymerase, VentR polymerase, large fragment of Bsm DNA polymerase, and Klenow fragment of DNA polymerase I. Other embodiments of the invention include a method as described above, wherein the polymerase having affinity for nucleic acid is an RNA polymerase; and the nucleotide triphosphates added in steps (c) and (e) are adenosine triphosphate, guanosine triphosphate, cytidine triphosphate, and uridine triphosphate.

In certain preferred embodiments of the described above method, there is provision of four different conditions for the functional activity of the polymerase at steps (c) and (e), namely, the addition of four different deoxyribonucleotide triphosphates mixtures on the sensor surface, wherein each of the four different conditions for the functional activity of the polymerase is present continuously for a time interval sufficient for the synthesis of at least one copy of a circularized DNA fragment, or at least five copies of circularized DNA fragment. In this case, analysis of the sequential time intervals used to determine the nucleotide sequence of said nucleic acid molecule comprises at least three steps:

1) obtained sequence of time intervals between each registered events of the charge splitting resulting from the incorporation of unlabeled nucleotides in the nascent nucleic acid chain is converted into the sequence of logical Ones and Zeroes, wherein Ones represent the events of the incorporation of nucleotides of the kind, the concentration of which was known and lowered in the reaction mixture corresponding to obtained sequence of time intervals, and wherein logical Zeroes represents the types of nucleotides the concentration of which was normal in the same reaction mixture used;

2) reconstituting the nucleotide sequences of the nucleic acid fragments from the four sequences consisting of Ones and Zeroes, which were obtained after the first stage of dataconversion for each nucleic acid fragment;

3) the nucleotide sequences of nucleic acid fragments are converted into defined nucleotide sequence of said nucleic acid molecule.

In other preferred embodiments of the described above method, the four different conditions for the polymerase functional activity at steps (c) and (e) are provided simultaneously, and include: (i) the presence of four spatially separated arrays of cells containing said sensors; and (II) parallel addition of four different deoxy triphosphates mixtures on the surface of the sensors residing in four spatially separated arrays of sensors. In this case, analysis of the sequences of time intervals used to determine the nucleotide sequence of said nucleic acid molecule comprises at least four steps:

1) the sequences of time intervals obtained from the sensor cells of four arrays, as a result of registration of the events of charge splitting during the incorporation of unlabeled nucleotides in the nascent chain of nucleic acid, are converted to form the sequences of logical Ones and Zeroes, wherein Ones designated the events of the incorporation of nucleotides, the concentration of which was known and lowered in the reaction mixture, and wherein Zeroes denote the kinds of nucleotides whose concentration was normal in the same reaction mixture present on the surface of the array, whose sensor cells served as a source for the output sequence;

2) the number of sequences of logical Ones and Zeroes is reduced to the number of fragments obtained after fragmentation of the input nucleic acid through the operations of sorting, comparing, selecting, and averaging the same (with certain probability) sequences of logical Ones and Zeroes obtained from the clones of one and the same fragment immobilized as a part of complexes on the surface of the sensor cells of the same array into a single sequence (series) of logical Ones and Zeroes, 3) forming (reconstituting) a nucleotide sequences of nucleic acid fragments derived from the four obtained logical sequences of Ones and Zeroes, 4) converting the nucleotide sequences of nucleic acid fragments into defined nucleotide sequence of said nucleic acid molecule.

The objective of the invention is also achieved by providing an apparatus implementing one or another embodiment of the above described method of single molecule label-free nucleic acid sequencing. An apparatus for determining the nucleotide sequence of a nucleic acid molecule comprising: 1) at least one microcircuit of array of sensor cells comprising an array with a plurality of sensor cells and analog-to-digital; 2) microfluidic device for providing a supply of working solution to the sensor cells of array of microcircuit; 3) data processing and display device to control operating modes of the microfluidic device and the microcircuit of the array of sensor cells to convert the output data from the cells of array into the nucleotide sequence of said nucleic acid molecule. In certain preferred embodiments, the apparatus is characterized in that: 1) each cell of the array comprises: a sensor with the surface which is suitable for immobilization of polymerase complex registering the events of separation of one pair of charge in an aqueous solution resulting from incorporation by polymerase of each nucleotide into nascent strand synthesized within the complex, and generating signals corresponding to a registered events of charge separation; 2) an analog-digital integrated circuit of the array of sensor cells comprising: circuitry forming currents, voltages and clock frequencies required for operation of the analog-digital circuits of the cells of an array; circuitry for transmission of output sequences from the cells of an array to data processing and display device; circuitry of a data decoding received from the data processing and display device.

The solid surface that is suitable for polymerase complex immobilization comprises the surface of the sensor, chemically modified to immobilize the polymerase complex. Functional variants of the surface modification of the sensor will be discussed below. The analog-digital circuit of the microcircuit of the array of sensor cells is configured to generate currents, voltage biases and clock rates required for the operation of analog-digital circuit of sensor cells, control of the transmission of output sequences from sensor cells to data processing and display unit. The apparatus also comprises the microfluidic device for providing a supply of working solutions to the sensor cells of the array; the device to manage the microfluidic device, the device to manage the microcircuit of array of sensor cells, the device to transfer of output data from integrated circuit to data processing and display unit, and the module of data processing and displaying for control of operating mode of microfluidic unit, integrated circuits of array of sensor cells, and for conversion of the output data from the cells of the array into the nucleotide sequence of nucleic acid molecule.

Some embodiments of the invention imply that each discrete time interval in the output sequence has designated logical Zero or One, wherein the time interval, which was recorded as the event of separation of the pair of charges by the sensor cell, is designated by logical One.

In some embodiments, the apparatus further includes the temperature control device maintaining the temperature of the working solution above the surface of microcircuit array, which is controlled by the data processing and display device.

In various embodiments, the sensor may be implemented as a nanowire field transistor, a single electron transistor, a diode, FET, or the semiconductor structure (electronic circuit) with S-shaped or N-shaped voltage-current characteristics or response characteristics.

Some embodiments of the invention include serial sequencing method, wherein the sequencing device comprises only one array of sensor cells, and reaction mixtures are fed alternately onto the surface of the array. Wherein the data processing and display device converts the data output sequences from array of sensor cells into the nucleotide sequence of a nucleic acid molecule in three successive stages.

At the first stage, the data output sequences obtained from cells of the microcircuit of the array of sensor cells sequentially converted to form sequences of logical zeros and ones, wherein a logic Ones represent of nucleotides of the type whose concentration was known and was reduced in the corresponding reaction mixture, and the logical zeros indicate the type of nucleotides, the concentration of which was normal in the same reaction mixture; at the second stage the nucleotide sequence of the nucleic acid fragments are formed of the four of logical zeros and ones obtained after the first stage of data conversion from the same cell of the microcircuit of the array of sensor cells; at a third stage the nucleotide sequences of nucleic acid fragments can be converted to the nucleotide sequences of nucleic acids.

Some embodiments of the invention include a method for parallel sequencing wherein sequencing apparatus comprising four arrays of sensor cells, and the reaction mixtures are fed simultaneously, asynchronously to the surface of each array. Wherein the processing and display device converts the data output sequences obtained from all the cells of all arrays into the nucleotide sequence of a nucleic acid molecule in four successive stages.

At the first stage, the data output sequences obtained from cells of arrays of four microchips are converted to form sequences of logical zeros and ones, and a logic Ones designate the type of nucleotides, the concentration of which was known and lowered into the reaction mixture, and logical zeros denote the type of nucleotides, whose concentration was normal in the same reaction mixture over the surface of that microchip, from the cells of which the output sequences are converted; at the second stage, the number of sequences of logic ones and zeroes is reduced to the number of fragments obtained after fragmentation of the input nucleic acid through the operations of sorting, comparing, selecting and averaging the same (with a certain probability) sequences of logical zeros and ones obtained from clones of the same one fragment immobilized within the complexes on the surface of a sensors of cells of microchip array, —into a single sequence of logical ones and zeros; in the third stage the nucleotide sequence of the nucleic acid fragments are formed of the four sequences of logical zeros and ones, taken one from each of the four microchips; in a fourth stage the nucleotide sequences of nucleic acid fragments can be converted to the nucleotide sequences of nucleic acids.

Some embodiments include a combined method of sequencing wherein sequencing apparatus comprises two or three arrays of sensor cells, and a part of the reaction mixtures are delivered simultaneously, asynchronously to the surface of each microchip, and the remainder of the reaction mixtures are delivered successively with originally delivered part of the reaction mixtures.

In preferred embodiments, the reaction mixtures used a reduced concentration of nucleotides of one type, compared to the normal concentration of three other types of nucleotides in the reaction mixture (the essence of the sequencing method does not change if the reaction mixture contains nucleotides of one type, the concentration of which is normal and nucleotides of three other types whose concentration are reduced, or if the reaction mixture contains nucleotides of one type, whose concentration is raised and the other three types of nucleotides, whose concentration is normal, etc.).

In preferred embodiments, for purposes of medical diagnosis the serial sequencing method is used, as it does not require amplification of input nucleic acid.

In carrying out the invention, the following technical results are achieved:

the proposed apparatus of single-molecule label-free sequencing provides an improved accuracy of sequencing of nucleic acids as compared to existing sequencing instruments due to multiple polymerization of the circularized DNA fragment in the same reaction mixture, which allows averaging of the duration of time intervals prior to insertion of each nucleotide in the circularized DNA fragment of the complex and increases the probability of correct identification of the locations on the DNA fragment of the type of nucleotide whose concentration is reduced in this reaction mixture;

the proposed apparatus of single-molecule label-free sequencing provides improved performance due to the possibility to use the method of sequencing by synthesis (SBS) at the maximum possible rate of polymerization of a DNA fragment (e.g. human genome resequencing in less than 12 hours);

the proposed apparatus of single-molecule label-free sequencing provides a lower cost of the device and the result of sequencing as compared with other sequencing devices (less than $1,000 per re-sequenced human genome) due to the absence of expensive tags for nucleotides, low reagent consumption, low cost of the microchip of array of sensor cells fabricated by industrial based semiconductor technology.

BRIEF DESCRIPTION OF THE DRAWINGS

The accompanying drawings, which are incorporated in the present specification and form a part hereof, illustrate embodiments of the invention and, together with the above general description of the invention and the following detailed description of the embodiments serve the purpose to explain the principles of the present invention.

FIG. 1 is a schematic view of embodiments of circularized DNA fragments and corresponding complexes formed by these fragments with a polymerase.

Figure 13:
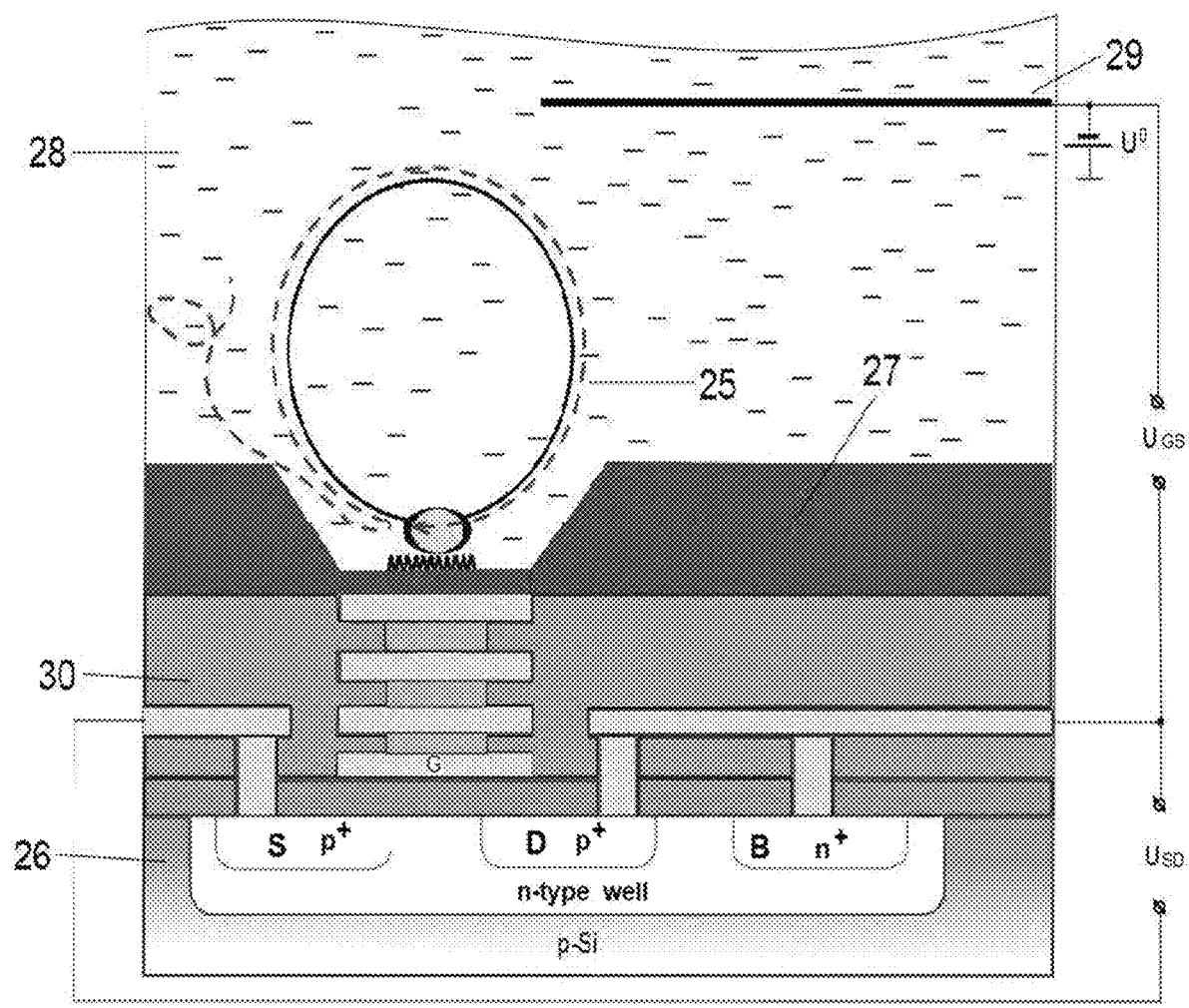

FIG. 13 is a structural diagram of a sensor cell of the array manufactured by standard CMOS technology, with the ternary complex immobilized on its surface. Complex "polymerase-primer DNA fragment" immobilized on the sensor surface, designated as 25, the substrate of p-type silicon in which the sensor is manufactured, an analog-digital cell circuit, an array of cells, the analog-digital circuit of microchip, etc. denoted by the number 26, the number 30 denotes the dielectric insulating layers (e.g., silicon dioxide, SiO2), the number 28 denotes an aqueous solution of the reaction mixture, providing the reaction conditions for polymerization of the DNA fragment, the number 29 denotes the bias electrode, an insulating passivation layer 27 isolates the entire surface of the cell except the sensor surface from the solution.

Figure 14:
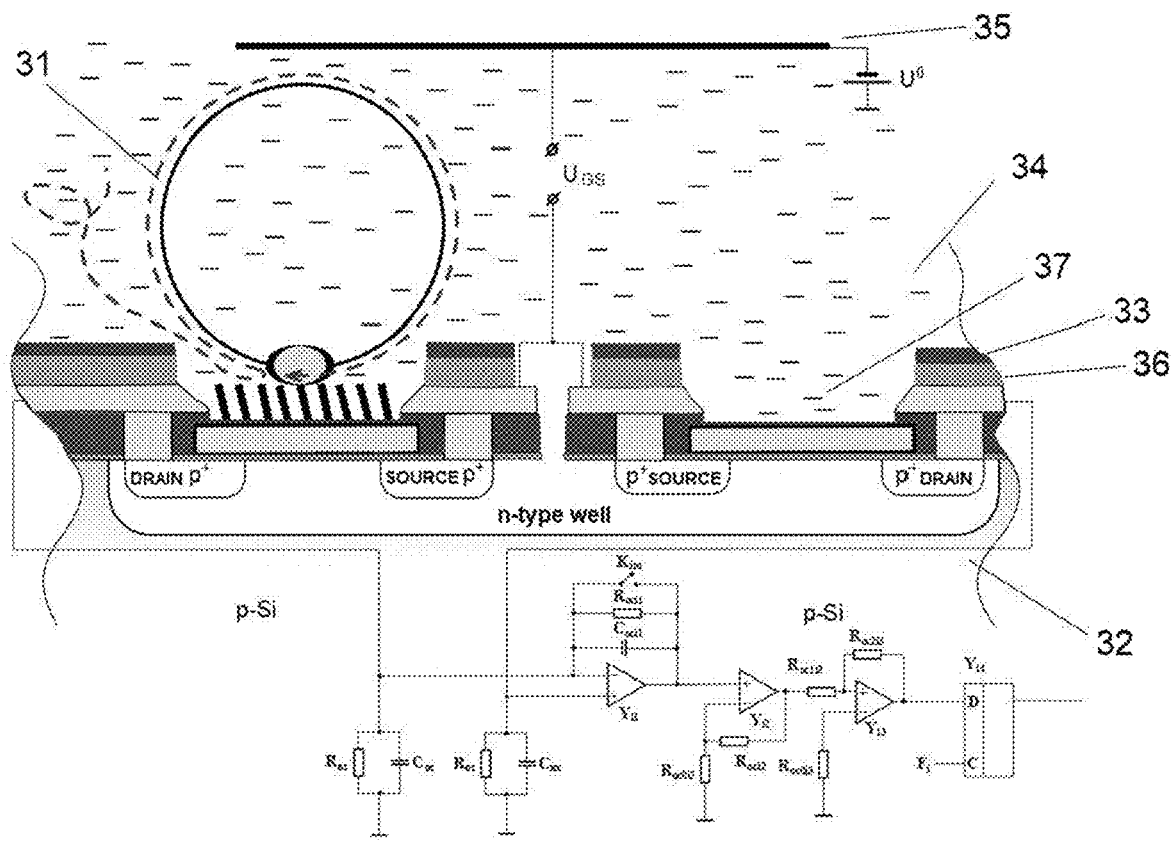

FIG. 14 is a block diagram of two sensors of the cell of an array: with a ternary polymerase complex immobilized on a passivated sensor surface 31, and with the sensor surface 37, protected from specific binding to the complex, and an analog-digital cell circuit. The number 32 is a substrate of p-type silicon, in which the sensor is made, an analog-digital cell circuit, the array of cells, analog-to-digital circuit of microchip, etc., the number 36 denotes layers of insulating dielectric (e.g., silicon dioxide $SiO_2$), number 34 denotes an aqueous solution of the reaction mixture, providing the reaction conditions for polymerization of the DNA fragment, the number 35 denotes the bias electrode; an insulating passivation layer 33 isolates the entire surface of the cell except the two sensor surfaces from the solution.

Figure 15:
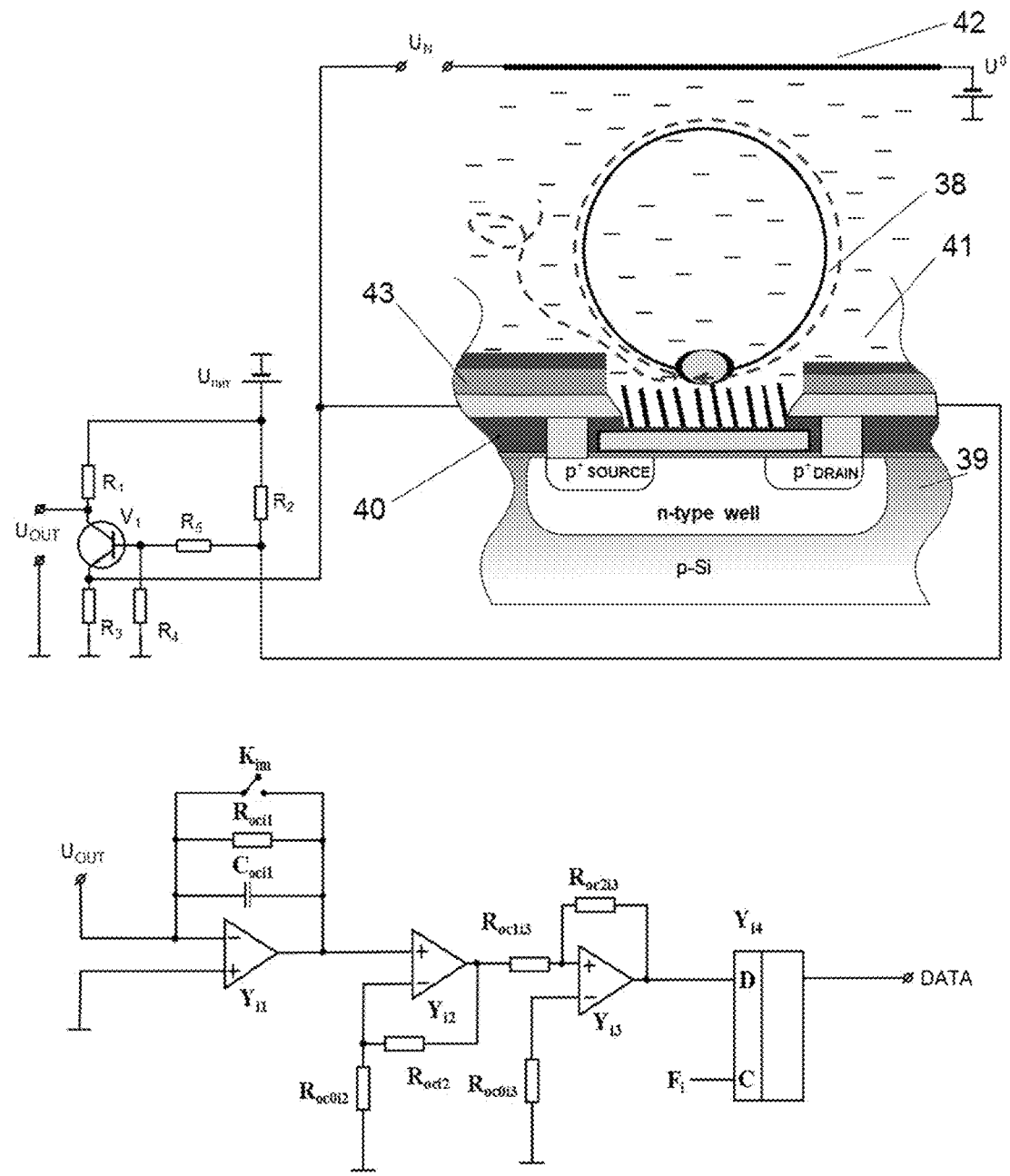

FIG. 15 shows the structure of the sensor and an analog-to-digital cell circuit, which utilize the stochastic resonance phenomenon to record the signal generated by sensor as the result of the separation of pair of charges resulting from nucleotide incorporation by polymerase into polymerizable DNA fragment. 38 denotes a "polymerase-primer-DNA fragment" complex immobilized on the sensor surface, the substrate of p-type silicon in which the sensor is manufactured, an analog-digital cell circuit, an array of cells, the analog-digital circuit of microchip, etc., is designated by number 39, number 40 denotes dielectric insulating layers (e.g., silicon dioxide, $SiO_2$), the number 41 denotes an aqueous solution of the reaction mixture, providing the reaction conditions for polymerization of the DNA fragment, the number 42 denotes the bias electrode, an insulating passivation layer 43 isolates the entire surface of the cell except the sensor surface from the solution. The Example 5 describes the use of stochastic resonance phenomenon of said cell circuitry.

Figure 16:
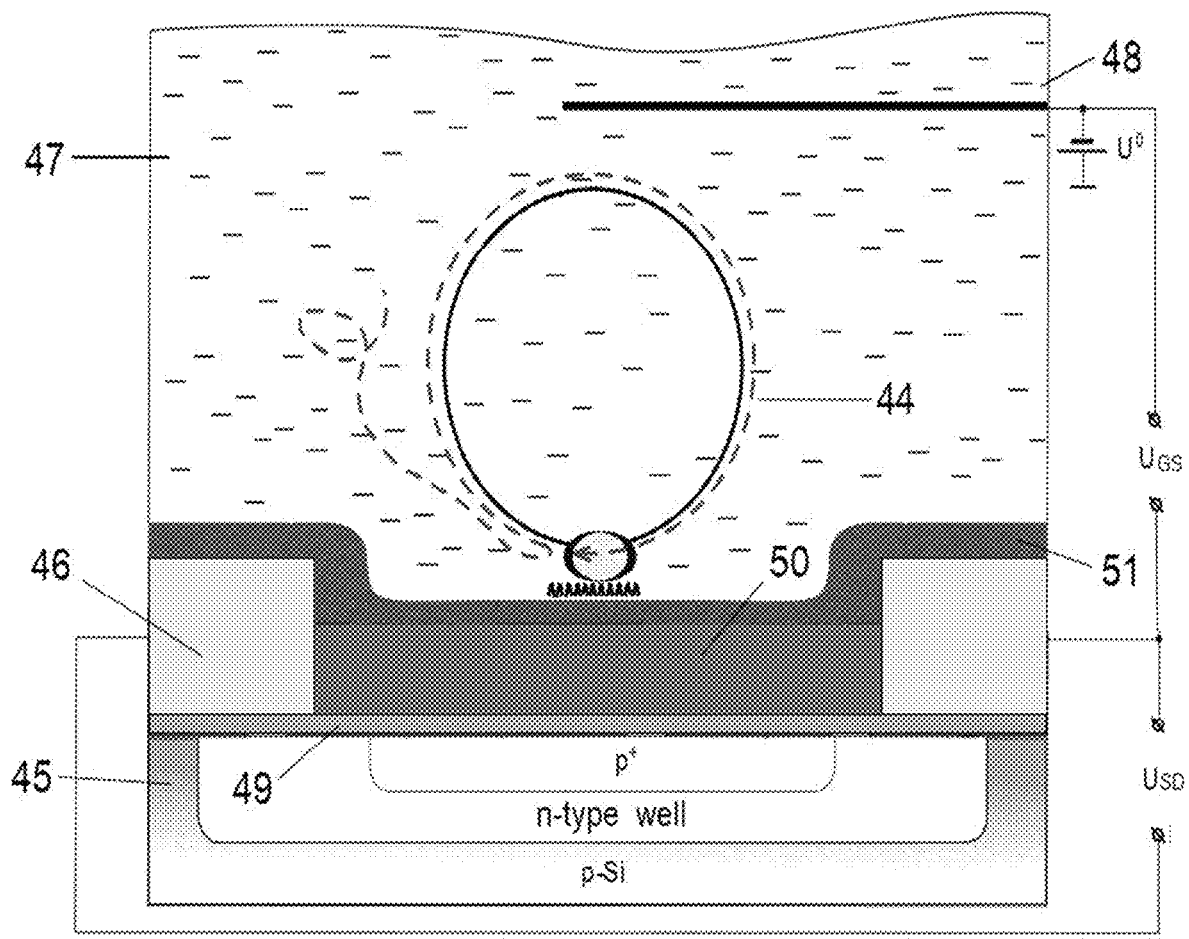

FIG. 16 is a block diagram of a nanowire transistor with immobilized ternary complex which composed of planar thin-film metallic nanostructure deposited on dielectric layer 49 covering the substrate 45; thin-film metal electrode 46 nanostructure (contacts to nanowires) together with a metal nanowire-channel 50 is fabricated on the dielectric substrate by photo- and electron lithography methods using a photo- and electronic resist, etching the exposed area technology, and metal deposition by magnetron or thermal methods. A conductive underlayer (e.g., doped silicon) located under the dielectric layer 49 may also serve as a control electrode. To eliminate contact of lead electrodes with aqueous solution in microfluidic cell they are covered with a thin dielectric layer 51 deposited through the mask. Also, the numbers 44, 47, 48 denote respectively, an immobilized polymerase complex, an aqueous solution of the reaction mixture, and the bias electrode.

FIG. 17A shows the distribution of potential on the plane $z=\varphi(x, y)$ perpendicular to the axis of the nanowire, with the beginning coordinates in the center of the nanowire.

FIG. 17B the graph of equipotential lines is shown; in the center of the closed contours is charged particle; dotted line shows the boundary of the nanowire.

FIG. 18 depicts the distribution of potential along the axis connecting the nanowire center with the center of the charged particle and is normalized to the value of the potential on the surface of the nanowires from the side of particle, diameter of the nanowire is 100 nm (X axis—distance in meters, Y axis—a.u. (atomic units)).

Figure 19:
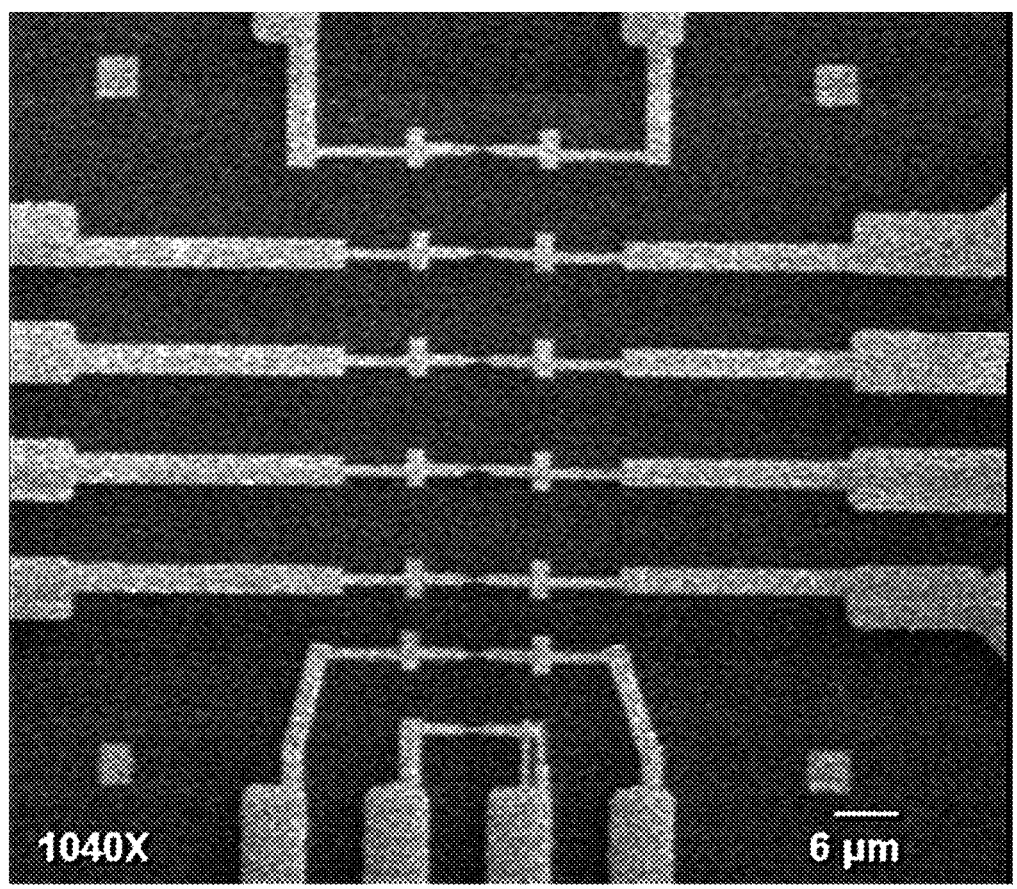

FIG. 19 depicts how individual nanowire transistors can be arranged within an integral structure, which is a chip with an array of nanowire transistors with address bus that permits individual measurement of each nano transistor.

Figure 20:
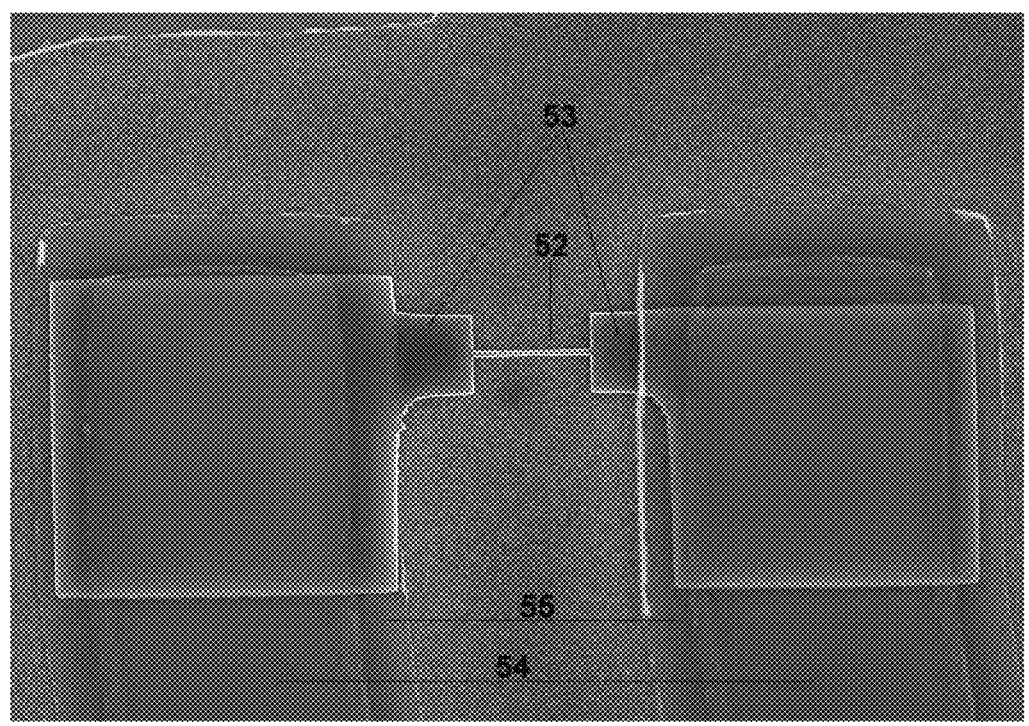

FIG. 20 shows a photograph of the fabricated nanowire transistor with 600 nm $SiO_2$ dielectric layer beneath the metal contacts and the surface insulating 200 nm thick $SiO_2$ layer; 52 denotes a nanowire, 53—contact pads, 54—metallic conductors, 55—dielectric layer insulating the conductors from the aqueous solution.

Figure 21:
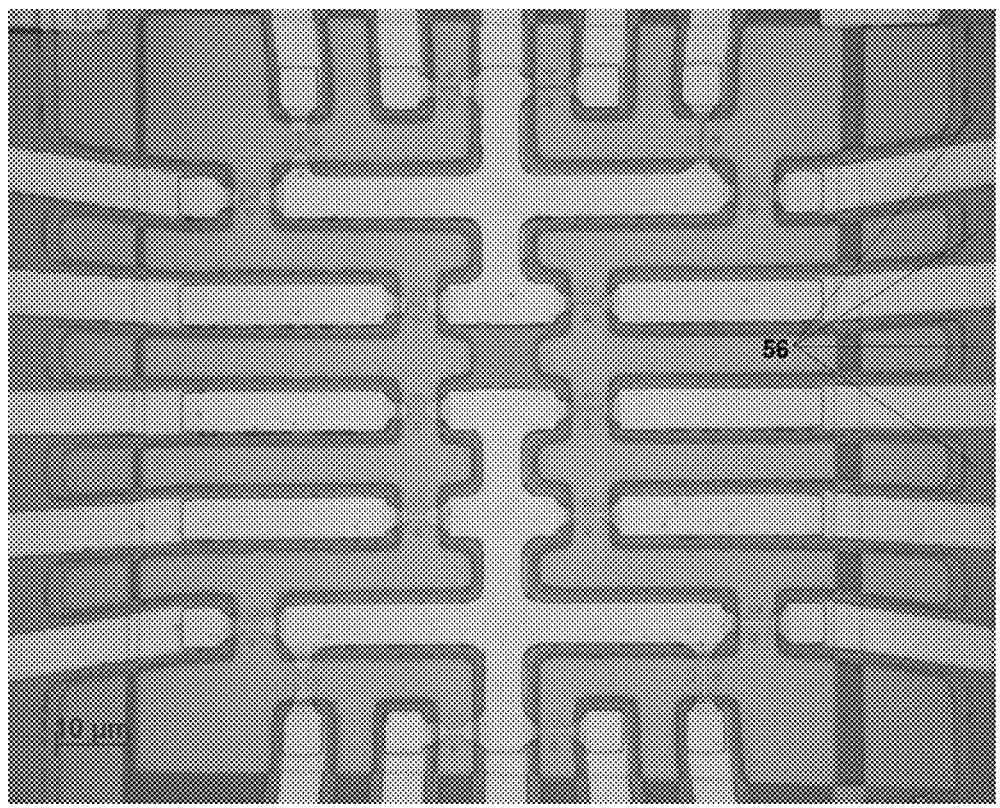

FIG. 21 is a photograph of fabricated nanowire transistors structure in the central region of the chip; number 56 denotes a double dielectric layer beneath the conductors to avoid leakage currents.

Figure 22:
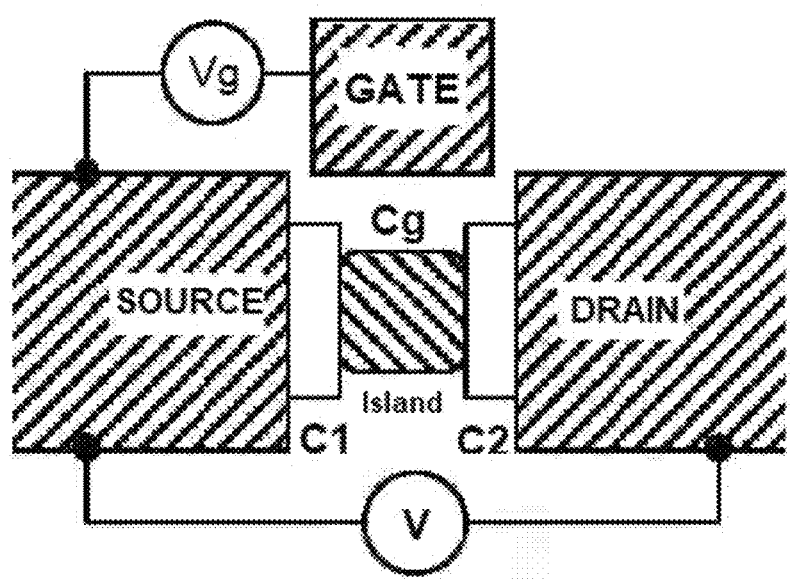

FIG. 22 is an equivalent circuit diagram of the single-electron transistor.

Figures 23A, 23B:
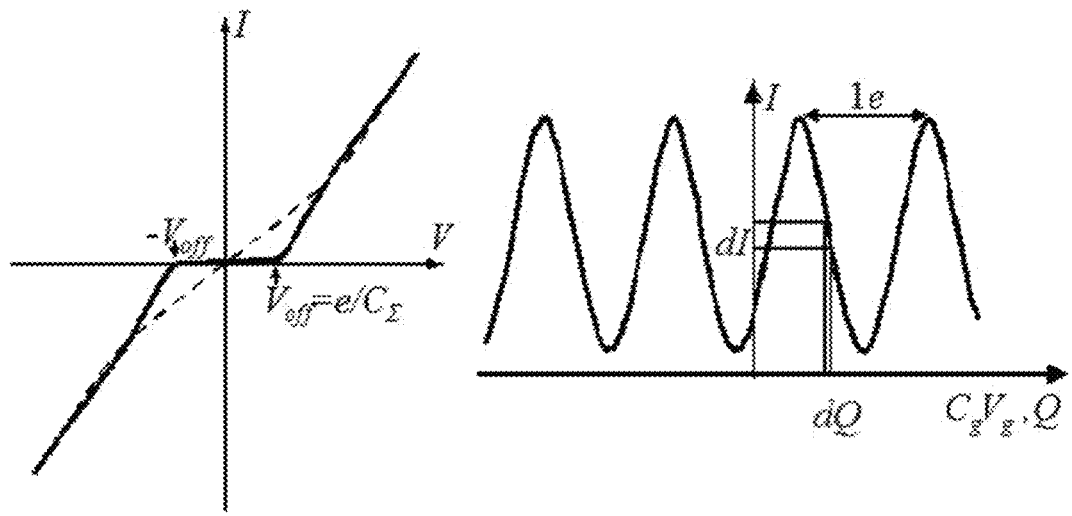

FIG. 23A shows the current-voltage characteristic of the transistor (solid line—Coulomb blockade state; dotted—fully unlocked transistor).

FIG. 23B shows modulation characteristic of single-electron transistor.

Figure 24:
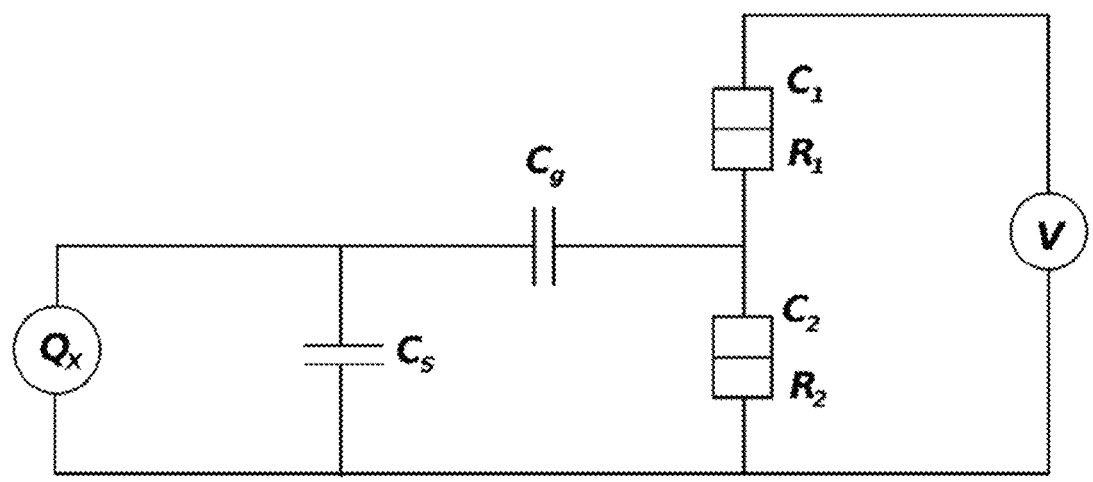

FIG. 24 is an equivalent circuit of the single-electron transistor—electrometer with the source-measured charge $Q_x$ having a self-capacitance $C_s$ and $C_g$ coupling capacitance.

Figure 25:
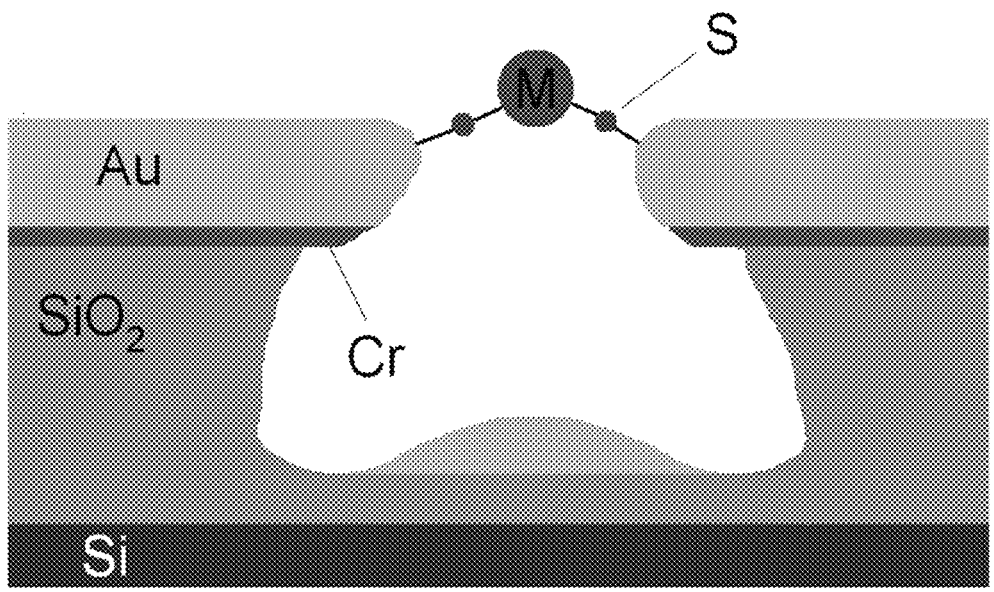

FIG. 25 is a schematic representation of monomolecular transistor with suspended electrodes: M—molecule deposited in the gap and fixed there by means of SH-groups.

Figure 26:
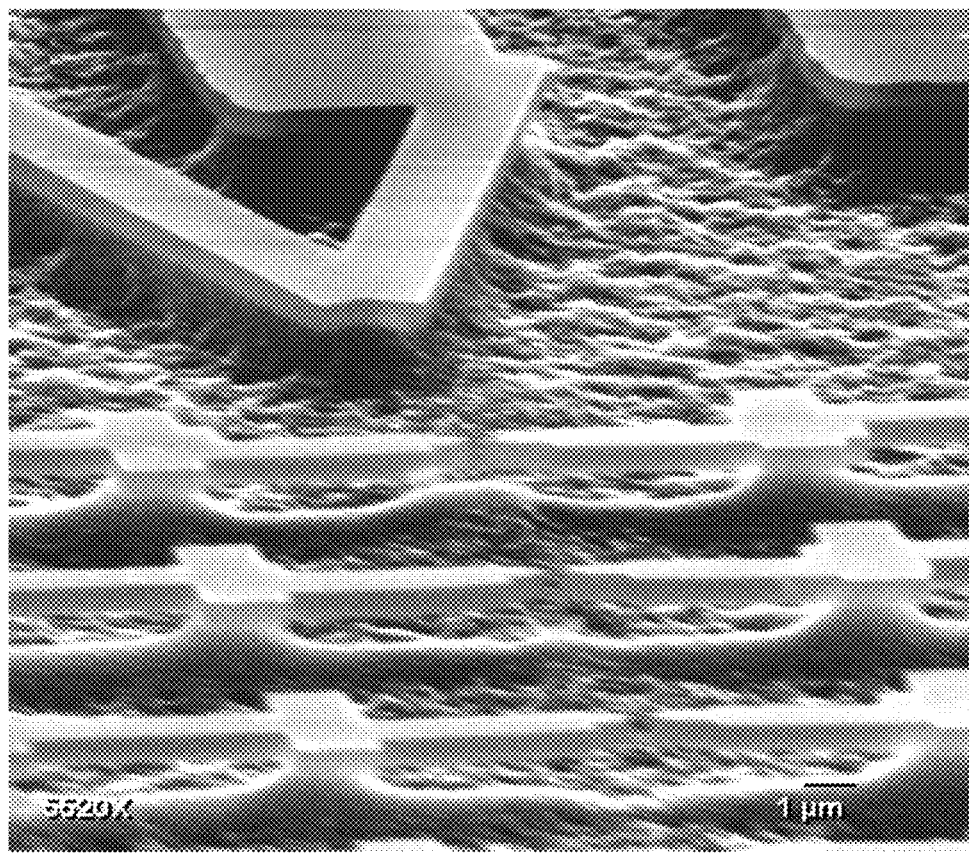

FIG. 26 shows a photograph of the SOI structure with electrodes suspended above the substrate.

Figure 27:
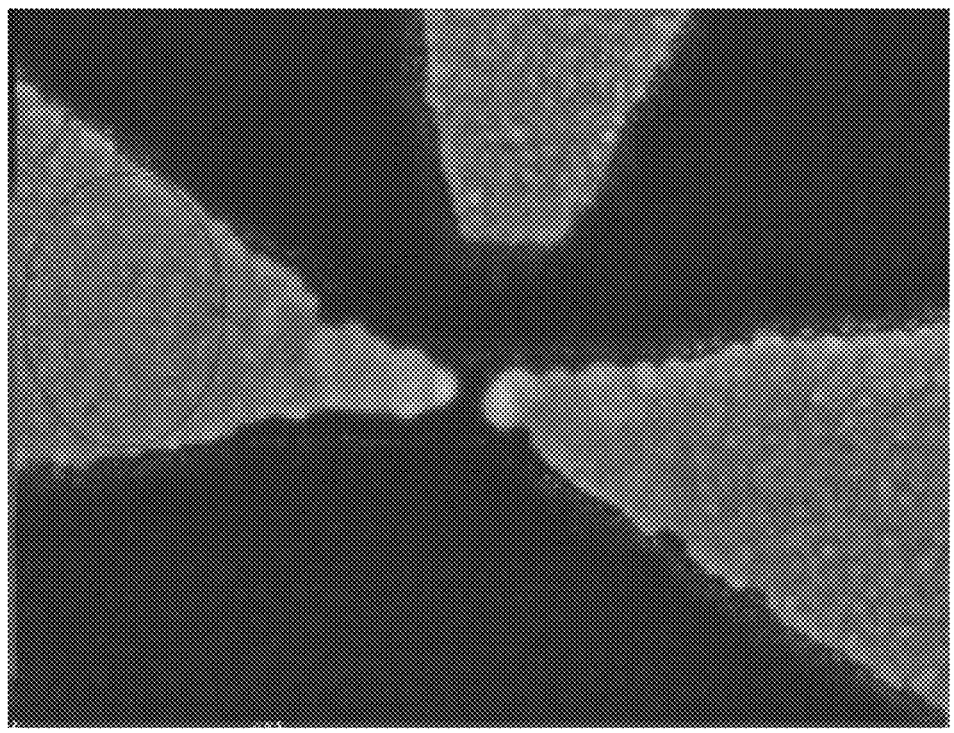

FIG. 27 shows a photograph of the nanostructure of a single-electron transistor with a nanogap prepared by electron-beam lithography.

Figure 28:
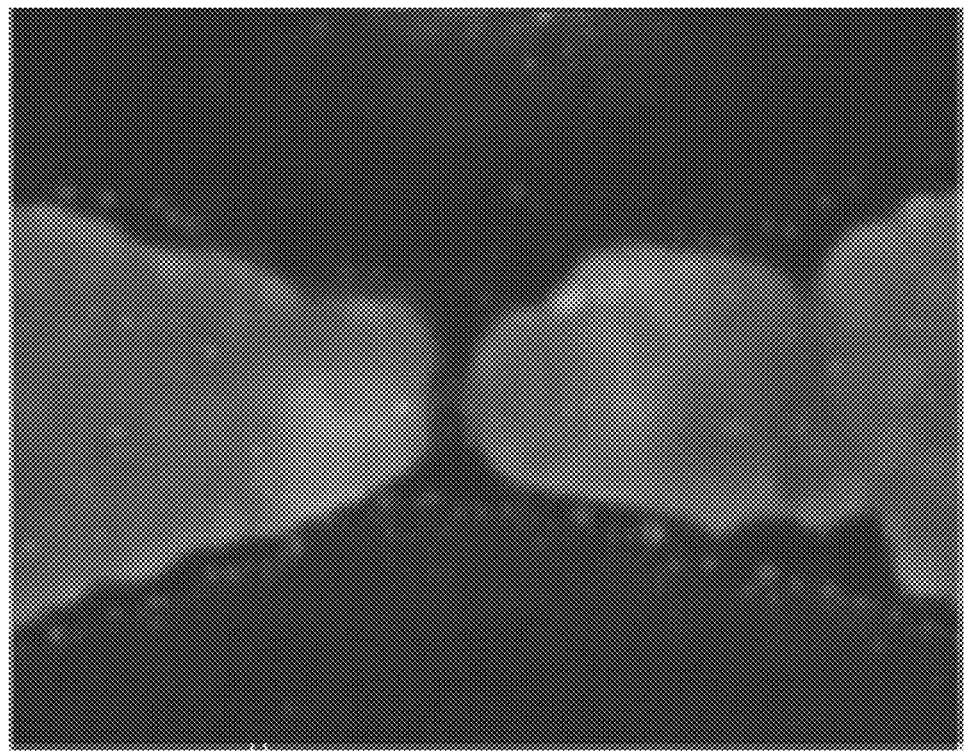

FIG. 28 is a photograph of nanogap obtained by electromigration.

Figure 29:
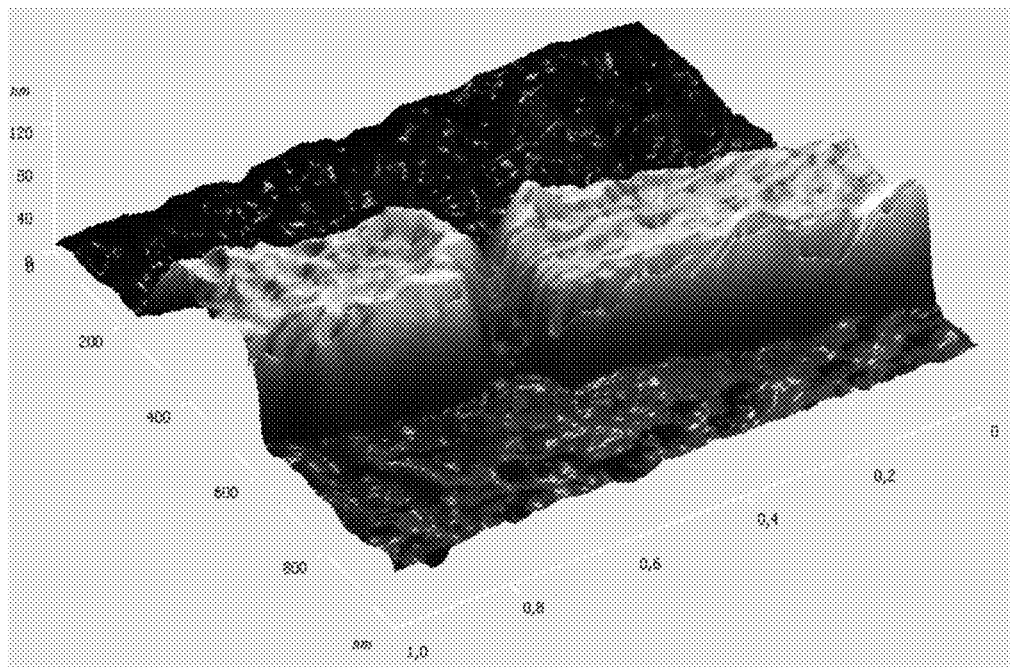

FIG. 29 is a photograph of nanogap obtained by ion-beam lithography (FIB-technology).

Figure 30:
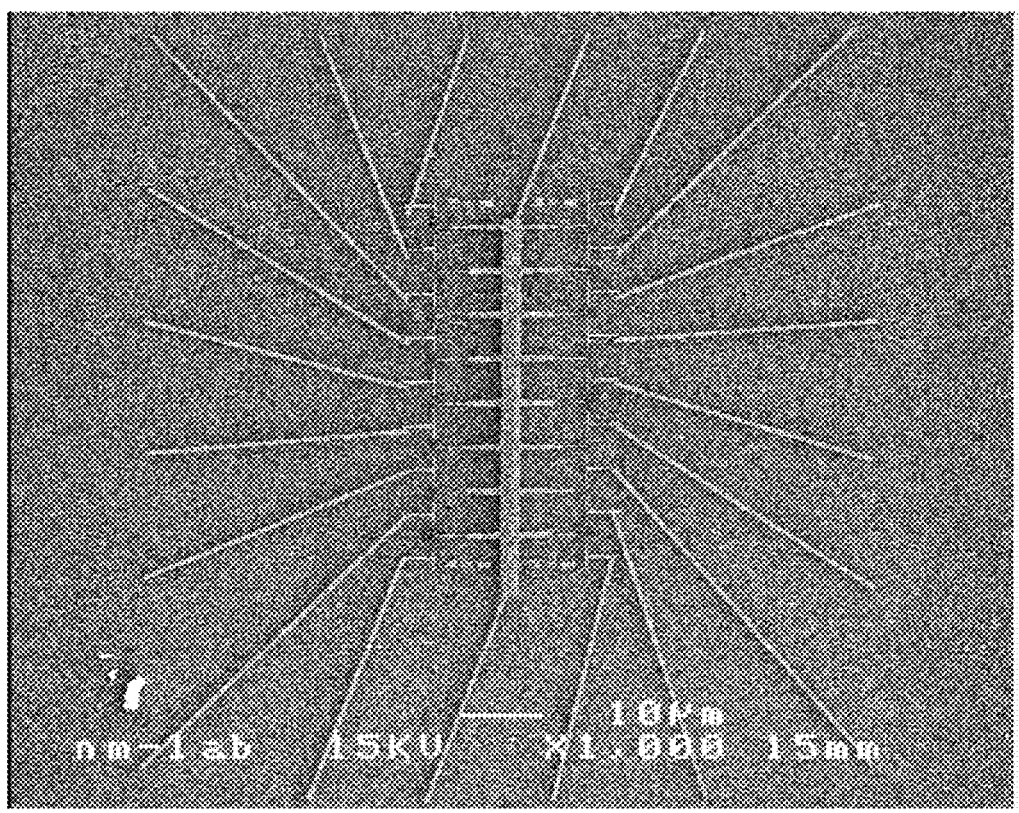

FIG. 30 is a photograph of the nanostructure with 16 cells for transistors with nanogap.

Figure 31:

FIG. 31 shows a photograph of one of the 16 cells having the transistor with nanogap (100 nm distance is indicated).

Figure 32:
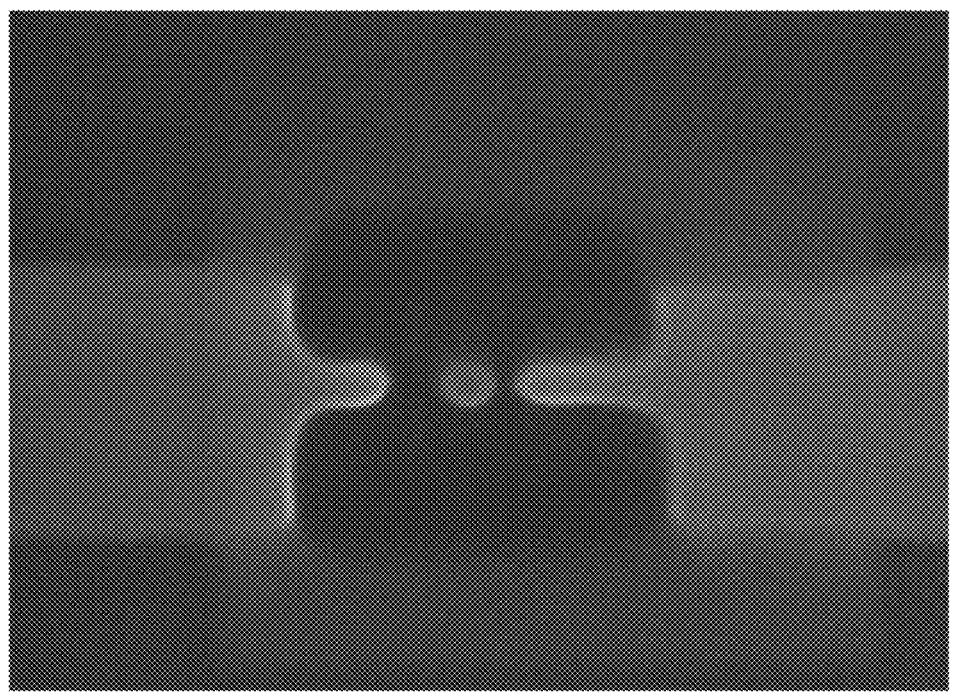

FIG. 32 shows a photograph of the central electrode-island within the structure of the single-electron transistor composed of nanowire prepared using FIB—the technology for the fabrication of nanostructures of desired geometry.

Figure 33:
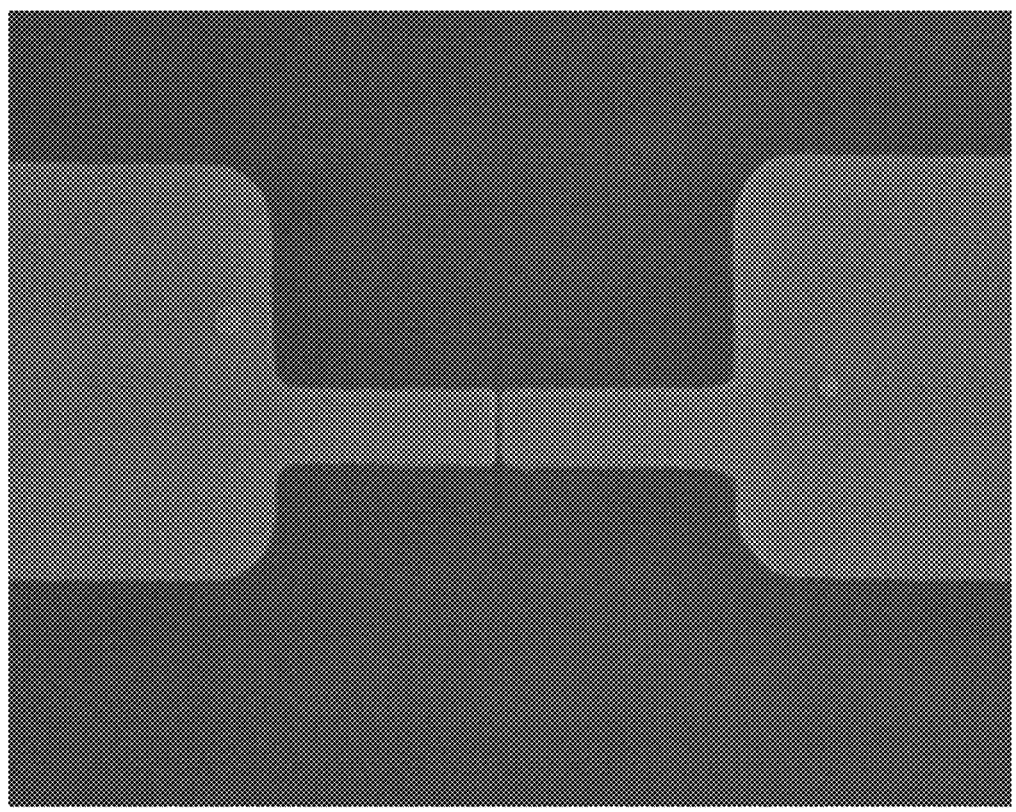

FIG. 33 shows a photograph of fabricated nanogap for creating a molecular single-electron transistor.

Figure 34:
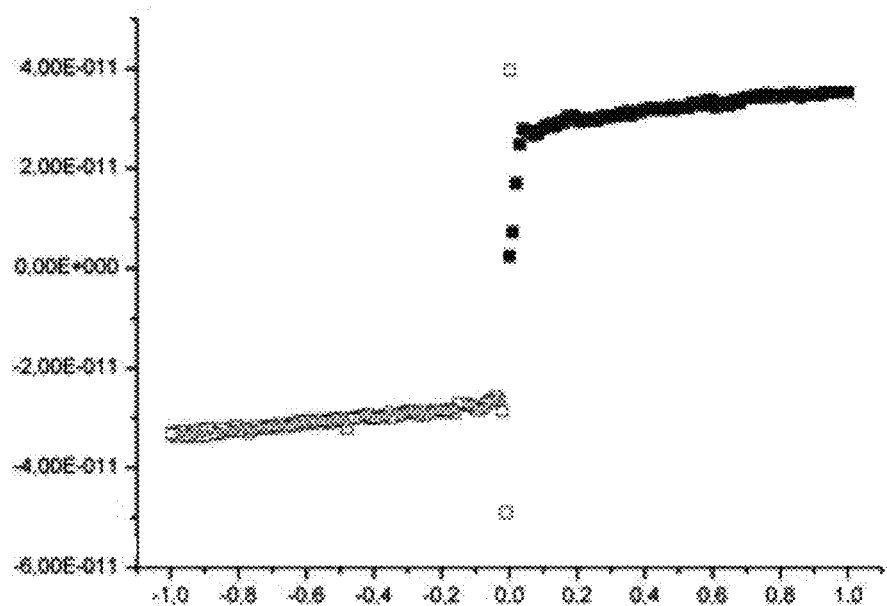

FIG. 34 shows the testing current-voltage characteristic of fabricated nanogap; showing the dependence of the leakage current through the nanogap from applied voltage (X axis— the voltage, in Volts, Y axis—the value of the current, in Amperes); the form of this dependence demonstrates that the nanowire was formed.

The photographs shown in FIG. 20 and FIG. 21, are from Presnov D. E., Amitonov S. V., Krupenin V. A."Field transistor with a channel-nanowire-basis of the molecular biosensor", Radio Engineering. N9/2012, and are reproduced with permission of the publisher.

DETAILED DESCRIPTION OF THE INVENTION

The proposed method of electronic single-molecule sequencing nucleic acids based on these laws. Firstly, the bases of one of the DNA strands are connected to the bases of the other DNA strand via hydrogen bonds by strictly defined Chargaff rules (e.g., nucleotide A is paired with T, G pairs with C), therefore it is sufficient to determine the sequence of bases in one strand in order to determine the nucleotide sequence of the target DNA. Determination of base sequence in a DNA strand during the polymerization reaction is called sequencing by synthesis (SBS) and is used in the present method of sequencing of nucleic acids, DNA or RNA. Secondly, as a result of incorporation of each nucleotide in the complementary DNA/RNA fragment by polymerase the charge separation occurs (Pourmand N., et al, Proc Natl Acad Sci USA, 2006 Apr. 25; 103 (17): 6466-70): one electron remains on the polymerizable DNA/RNA fragment and one proton is released into the aqueous solution. Third, just after charge separation an electron and a hydrogen ion induce countercharges of equal magnitude, but of opposite sign, on the surface of electron sensor surface, which compensate each other, but only for the time until the hydrogen ion will not leave the place of its formation to a certain distance as a result of thermal diffusion and electric field formed by the charge bias electrode of the cell. After that the uncompensated countercharge induced by electron remains on the surface of electronic sensor (Pourmand N., et al, Proc Natl Acad Sci USA, 2006 Apr. 25; 103 (17): 6466-70), whose effect on the electronic sensor is converted by the latter into electrical signal and recorded by subsequent signal amplification and processing circuit, as a charge separation event (event of nucleotide incorporation) and is marked by logical Ones in the output cyclogramm. Fourth, the results of registration of charge separation events will have good repeatability, if the charge separation in the cell of an array take place in one and the same cell location relative to the sensor of this cell, under the same reaction conditions for each incorporated nucleotide. Fifth, if the concentration of one type of nucleotide in the reaction mixture is changed (decreased or increased), and the identity of which is known, then the average (mean) time intervals before incorporation of nucleotides of exactly this type will have a long (at low concentration) or short (for increased concentration) duration, as compared to the average (average) duration of time intervals prior to incorporation of three other types of nucleotides that have optimal working concentration in this mixture for DNA or RNA polymerization reactions. A preferred embodiment is a lower concentration of one type of nucleotide compared to normal concentrations of three other types of nucleotides in the reaction mixture, wherein the rate of incorporation of nucleotides whose concentration is lowered on average becomes lower than the rate of incorporation of nucleotides of other types, whose concentration is normal.

In some embodiments, a significantly lower concentration of one type of the nucleotides is achieved when the concentration is less than the concentration of other nucleotides 5-10 times. In some embodiments, a significantly lower concentration of one of the nucleotides is achieved when the concentration is less than the concentration of other nucleotides 10-20. In some embodiments, a significantly lower concentration of one of the nucleotides is achieved when the concentration is less than the concentration of other nucleotides 20-40 times. In other embodiments, substantially lower concentration of one of the nucleotides is achieved when the concentration is less than the concentration of other nucleotides 40-100 times. Sixth, the accuracy of measurements is a random variable at a plurality of measurement results by the same measurement means, and therefore it can be reduced by averaging the results of repeated measurements; averaging of N uncorrelated statistically independent measurements (i.e. in the absence of constant, e.g., artificial noise (50-60 Hz, etc.)) allows to reduce the random error component of the result in $\sqrt{N}$ times as long as it does not becomes so small that the total error will be determined by systematic component of the error. Seventhly, there are DNA polymerases, e.g. from phage Phi29, having the ability to displace the upstream DNA strand, and thus "read" the DNA several times when the template DNA fragment is circularized, similarly to "rolling circle replication" (RCR); application of this kind of DNA polymerases can increase the accuracy of sequencing by several times by averaging the information about the duration of the time intervals before the events of charge separation (events of nucleotide incorporation).

The proposed method of single-molecule nucleic acid sequencing can be implemented in two basic ways: serial and parallel, each of which has its advantages. For each implementation of the method below there are examples of devices that are given for purposes of disclosure of the characteristics of the present invention and should not be construed as in any way limiting the scope of the invention.

The sequential method of single-molecule sequencing comprises one microchip array of sensor cells, wherein the ternary complex "primer-polymerase-template" is immobilized on the surface of each sensor, after which the four types of the reaction mixtures are sequentially applied to the surface of the array (each reaction mixture was applied once, any order of application of reaction mixtures may be used), characterized in that in each reaction mixture the concentration of only one type of nucleotides is lowered compared to normal concentration of the other three types of nucleotides; the duration of the residence time of each reaction mixture over array of sensor cells depends on the rate of nucleotide incorporation by DNA polymerase (nucleotides per second) and is determined by the time which is necessary for DNA/RNA polymerase to "copy" circular nucleic acid fragment as many times as required to achieve a given accuracy of sequencing. Based on the fact that a number of synthetized DNA copies is limited by processivity synthesized polymerase (e.g., average processivity DNA polymerase Phi29 is ~80,000 nucleotides), the number of copies sequenced inversely proportional to the length in nucleotides of circular template DNA. For example, when the length of the template is 1000 nucleotides it can be read a maximum of 80 times in total for all four reaction mixtures; thus, in each reaction mixture the information about the synthesis of 20 copies can be obtained. With a template length of 5000 nucleotides it can be read of up to 16 times in total for all four reaction mixtures, i.e. in each reaction mixture the information about the synthesis of four copies of template can be obtained. In preferred embodiments, the circular template is read many times in each reaction mixture as needed to obtain the desired accuracy of the sequencing of the DNA fragment, for example, as shown in Example 9 below.

For parallel sequencing method four spatially isolated arrays of sensor cells is used, wherein a complex "primer-template polymerase" is immobilized on the surface of each sensor of each array, after which only one of the four reaction mixtures is delivered on the surface of each of the four arrays, characterized in that in each reaction mixture the concentration of one type of nucleotides is lowered compared to normal concentration of the other three types of nucleotides; the circularized nucleic acid fragment in each cell of each array is "copied" as many times as required to achieve a given accuracy of the sequencing; the reactions of polymerization of DNA fragments in each cell of each array occur asynchronously. Given the processivity of Phi29 DNA polymerase, equal to ~80,000 nucleotides, and the fact that the processivity is a limiting factor in each of the four isolated arrays receiving in parallel the four reaction mixtures, in contrast to single array receiving all four reaction mixtures, as in the sequential mode sequencing (see. Above), the maximum number of copies, potentially read by polymerase in each reaction mixture is four times greater than for a sequential method of sequencing. Thus, when the length of the template in 1000 nucleotides, it can be read maximum 80 times in each the array in each of four reaction mixtures, i.e., up to 80 discrete output sequences of time intervals can be obtained in each reaction mixture from each cell of array. When the length of the template in 5000 nucleotides it can be read 16 times in each of four reaction mixtures, i.e., the accuracy of a parallel sequencing method can be significantly increased compared to sequential sequencing method by accurately determining the nucleotide sequence of longer DNA fragments. But such a potential increase in accuracy is achieved by increasing 4-fold number of microchips with arrays of sensor cells, additional amounts of reagents, and thus the cost of sequencing.

The proposed method of single-molecule sequencing can be implemented in combined manner, sequential-parallel: two of the four reaction mixtures are sequentially applied to two arrays, where the concentration of only one type of nucleotides is lowered in each reaction mixture, and in each reaction mixture—of certain type. But the combined method has no advantages over the maximum values of technical and economic parameters of sequential or parallel sequencing methods.

The major advantage of the sequential sequencing method over the parallel sequencing method is the lack of need to pre-amplify the target DNA/RNA molecules during the construction of the library. Parallel method works only if the original DNA was fragmented and the fragments were clonally amplified during library construction (e.g., by PCR), to provide the delivery of clones of each fragment of the original nucleic acid molecule to all four arrays, as part of ternary complexes. Also, at the same sequencing results accuracy, the cost of sequencing by a sequential method is much lower. Sequential sequencing method yield up to the parallel method only in throughput.

Determining the name of each nucleotide in the analyzed DNA/RNA sequence during sequential sequencing process occurs in three phases:

In the first phase the events of charge separation are registered by each sensor cell of array as a result of incorporation of each nucleotide in the polymerizable DNA/RNA fragment immobilized on the surface within in the complex. Events of charge separation registered by the sensor are converted by the analogue-digital circuit of sensor cell in a useful signal in the form of the output sequence of discrete time intervals, wherein a logical Ones "1" mark those time intervals in which the sensor cell registers the event of charge separation; the output sequences are transmitted to the data processing and display device such as a computer. To obtain a highly precise information on the locations of discrete time intervals in the output sequence corresponding to nucleotides, the concentration of which is lowered into the reaction mixture, several cycles of sequencing of circularized DNA fragment in each cell of array is performed, wherein the number of cycles is the same for each reaction mixture, and obtain a corresponding number of output sequences of discrete time intervals (probably the different amounts of time on the polymerization of the same DNA fragments in each of the four reaction mixtures are required, but the output sequences of discrete time intervals is received from the cells of array by computer in real time, so the computer will give the command to change the reaction mixture or washing buffer in microchip array only after each of the output sequences of discrete intervals of time from each cell is received by computer as many times as it was defined by the user before the start of the sequencing procedure). The possible number of sequencing cycles in each reaction mixture is determined primarily by a length of DNA/RNA fragments and by polymerase processivity.

In the second phase, short and long time intervals prior to incorporation of nucleotides are statistically determined (the number of logic zeros "0" before each logical ones "1" is compared) for each of the output sequence of discrete time intervals, which were obtained in the first phase, and for each cell the data is rewritten in a four sequences of logical ones "1" and zeros, "0" (one for each reaction) so that it is now a logical ones "1" denotes a long time interval corresponding to incorporation of nucleotide of the type, whose concentration has been lowered in the respective known reaction mixture, and a logical zero "0" indicate the short time intervals corresponding to the incorporation of nucleotides species whose concentration was normal in the same reaction mixture.

For each cell the data on location of nucleotides of known types on each of four sequences of logical ones "1" and zeros "0" relative to each other is compared, and by process of elimination, following the rule that at one position in the nucleotide sequence of DNA fragment sequence may be located a nucleotide of only one type, the resulting nucleotide sequence of the DNA fragment is generated.

In the third phase, the nucleotide sequence of entire original DNA/RNA is assembled from the nucleotide sequences of DNA/RNA fragments with the aid of computer program that uses, depending on the task, for example, the RACA algorithm (Kim J., et al., Proc Natl Acad Sci USA, 2013 Jan. 29; 110 (5): 1785-90), or Ragout algorithm of the reference assembly (Kolmogorov M., et al, Bioinformatics, 2014 Jun. 15; 30 (12): i302-9), or algorithms for de novo assembly, for example, algorithms based on the graphical method of De Bruijn (Compeau, P., et al, Nature Biotechnology, 2011, 29 (11): 987-991), or any other suitable algorithms.

Determining the name of each nucleotide type in the analyzed DNA/RNA nucleotide sequence in parallel sequencing method is accomplished in four steps:

In the first phase, the events of charge separation are registered by each sensor cell of each array as a result of incorporation of each nucleotide in the polymerizable DNA/RNA fragment immobilized on the surface within in the complex. Events of charge separation registered by the sensor are converted by the analogue-digital circuit of sensor cell in a useful signal in the form of the output sequence of discrete time intervals marked by logical Ones "1" and Zeroes "0", wherein a logical Ones "1" mark those time intervals in which the sensor cell registers the event of charge separation; the output sequences are transmitted in the data processing and display device such as a computer. To obtain a highly precise information on the locations of discrete time intervals in the output sequence corresponding to nucleotides, the concentration of which is lowered into the reaction mixture over particular array, several cycles of sequencing of circularized DNA fragment in each cell of each array is performed, and the corresponding number of output sequences of discrete time intervals are obtained. The possible number of sequencing cycles in each reaction mixture is determined primarily by a length of DNA/RNA fragments and by polymerase processivity, and cycling is performed the same number of times in each cell of each array.

In the second phase, short and long time intervals prior to incorporation of nucleotides are statistically determined (the number of logic zeros "0" before each logical ones "1" is compared) for each of the output sequence of discrete time intervals, which were obtained in the first phase, and for each cell the data is rewritten in a single sequence of logical ones "1" and zeros, "0", so that it is now a logical ones "1" denotes a long time interval corresponding to incorporation of nucleotide of the type, whose concentration has been lowered in the respective known reaction mixture, and a logical zero "0" indicate the short time intervals corresponding to the incorporation of nucleotides species whose concentration was normal in the same reaction mixture.

Since a parallel sequencing method involves the amplification of the DNA fragments obtained after nucleic acid fragmentation, the number of sequences of logic ones "1" and zeros "0" is minimized separately for each array of cell sensors by sorting, comparing, selecting, averaging identical (with a certain probability) sequences of logical ones "1" and zeros "0", and converting them into a sequence of logical ones "1" and zeros "0".

In a third phase, by sorting, comparing, and elimination in four sequences of logical ones"1" and zeros "0" taken from each of the four arrays of sensor cells, comparing the data on locations of nucleotides of known species in each of four consecutive sequences of logical ones "1" and zeros "0" to each other, and following the rule that at one position in the nucleotide sequence of the DNA fragment only one kind of nucleotide may be positioned, —the nucleotide sequences of nucleic acid fragments are assembled.

In the fourth phase the nucleotide sequence of entire original DNA/RNA is assembled from the nucleotide sequences of DNA/RNA fragments with the aid of computer program that uses, depending on the task, for example, the RACA algorithm (Kim J., et al., Proc Natl Acad Sci USA, 2013 Jan. 29; 110 (5): 1785-90), or Ragout algorithm of the reference assembly (Kolmogorov M., et al, Bioinformatics, 2014 Jun. 15; 30 (12): i302-9), or algorithms for de novo assembly, for example, algorithms based on the graphical method of De Bruijn (Compeau, P., et al, Nature Biotechnology, 2011, 29 (11): 987-991), or any other suitable algorithms.

In preferred embodiments, the registration of charge separation event during incorporation of the next nucleotide is carried out by measuring the current modulation in the channel of the FET by induced potential on the sensor surface (FET gate). In other embodiments, the event of separation of the charges can be registered by measuring the capacitance or conductivity of the surrounding solution.

Registration is performed by an electronic sensor located on the surface of the cell of the array and fabricated based on the nanoscale semiconductor structure, e.g., nanowire field effect transistor (FET), single-electron transistor SET), field effect transistor FET), diode, or based on the structure with S-shaped or N-shaped voltage-current or transfer characteristic (e.g., diode of special design) used in the integrated circuit and implementing a stochastic resonance effect to improve the signal/noise ratio.

For a reproducible registration of the useful signal it is necessary that "DNA polymerase-template" complex is immobilized on the sensor surface for sufficiently long time, longer than the time corresponding to DNA polymerase processivity. For this purpose, the sensor with the surface modified for immobilization of the polymerase complex is used. Analog-to-digital electronic circuit of the cell of the array reads the sensor signals, marks by logical Ones "1" the moments of receiving said signals on the output sequence of discrete time intervals, and transmits them to a computer in real time. Since the name of the type of nucleotides, the concentration of which is lowered into the reaction mixture present over the array, is known, the locations of the nucleotides of this type in the sequence of the nucleic acid sequenced are defined by the results of analysis of the duration of the time intervals proceeding the useful signals, or between them (logical ones "1"), which are formed in the cells of this array.

Important that due to immobilization of the "polymerase-DNA template" complex in the vicinity of the sensor surface, each event of splitting up pair of charges upon incorporation of complementary nucleotides in the polymerizable nucleic acid fragment is performed at a minimum, the same (with a certain accuracy) distance from the sensor surface, and thus ensuring the efficient registration of events of charge separation during the polymerization of the nucleic acid fragments, including long fragments (kilobases long).

In combination with the label-free algorithm of DNA sequencing, it is possible to arrange in each cell of the array the procedure of registration of results of incorporation of complementary nucleotides in the growing strand of the nucleic acid fragment, and, based on the information on the magnitude of the discrete time intervals between the recorded results of nucleotide incorporation, determine the name of each nucleotide in the sequence of the original nucleic acid fragment.

Use of the invention will improve performance and accuracy of procedure of sequencing of nucleic acid molecules, including for use in medical diagnosis purposes.

In some aspects, the invention provides a method for nucleic acids sequencing, which belongs to the group of sequencing-by-synthesis (SBS) sequencing methods, and based on the detection of results of nucleotide incorporation in the polymerizable strand of nucleic acid by polymerase. In contrast to some current commercialized sequencing techniques of this group, the method of the present invention utilizes natural nucleotides and polymerase, which has no amino acid modifications required to increase the incorporation of synthetic nucleotides with attached fluorophores or other chemical modifications. The basic principle of the method of the present invention is based on the detection in real-time of the events of separation of pair of charges accompanying single nucleotide incorporation by single polymerase molecule into a growing strand of single nucleic acid molecules in a "DNA polymerase-template" complex immobilized on the sensor surface. The detection of a series of events of a single charge separation is performed by the electron sensor sensitive to a change in the charge. In reactions with four different initial conditions, each of which defined by one of the four types of nucleotides presented in a lower concentration, the temporary series of events of charge separation exhibiting the temporary delays during incorporation of depleted nucleotides are registered. The methods disclosed herein can be categorized as methods of real-time, single-molecule, electronic, asynchronous methods of sequencing.

In some aspects, the invention provides a method for sequencing nucleic acids, comprising: providing a plurality of nanosensor elements (cells) arranged in array, each cell contains charge sensitive device (nanosensor), amplifier and analog-to-digital signal converter, wherein the nanosensor comprises e.g. source, drain and gate (nanosize transistor); providing a sample containing a plurality of circularized molecules of the target nucleic acid; providing an oligonucleotide primer and annealing conditions to form a primer-template complex; contacting the primer-template with a polymerase enzyme to form a ternary complex "polymerase-primer-template DNA"; providing conditions for binding the ternary complex to the surface of nanosensor, resulting in formation of a plurality of nanosensors with single ternary complexes immobilized on the surface; subjecting said ternary complexes to four polymerization reactions, each containing a mixture of four deoxynucleoside triphosphates (dATP, dTTP, dGTP, dCTP), (or the nucleoside triphosphates ATP, UTP, GTP, CTP), wherein each reaction mixture having one deoxynucleoside triphosphates (or nucleoside triphosphate) present at low concentration; detection of events of separation of pair of charges accompanying the incorporation of nucleotide in polymerizing fragment of single-stranded nucleic acid; registration of time-dependent series of events of separation of pair of charges and identification of long time intervals preceding the incorporation of depleted nucleotides for each of the four reaction mixtures, and, thus, the search of positions of each depleted nucleotide type along the target nucleic acid molecule; comparing the sequences of positions of each depleted type of nucleotides for all four reaction mixtures, and determining the nucleotide sequence of the target nucleic acid molecule.

In some aspects, the present invention relates to methods of nucleic acid sequencing, comprising the sequential or parallel execution of polymerization reactions with four reaction mixtures, each of which has one depleted nucleotide out of four, where, for example, the reaction mixture 1 contains a low concentration of the nucleotides A, mixture 2—G, a mixture 3—T, and the mixture 4—C; wherein the multiplicity of the repeated nucleic acid synthesis of target sequence is calculated for each of the four reaction mixtures so as to allow the polymerase to copy the target nucleic acids as many times as necessary to achieve a high (desired) sequencing accuracy. In parallel sequencing method four nanosensor arrays is used, as well as four reaction mixtures, which can be added simultaneously to the four arrays.

In some embodiments, the present invention relates to an electronic single-molecule sequencing comprising providing: a plurality of circular molecules of target nucleic acid (libraries), a condition of assembly of ternary polymerase complex and attaching of said complex to the nanosensor surface, a composition of the reaction mixtures, and a condition for replication (or transcription) by "rolling circle" mechanism.

To implement the above methods according to the claimed embodiments, the electronic single-molecule sequencing apparatus is used, which is also a subject of the present invention. The apparatus comprises a microfluidic device for deploying the reagents to the cells sensors of the array microcircuit; microcircuit of the sensor cells itself (at least one); the electronic device to control: the microfluidic device, a chip/microcircuit, the data exchange with the processing and data display device (PC); computer with special software which register and stores the primary signals generated by the sensor cells of the array, analyzes, processes these data and determines the nucleotide sequence of the target nucleic acids from a plurality of its fragments.

The data processing and display device can be implemented based on a wide range of electronic computing devices such as, for example, a personal computer, laptop, notebook, server cluster, etc. Generally, said device comprises one or more processors executing the basic processing operation in the implementation of a method and a random-access memory (RAM) intended for storage of operational instructions executed by one or more processors.

Hereinafter, a process of sample preparation is described in detail according to the present invention, comprising the isolation of nucleic acids, construction of the library, the formation of "DNA polymerase-template" complexes and their immobilization at the surface of sensors of cell array.

Nucleic acids used in the methods and systems of the invention in sequencing embodiments may be single-stranded and double-stranded, or contain portions of single-stranded and double-stranded sequences. For example, nucleic acid may be genomic DNA, mitochondrial DNA, cDNA, mRNA, ribosomal RNA, small RNAs, non-coding RNAs, small nuclear RNA, small nucleolar RNA and Y RNA. In some embodiments, nucleic acids are extracted and purified from the specimen or a sample. In some embodiments, the RNA is converted into DNA during reverse transcription, with the help of reverse transcriptase—a specialized DNA polymerase capable of synthesizing a DNA strand using the RNA as a template. Nucleic acid (e.g., genomic DNA) used in embodiments of the invention may be isolated/prepared from any organism of interest. Such organisms may be, for example, animals (e.g., mammals, including humans and primates), plants, fungi, or pathogens, such as bacteria or viruses. In some embodiments, the nucleic acid (e.g., genomic DNA or RNA) are bacterial or viral nucleic acids.

The nucleic acid is prepared from the samples of the organism of interest. Nonlimiting examples of samples include cells, bodily fluids (including, but not limited to, blood, urine, serum, lymph, saliva, anal and vaginal secretions, perspiration and semen), samples from the environment (e.g., samples from water, soil, air, agriculture), samples of biological warfare agents, research samples (e.g., products of nucleic acid amplification reactions such as PCR, or whole genome amplification reaction), the purified samples, such as purified genomic DNA, RNA preparations and untreated primary samples (bacteria, viruses, etc).

Methods for preparing nucleic acid (e.g., genomic DNA) is well known in this field of research (e.g., Sambrook et al, Molecular Cloning: A Laboratory Manual (1999)).

In some embodiments, the nucleic acids used in this invention, represent the genomic DNA. In some embodiments, the nucleic acids are part of the genome (e.g., part of the genome of interest for a specific/particular application, e.g., the panel of genes that may carry the mutation in a cohort of populations, e.g., patients having cancer). In some embodiments, the nucleic acids are exome DNA, for example, part of the complete genome enriched with transcribed DNA sequences. In some embodiments, the nucleic acids are part of or the whole transcriptome, e.g., a set of all mRNAs or transcripts produced by the cell or cell population.

In some embodiments, the nucleic acid (e.g., genomic DNA) are subjected to fragmentation. Any fragmentation method can be used. For example, in some embodiments, nucleic acids are fragmented by mechanical means (e.g., ultrasonication, or nebulization), chemical or enzymatic methods (e.g., by using endonucleases). Methods of fragmentation of nucleic acids are well known in the field of the present invention (e.g., U.S. Pat. No. 9,127,306 B2). In certain embodiments, the fragmentation is performed by ultrasonication (for example, using focused ultrasound irradiator from Covaris, USA). In other embodiments, the fragmentation is performed by treatment of the nucleic acids by nucleases or mixtures thereof (e.g., a mixture of nucleases called Fragmentase, New England Biolabs, USA). In some embodiments, the size of the fragmented nucleic acid is in the range of 50-200 base pairs (bp). In some embodiments, the size of the fragmented nucleic acid is in the range of 100-500 bp In some embodiments, the size of the fragmented nucleic acid is in the range of 200-2000 bp In some embodiments, the size of the fragmented nucleic acid is in the range of 500-5000 bp In some embodiments, the size of the fragmented nucleic acid is in the range of 1,000-10,000 bp In some embodiments, the fragmented DNA size is in the range 3,000-20,000 bp In some embodiments, the fragmented DNA size is in the range of 5000-40000 bp In some embodiments, the techniques described in this section are the purification/extraction of nucleic acids from biological samples, and their preparation for sequencing. Some methods for the extraction of nucleic acids from specimen/samples of various origin use cell lysing enzymes, ultrasonication, high pressure press, or any combination of these methods. In many cases, after the release of nucleic acids from the cells they are additionally cleaned of cell wall debris, proteins, and other components using commercially available methods involving the use of proteases, organic solvents, desalting technique, spin columns, and the binding of nucleic acid with a functionalized matrix, e.g., magnetic nanoparticles. In some instances, the nucleic acid is a cell-free nucleic acid (e.g., so-called liquid biopsy) and doesn't require the extraction from the cell process.

Methods for constructing libraries of nucleic acids of the present invention have the ultimate goal of creating a circular DNA template, which serves as a substrate for DNA polymerase reaction via mechanism of "rolling circle replication" (RCR)—a preferred method of DNA synthesis used in the present invention. Such circularized DNA template with unknown nucleotide sequence is sequenced multiple times repeatedly by the methods outlined in the present invention in order to achieve high accuracy of determination of the nucleotide sequence of the circular template.

Figure 1A:
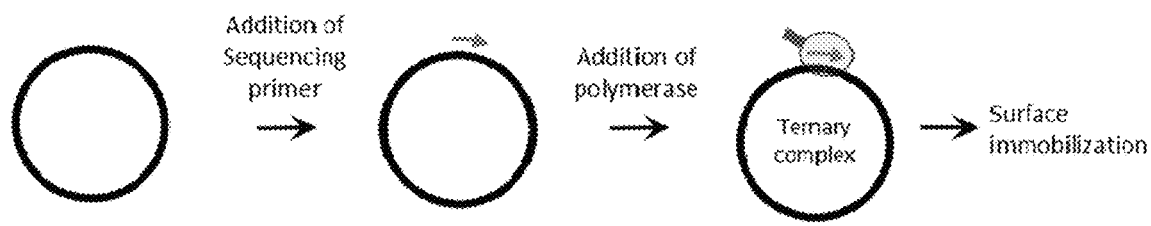
FIG. 1A shows single-stranded DNA circle.
Figure 2:
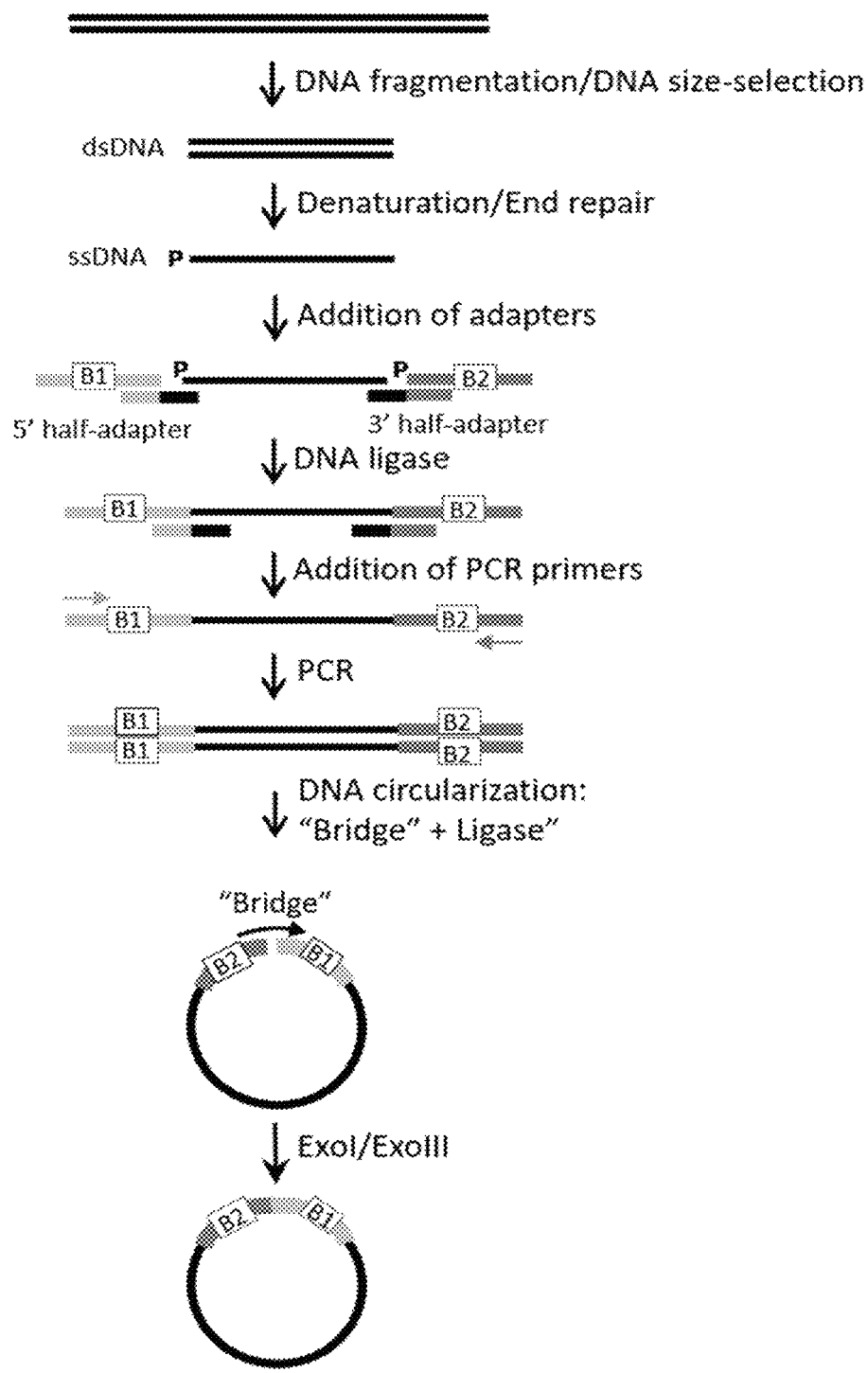
FIG. 2 is a diagram of an exemplary sample preparation method.

In some embodiments, the circularized template comprises a DNA polymer, and the polymerase comprises an RNA polymerase, such as RNA polymerase from bacteriophage T7, and a sequencing process is performed by the mechanism of "rolling circle transcription" (Mohsen and Kool, Acc. Chem. Res., 2016, v. 49 (11): 2540-2550). In some embodiments, the circularized template for the polymerase is covalently closed completely single-stranded DNA (FIG. 1A). Methods for construction of such templates are well known in the field of science to which this invention pertains. An example of this method is shown in detail in FIG. 2.

Figure 1B:
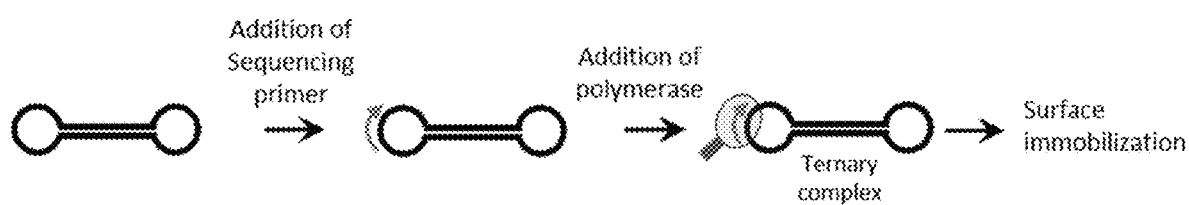
FIG. 1B shows dumbbell circular DNA.

In some embodiments, the circularized template can be in the form of double-stranded DNA circle having a "nick" or "gap" in one strand (FIG. 1B). The 3' end of such template serves as the binding site of DNA polymerase and the start of DNA synthesis. Such template can be constructed via two enzymatic reactions. First the ligation of a double stranded adapter to the ends of the double-stranded sample DNA fragment is performed by using DNA ligase. This can be implemented as a ligation of "blunt" ends, or as a ligation of an adapter having a protruding 3' T-ends with the DNA fragment, in which nucleotide A is added to the 3' ends. Then the double-stranded DNA fragment flanked by adaptors is directly circularized with the help of DNA ligase, or the additional "bridge-adaptor" with the ends complementary to the ends of already ligated adaptors is added to circularize template (complementary "sticky" ends are used for example).

In other embodiments, the template can be a topologically closed circularized partially double-stranded structure in the form of "dumbbell DNA". Such structure allows to determine a sequence of two strands of double stranded region of "DNA dumbbells" (FIG. 1B), sense and antisense, when sequenced by RCR mechanism. Methods for constructing such DNA dumbbells are well known in the art (for example, Travers K J, et al., *Nucleic Acids Research,* 2010, Vol. 38, No. 15, e159).

Figure 1C:
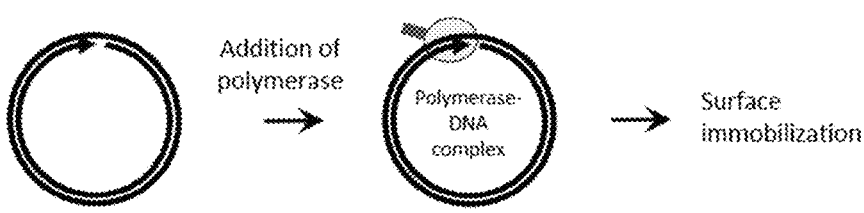
FIG. 1C shows Double-stranded DNA circle, in which one strand is covalently closed, and the second—not.

In some embodiments, the method of constructing libraries of circularized single-stranded DNA molecules comprises several sequential steps. An example of such a method is shown in FIG. 1 and comprises of the following steps: (a) fragmenting DNA obtained from a sample to generate a plurality of DNA fragments; (b) size selection of fragmented DNA; (c) denaturing the fragmented double-stranded DNA of the desired size to obtain single-stranded DNA, where denaturation is performed by thermal or chemical method; (d) the repair of 5'- and 3'-ends to reconstitute the 5'-phosphate and 3'-hydroxyl groups; (e) ligating the 5' and 3' half-adaptors to the repaired single-stranded DNA fragments, thereby obtaining a plurality of single-stranded DNA fragments, flanked by half-adapters; (f) amplification of the ligated molecules by polymerase chain reaction (PCR), wherein the forward and reverse primers are oligonucleotides homologous to the sequences of attached half-adapters; (g) denaturing the amplified DNA fragments to render them single-stranded; (h) circularization of single-stranded DNA fragments comprising of (1) annealing of the "bridge"-oligonucleotide to the ends of single-stranded fragments, thus bringing closer the 5'- and 3'-ends of the adapter sequences and resulting in the formation of double-stranded nicked (containing a "nick"—single-stranded DNA breakage point) region in circularized single-stranded fragment, and (2) ligating said "nick" (single-stranded break of DNA) by DNA ligase leading to formation of covalently closed circular single-stranded DNA molecules; (i) digesting the remaining un-circularized linear fragments and "bridge"-oligonucleotides, both annealed to the template and free in solution, using exonucleases (directional degradation) resulting in the construction of single-stranded circular DNA library.

In some embodiments, DNA fragmentation is carried out using the DNA breakage by ultrasound exposure (e.g., DNA Shearing for NGS: with the M220™ Focused-Ultrasonicator™ Application Notes, www.covarisinc.com; Fisher et al, Genome Biology, 2011, 12: R1). In some embodiments, the DNA is fragmented enzymatically, e.g., using Fragmentase enzyme (New England Biolabs Inc., USA) resulting in the formation of fragments with 5' and 3'-termini having the phosphate and hydroxyl groups, respectively.

In some embodiments, after the DNA fragmentation the size-selection of the resulting fragments is performed to narrow the size-range distribution of fragments (variability range of fragment sizes), and, thus, to obtain libraries with a more uniform size of circularized fragments. In some embodiments, the nucleic acid fragments of 200-400 bp size-range are selected. In some embodiments, the nucleic acid fragments of 400-1000 bp size-range are selected. In some embodiments, the nucleic acid fragments of 1000-2000 bp size-range are selected. In some embodiments, the nucleic acid fragments of 2000-4000 bp size-range are selected. In some embodiments, the s nucleic acid fragments of 4000-6000 bp size-range are selected. In some embodiments, the nucleic acid fragments of 6000-10000 bp size-range are selected. In some embodiments, the nucleic acid fragments of 10,000-20,000 bp size-range are selected. In some embodiments, the nucleic acid fragments of 20000-40000 bp size-range are selected.

In some embodiments, the size-selection of fragments is carried out by Solid Phase Reversible Immobilization (SPRI) developed at Whitehead Institute (DeAngelis M M, et al, Nucleic Acids Res, 1995, 23: 4742-4743), which uses magnetic beads that bind the DNA. For example, AMPur-eXP beads (Beckman Coulter, Inc. USA). In some embodiments, the size-selection of high molecular weight DNA fragments (up to 50 kb) is carried out using automatic DNA fractionation using a special instrument, e.g., BluePippin (Sage Science, Inc., USA).

To construct the library of nucleic acid fragments suitable for sequencing method of the present invention, a plurality of DNA fragments generated by fragmentation must be flanked by adapters—partially or fully double-stranded DNA molecules, obtained by annealing of two oligonucleotides of known sequence. Techniques of attachment of adapters to the 5'- and 3'-ends of the DNA fragments are well known in the field of science, to which the present invention pertains, and are based on the reaction of DNA ligation employing a DNA ligase enzyme, e.g., T4 DNA ligase (New England Biolabs Inc., USA).

In some embodiments, prior to ligation of adapters the double-stranded DNA fragments obtained by ultrasonic fragmentation are subjected to DNA repair reaction(s) to restore the 5' phosphate and 3' hydroxyl end groups, and to convert the 5'- and 3'-protruding and/or recessed ends into blunt ends. This is achieved by incubation of fragmented DNA with phage T4 polynucleotide kinase, phage T4 DNA polymerase, and sometimes additionally with the Klenow fragment of $E.\ coli$ DNA polymerase I.

In some embodiments, when the DNA is fragmented enzymatically, e.g., with the enzyme Fragmentase (New England Biolabs Inc., USA), there is no need to carry out the repair of the 5' and 3' terminal chemical groups, as the enzymatic fragmentation method preserves the integrity of the 5' phosphate and 3' hydroxyl groups at the sites of DNA attacked by nuclease. In some embodiments, when the adapters are attached by blunt end ligation technique, nevertheless, the fragmented by ultrasound DNA is treated with T4 DNA polymerase and sometimes additionally with the Klenow fragment of DNA polymerase I, to blunt the ends prior to ligation of double-stranded adapters to the flanks of fragments.

In preferred embodiments, the fragmented DNA is first denatured and then ligated into the single stranded form to the adapters, as shown in FIG. 1. In this case the repair of the ends is limited by repair of 5' phosphate and 3' hydroxyl groups when DNA was fragmented by physical means, e.g., sonicated, or the repair is not needed at all if the DNA was fragmented enzymatically. Then, the repair of the ends is followed by directional ligation of 5' and 3' half-adapters by a DNA ligase (e.g., T4 DNA ligase, or phage T7 DNA ligase), leading to the formation of double stranded DNA segments having a "nick" at the junction of a fragment and adapters, which is "stitched" by DNA ligase.

In some embodiments, two adapter (e.g., adapter A and adapter B) are ligated to double-stranded DNA fragments by random non-directional fashion—via the reacting of blunt end ligation catalyzed by DNA ligase, resulting in the formation of three types of molecules: flanked by adapters A (AA combination), by adapters B (BB combination), and by the adapter A and adapter B (AB combination). In this method the adapters incapable of ligation to each other are used, i.e., do not form adapter homo- and heterodimers. Selection and enrichment of a library by the DNA fragments having a combination AB is accomplished by PCR, using primers homologous to the portions of adapters A and B (Drmanac R. et al, Science, 2010, v 327 (5961): 78-81).

In some embodiments an nucleotide A is first added to the 3' ends of double-stranded DNA fragment via Klenow fragment of mutant DNA polymerase I, which has no 3'→5' exonuclease activity (3'→5'exo⁻), or Taq DNA polymerase. In this case, adapters are used, which comprise of two annealed to each other oligonucleotides, forming a double-stranded piece of DNA with 5' phosphate groups and T-nucleotides in the protruding 3' ends. In some embodiments, the adapter having a protruding nucleotide T at the end has a partially double stranded structure, for example a Y-shaped structure, often called "fork" (described in U.S. Pat. No. 6,287,825 B1; U.S. Pat. No. 7,741,463 B2), or a "hairpin-adapter" structure (described in U.S. Pat. No. 7,368,265 B2).

In some embodiments, the library of DNA fragments with attached adapters undergoes PCR amplification using forward and reverse primers with phosphorylated 5' ends, which allows to covalently circularize such molecule with the DNA ligase help in the next step, the step of fragment circularization. In some embodiments, the DNA fragments with the attached adapters are phosphorylated by polynucleotide kinase and are circularized without prior DNA amplification.

In some embodiments, the circularization of DNA fragments with attached adapter includes the steps of: (a) denaturing of amplified by PCR or not amplified DNA fragments, and (b) subsequent intra-molecular ligation using auxiliary "bridge"-nucleotide, where the denatured DNA fragments anneal to "bridge"-nucleotide in the presence of DNA ligase, such as T4 ligase, resulting in the formation of single-stranded covalently closed circular DNA.

In certain embodiments, to enrich the library with circular molecules the linear un-circularized single-stranded fragments and the excess of "bridge"-nucleotide are digested (hydrolyzed) by treatment of the ligated mixture with DNA exonucleases, such as, for example a mixture of Exonuclease I and Exonuclease III of $E.\ coli$. The resulting DNA circles represent now a library of DNA fragments from the sample of interest, ready for sequencing by the procedure described by the present invention.

In some embodiments, the entire library of DNA from an individual sample, or unique individual molecules constituting the library, are tagged by adding barcodes (Kinde I., et al., Detection and quantification of rare mutations with massively parallel sequencing. Proc Natl Acad Sci USA. 2011, 108: 9530-9535; and Kivioja T. et al., Counting absolute numbers of molecules using unique molecular identifiers. Nat Methods. 2012; 9: 72-74) to adapter sequence, either before their ligation to the DNA fragments of the sample, or during PCR amplification of DNA, when the barcodes are part of the sequence of the PCR primer(s). Barcode sequences are selected from the sequences of N-mers, where the barcode length N determines the size of the final set of barcodes, which are selected by the criterion of being distinguishable at almost 100% probability from each other. In some embodiments, the one set of barcodes is used. In some embodiments two or more sets of barcodes are used, thus, increasing the number of tagged libraries (or of tagged individual molecules of single DNA library) due to the possibility to apply a combinatorial method of barcoding (FIG. 1). In some embodiments the barcoding is used for tagging the individual libraries prior to their simultaneous sequencing after mixing. The use of such barcoding approaches in sequencing technologies called multiplex sequencing (Smith et al., Nucleic Acid Research, 2010, v. 38 (13), e142).

The sequencing method disclosed in the present invention can be classified as asynchronous single-molecule electronic sequencing method in real time. It does not require multiple modifications of polymerase, except for modification enabling its immobilization on the sensor surface. The sequencing method of the present invention can use both DNA and RNA polymerases. In some embodiments, the polymerase can be an RNA polymerase, which can be selected from the group of polymerases consisting of RNA polymerases of T7 phage, T3 phage RNA polymerase, RNA polymerase of phage SP6, and *E. coli* RNA polymerase. These polymerases initiate RNA synthesis in a dedicated portion of the double-stranded DNA called the promoter. Transcription from a circularized DNA template via mechanism of "rolling circle transcription" (RCT) has been demonstrated for T7 RNA polymerase (Mohsen and Kool, Acc. Chem Res, 2016, v 49 (11): 2540-2550).

In preferred embodiments, the DNA polymerase is used. However, such a polymerase must meet several requirements to enable DNA sequencing by the method presented in this invention, namely: (a) possess a strong strand-displacement activity and lack 5'-3' flap-exonuclease activity; (b) lack of 3'-5' exonuclease activity; (c) possess high processivity of DNA synthesis; (d) has the means to be attached to the sensor surface in a manner, which would not alter its functional properties, such as (a) and (c). In comparison with the methods of sequencing of second (e.g., Illumina) and third (e.g., Pacific Biosciences) generation the method presented here does not require introduction of the mutational changes into the amino acid sequence of the polymerase, so that it can use chemically modified nucleotides for synthesis, as the polymerase used in the present invention deals with natural unmodified nucleotides. The polymerase of the present invention needs a strand-displacement activity to be able to carry out DNA synthesis using circularized DNA as a template, such as single-stranded DNA circles, or "DNA dumbbell" structures. This type of DNA synthesis, called "rolling circle replication" (RCR) mechanism, copies the sequence of circularized template a plurality of times, which leads to the formation of long concatemeric single strand products of synthesis. The high processivity of DNA synthesis is required for DNA polymerase to perform polymerization of dozens of thousands of base pairs after a single act of binding to the DNA template. The lack of 3'-5' exonuclease activity is necessary for polymerase to carry the DNA synthesis in the 5'-3' direction, without the possibility of removing nucleotide just incorporated into the DNA strand via error correction activity. If the polymerase will have this error-correction activity, it may sometimes incorporate the same nucleotide twice or more times into the growing polynucleotide, which will lead to a double (triple, etc.) registration by the sensor of the incorporation of same nucleotide, hence to generation of sequencing error. Many of the currently known polymerases (Klenow fragment of DNA polymerase I, DNA polymerase of phage Phi29), and many archaeal DNA polymerase (e.g., Pfu polymerase) have such an exonuclease activity, which plays an important role for high fidelity reproduction in the natural DNA synthesis, since it allows to carry out correction of stochastic incorporation of incorrect nucleotides, however this is unacceptable for sequencing by the method of the present invention.

In preferred embodiments, a mutated 3'-5' exo⁻ polymerase, e.g., mutant Phi29 DNA polymerase is used. An example of Phi29 DNA polymerase lacking the 3'-5' exonuclease activity is its derivative with the double mutation leading to the replacement of two amino acids—D12A/D66A (Lagunavicius, A., et al, RNA, 2008; 14: 503-513). Other mutations in Phi29 DNA polymerase leading to single amino acid substitutions, N62D and T15I, also significantly reduce 3'-5' exonuclease activity (De Vega M, et al, EMBO J, 1996, 15: 1182-1192). There are other known single and double-mutant versions of Phi29 DNA polymerase, which reduce 3'-5' exonuclease activity of the polymerase 100-1000 times compared to the wild-type enzyme, such as, e.g., D12A, E14A, D66A, and E14A/D66A (described in the U.S. Pat. No. 5,198,543).

In some embodiments, the DNA polymerase of the present invention may be selected from the group of polymerases comprising: phage Phi29 DNA polymerase (3'-5' exo⁻), Large Fragment of Bst DNA polymerase, Bst 2.0 DNA polymerase (obtained by in silico design of the homolog the large fragment of DNA polymerase I from *Bacillus stearothermophilus*, New England Biolabs, USA), Large Fragment of Bsm DNA polymerase (part of the DNA polymerase protein from *Bacillus smithii*, Thermo Fisher Inc., USA), VentR™ (3'-5' exo⁻) DNA polymerase, Klenow fragment of DNA polymerase I of *E. coli*, and the large fragment of Bsu DNA polymerase.

In some embodiments the RCR is initiated on a template comprising a complex "DNA primer-DNA circle" or "DNA primer-DNA dumbbell" by polymerase possessing a strong activity of DNA strand-displacement, which is a prerequisite for highly processive mechanism of RCR. The term "strand-displacement" describes the ability of the polymerase to displace on the way of synthesis the upstream DNA strand. Phi29 DNA polymerase possesses the strongest activity among known DNA strand-displacement polymerases and is most active in the 20-37° C. temperature range. Bsm DNA polymerase has no 5'→3' and 3'→5' exonuclease activity, and the Large fragment of Bsm DNA polymerase has a strong strand displacement activity and is active in a broad temperature range from 30° C. to 63° C. with the optimum at 60° C. Large Fragment of Bsu DNA polymerase has a moderate strand displacement activity and operates in a moderate temperature range, 20-37° C. The Large fragment of Bst DNA polymerase, on the other hand, being an enzyme with strong strand-displacement activity, has a high 65° C. optimum temperature. Two other polymerase produced by Nippon Gene Ltd. (Japan), Csa DNA polymerase (optimum reaction temperature 60-70° C.) and 96-7 DNA polymerase (optimum reaction temperature 50-55° C.), also have a strong strand-displacement activity and are used in reactions of DNA/RNA amplification such as an RCR or LAMP (Loop mediated isothermal amplification). RCR reaction uses a "rolling circle" replicative structure, in which only one strand of circular DNA duplex is used as a template for multiple rounds of replication, and results in a linear DNA amplification generating linear single-stranded concatemers due to re-synthesis of the same circular template. "Rolling circle" is formed when the DNA synthesis initiated at the 3'-end of the primer annealed to the single-stranded circle (or at the 3'-end of the "nick"—single-stranded break in double-stranded DNA, or at the 3' end of the "gap" in DNA); reaches the 5'-end of the primer annealed to the circle (in the case of single-stranded DNA circle), or a double-stranded portion of a "dumbbell" DNA, or the 5' end of the "nick" or "gap". DNA polymerase then begins to displace the upstream 5' end and the DNA strand itself, which is not the template for synthesis of new DNA. Thus, only one DNA strand is copied during RCR. Elongation of synthesized strand continues, and the DNA polymerase moves around the circle, thus replicating the sequence of circular DNA template a plurality of times. The final product of RCR is a connected end-to-end (concatenated) a large number of copies of the circle in the form of single-stranded DNA. The ultimate length of a concatenated DNA depends on the processivity of DNA polymerase. For example, the RCR catalyzed by Phi29 DNA polymerase generates concatemeric products of >50 thousand nucleotides in length in just 20-30 minutes of synthesis time. Such long newly synthesized single-stranded linear molecules spontaneously curl by random fashion into coils with the size of hundreds of nanometers, or even few micrometers in length.

In some embodiments, the RCR is initiated at the 3'-end of the "nick" or "gaps" in the completely double-stranded circular DNA. In this case, the DNA polymerase does not copy first all single-stranded circle template (as in the case of single-stranded circle), or single-stranded DNA portion of the "dumbbell" before starting to displace the upstream strand, but rather immediately (or through one or several nucleotides) begins to displace the 5' end the upstream laying DNA duplex.

In some embodiments, before the polymerase is deposited on a surface to begin sequencing via RCR mechanism, the complexes "Polymerase-Primer-Template DNA" are assembled. This is accomplished by a two-step process: (a) annealing of the oligonucleotide sequencing primer to single-stranded DNA (ssDNA) circle, or to single-stranded loops of DNA "dumbbell", by heating the mixture to a temperature of >95° C. and then slow cool down to ~22-30° C. resulting in the formation of a binary complex "Primer-Template DNA"; (b) subsequent addition of loading buffer (the buffer that promotes binding of the polymerase to the sensor surface, i.e., "loading" of polymerase to the surface) and Phi29 DNA polymerase, leading to polymerase binding with the binary complex "Primer-Template DNA", and thus to the formation of so-called "frozen" or "inactive" (i.e., not operating in this moment, but ready to synthesis in the presence of cofactors) ternary complex "Polymerase-Primer-Template DNA." At this stage the magnesium ions and nucleotides are missing in the reaction mixture to prevent the initiation of DNA synthesis. Further, before the initiation of the sequencing reaction inactive ternary complexes are injected into the flow cell, advanced to the surface of the array, and immobilized on the surface of the sensor cell array.

In some embodiments, the complexes to immobilize containing DNA template, can be assembled in one step by adding loading buffer and DNA polymerase, e.g., Phi29 DNA polymerase, directly to double-stranded DNA (dsDNA) circles having a "nick" or "gap" in one of DNA strands (binary complex "Polymerase-Template DNA"), since a sequencing primer in this case is not needed to initiate sequencing. As in other embodiments, nucleotides and magnesium ions are absent in the reaction mixture to prevent the initiation of DNA synthesis. Further, before the initiation of the sequencing reaction inactive binary complexes are injected into the flow cell and immobilized on the surface of the sensor cell array, which is a sequencing chip.

In some embodiments, prior to loading the ternary complexes into the flow cell and their immobilization on the sensor surface, a controlled, time-limited RCR-mediated DNA synthesis by ternary complexes is initiated in the reaction mixture to obtain a relatively bulky structures representing ternary complexes bound to single-stranded products of limited synthesis rolled into a small size coil. The linear size of such a complex should correspond approximately to the length of the side of the sensor cell, which is controlled by the RCR duration. Such a time-limited controlled RCR is initiated by addition of all four nucleotides and magnesium ions to the ternary complexes assembled in the solution. After addition of the DNA synthesis cofactors and incubation at 25-30° C. for a time necessary to obtain a product of a certain length, e.g., 2-5 minutes, RCR reaction is stopped by adding to the reaction mixture the chemical agent chelating magnesium ions e.g., ethylenediaminetetraacetic acid (EDTA). Collapsing of generated RCR products into a random coil attached to the DNA template and polymerase, results in the formation of compact structures of DNA of a certain diameter. The length of the RCR products depends linearly on the RCR reaction time, and their diameter—not linearly. In some aspects, the coiled concatemer particles have a cross sectional diameter of at least 5 nanometers, at least 10 nanometers, at least 20 nanometers, at least 30 nanometers, at least 40 nanometers, at least 50 nanometers, at least 100 nanometers, at least 500 nanometers, at least 800 nanometers, at least 1 micrometer, at least 2 micrometer or more.

Such a bulky structures consisting of random coil attached to the polymerase and DNA template ("Polymerase-Template DNA-RCR Product") may be used in the methods of the present invention to ensure that only one polymerase complex could bind to the surface of only one sensor due to the effect of steric hindrance. This eliminates the possibility of two or more ternary complexes are binding to one sensor. However, the probability of binding more than one ternary complex with one sensor is relatively high, when ternary complexes have not been subjected to limited RCR when loading of complexes follows probabilistic Poisson distribution (Poisson Distribution), because of the smallness of its size compared to the surface area the binding events are independent of each other. Such method of loading of RCR reaction intermediate, instead of native ternary complexes, also allows to bypass the Poisson rule and achieve nearly 100% occupancy of sensor cell array by ternary complexes. In contrast the loading of the ternary complexes not subjected to limited synthesis follows a Poisson distribution and results at best in ~40% single ternary complex occupancy of sensors.

In some embodiments, the linear size of "Polymerase-Template DNA-RCR Product" complexes is approximately the same as the cross section of the sensor and is at least 5-10 nanometers. In some embodiments, the linear size of "Polymerase-Template DNA-RCR Product" complexes is at least 10-20 nanometers (nm), or 20-50 nm, or 50-100 nm or 100-1000 nm, or 1-2 micrometer.

Methods of the present invention are based on the detection of single events of the separation of charge (generation of one proton and one electron) occurring in the active site of the polymerase enzyme during incorporation of nucleotide into the growing DNA strand. In order to detect such a single event the active site of the polymerase within a ternary complex must be located sufficiently close to the sensor surface. In some cases, the polymerase is located at a distance of about 100 nm from the unmodified sensor surface, of approximately 80 nm from the unmodified sensor surface, of approximately 60 nm from the unmodified sensor surface, of approximately 50 nm from the unmodified sensor surface, of approximately 20 nm from the unmodified sensor surface, of approximately 15 nm from unmodified surface of the sensor, about 10 nm from the unmodified surface of the sensor, about 5 nm from the unmodified sensor surface. In other cases, the polymerase is located at a distance of less than about 5 nm from the unmodified sensor surface: about 4 nm from the unmodified sensor surface, of about 3 nm from the unmodified sensor surface, about 2 nm from the unmodified sensor surface, or approximately 1 nm from the unmodified sensor surface. To meet these requirements, pre-assembled complex "Polymerase-Primer-Template DNA" or "Polymerase-Template DNA-RCR products," must be bound to the sensor surface via the polymerase moiety of the complex. To achieve this, a polymerase molecule must be in a certain way (chemically, or genetically, or biochemically) modified so as to create a binding site on its surface, which would be able to form a chemical bond upon interaction with a chemical group(s), or ligand(s), or protein(s) attached on the sensor surface, where a formed chemical bond(s) is sufficiently strong to withstand the physical and chemical environment conditions accompanying sequencing process. In particular, the identification of potential sites for modification on the surface of Phi29 DNA polymerase greatly facilitated by the existence of a known three-dimensional structure of the protein (Berman A J, et al., EMBO J. (2007) 26, p. 3494-3505). It is important that the controlled modification of the polymerase will be the same for all polymerase molecules within the complexes. Then all the polymerase molecules bound to the sensor array will be oriented the same way and their active centers will be at consistently the same distance from the sensor surface, and thus a smaller variability in detection of nucleotide incorporation by instrument during sequencing. Thus, the polymerase and the sensor surface must be modified so that polymerase moiety of the complex will be bound to the the sensor surface at the closest distance possible for sensor to detect every event of nucleotide incorporation.

Approaches and immobilization techniques can be divided into three groups: physical adsorption, bio-affinity bonding, and covalent bonding. Only the last two types of immobilization may be carried out in a fully controlled manner in terms of a predetermined three-dimensional orientation relative to the surface of the enzyme. Among them, the covalent immobilization is the most preferred approach because of its specificity, stability, and speed.

In some embodiments, the polymerase is immobilized on the surface by tethering via bio-affinity binding. For example, the polymerase is modified by creating one, two or more biotin tags on a protein surface. Such a biotin tags can be an artificial peptide AviTag, consisting of 15 amino acids (GLNDIFEAQKIEWHE) (Avidity LLC, USA; see http://www.avidity.com.), which is specifically recognized by the enzyme biotin ligase (BirA) in E. coli, which biotinylates amino acid lysine (K) in AviTag (Beckett D., et al, Protein Sci 1999 April; 8 (4): 921-9; M. Fairhead and M. Howarth, Methods Mol Biol 2015; 1266: 171-184). After identifying locations on the surface of the polymerase to insert AviTag the modification of polymerase gene is performed, and inserted AviTag becomes an integral part of the enzyme. Further, the purified polymerase is biotinylated in vitro by treatment with biotin-protein ligase (EC 6.3.4.15), which activates the biotin to form biotinyl 5' adenylate and transfers biotin to AviTag of polymerase. Avidity LLC (USA) is also commercialized bacterial strains, e.g. AVB101, which can be used to produce bacterial mass and induce in vivo biotinylation of AviTag. Such biotinylated polymerase can be selectively immobilized on the sensor surface carrying molecules of streptavidin, the protein having strong affinity for biotin. Biotin-streptavidin complex is the strongest non-covalent interaction ($Kd=10^{-15}M$) known between a protein and a ligand. Modification of the surface of the sensor is carried out in several steps. If the surface is composed of silicon dioxide ($SiO_2$), it is first coated with biotin-PEG-silane (e.g., biotin-polyethylene glycol-trimetoxysilane from Laysan Bio., Inc., USA), or with a mixture of biotin-PEG-silane and PEG-silane (e.g. 2-[methoxy (polyethyleneoxy) 6-9 propyl] trimethoxysilane, Mol. Weight 460-590 from Gelest, Inc.). Alternatively, the sensor surface may be modified with so called ZeroBkg «brush» of biotin-PEG (produced by MicroSurfaces Inc. USA). At the next step such pegylated and biotinylated surface is treated with tetrameric protein streptavidin that binds to one or two biotins on the surface, thereby forming a layer of streptavidin. After removal of unbound streptavidin, the DNA polymerase complexes carrying a biotin group within AviTag are added, which bind in turn to the remaining free valences on the streptavidin molecules. In general, deposition of biotin-PEG-silane (or a mixture of biotin-PEG-silane and mPEG-silane) using the technique of covalent transfer from the solvent (solvent-based, covalent grafting technique) improves the specificity of biotinylated polymerase attachment by repulsion of nonspecific adsorption of proteins. A successful example of the use of AviTag technology is the insertion of two biotin "legs" in a DNA polymerase, wherein the polymerase attached to the surface gained more processivity (John G K Williams, et al, Nucleic Acids Research, 2008, Vol. 36, No. 18 e121).

In some embodiments of the bio-affinity binding, when the sensor surface is coated with gold (Au) a polymerase modified by creating one, two or more biotin labels on a protein surface can also be used. Biotin is a vitamin and represents the bicyclic ring and a carboxyl group on the side chain of valeric acid. This carboxyl group of the biotin could become after modification a biotinylating agent. Such biotins functionalized by NHS-ester, hydrazide, or maleimide preserve intact a bicyclic ring required for binding to avidin (S. Luo and D R Walt Anal Chem 61: 1069 (1989); and R N Orth, Clark and T. G. H. G Craighead, Biomed. Microdevices, 2003, 5, 29). Biotin with these functional groups may be deposited directly onto the surface of gold coated with self-assembled monolayer (SAM) by reaction with amines, thiols or other suitable reactive head groups of the SAM. Also, biotin molecules can be created directly on a gold surface by assembling SAM by a number of chemical compounds based on sulfur (S) and containing hydroxyl and biotin groups (J. Spinke, et al., J. Chem. Phys., 1993, 99, 7012). Thus, the polymerase is immobilized on the gold surface by binding to the biotin of the SAM through the formation of "sandwich" biotin-streptavidin-biotin.

In some embodiments of bio-affinity binding to a surface containing silicon dioxide ($SiO_2$), the polymerase may be modified by adding poly-histidine tag, for example six histidine amino acid bases, to the N-terminus or C-terminus of the protein. With this modification the $[His]_6$-labeled polymerase is immobilized on the sensor surface through interaction with chelating ion $Cu^{2+}$ or $Ni^{2+'}$ attached to a layer of high-density polyethylene glycol (PEG) coating the $SiO_2$ surface of the sensor. Such sensor treatment, Ni-NTA-PEG (Ni-n itrilotriacetic acid-PEG), or Cu-NTA-PEG (Cu-nitrilotriacetic acid-PEG) (MicroSurfaces Inc., USA), creates a highly hydrophilic surface that prevents nonspecific binding of the polymerase complex to the surface.

In some embodiments of bio-affinity binding to the surface comprising gold (Au), the polymerase is modified by adding poly-histidine tag, for example six histidine amino acids $[His]_6$, to the N- or C-terminus of the protein. With this modification $[His]_6$-labeled polymerase is immobilized on the sensor surface through interaction with chelating ion $Cu^{2+}$ or $Ni^{2+'}$ attached to self-assembled monolayer (SAM) having NTA (nitrilotriacetic acid) group. Such modification of gold surfaces can be accomplished, for example, by the following two-step method: first using mercaptohexadecanoic acid, the highly ordered layer with terminal carboxyl groups is formed, then the carboxyl group is condensed by derivative of nitrilotriacetic acid containing an amino group to form a peptide bond. NTA group density is controlled by the reaction conditions (Thao T. Le, et al., Phys. Chem. Chem. Phys., 2011, 13, 5271-5278). SAM with NTA groups can be made in another manner, for example by treatment of SAM assembled from 11-mercaptoundecylamine with heterobifunctional linker N-succinimidyl S-acetylthiopropionate (SATP) that results in the formation of sulfhydryl head groups on the surface of the SAM. Then the reaction of maleimide-NTA molecules with sulfhydryl groups leads to the formation of surface coated with NTA groups (Greta J. Wegner, et al., Anal. Chem., 2003, 75 (18), pp. 4740-4746). It is also possible to attach NTA with terminal amins to the SAM carrying the NHS-terminal groups as described in Vallina-Garcia R, et al, Biosens Bioelectron, 2007 Sep. 30; 23 (2): 210-7. Additionally, it is possible to use a self-assembling on Au-surface polymer comprising a polyacrylamide-co-n-acryloxysuccinimide copolymer functionalized with the tandem of active ester (NHS) crosslinked with 3-(methylthio) propylamine (MTP and NTA. The result is a hydrophilic film having a thickness of 2-5 nm carrying NTA groups (Thompson L. B., et al, Phys Chem Phys. 2010 May 7; 12 (17): 4301-8).

In some embodiments, the polymerase, bearing one or more sulfhydryl (thiol) groups (—SH) on its surface, is immobilized on the sensor surface modified with maleimide reactive group. Sulfhydryl groups are found in the side chains of cysteine (Cys, C). Often, they are part of a secondary or tertiary structure of the protein, and may be connected through the side chains by disulfide bonds (—S—S—). The formation of covalent bond between a sulfhydryl group and a maleimide group is one of the most selective and easy reactions in bioconjugation chemistry. The big advantage of this strategy is that for covalent protein immobilization, in general, there is no need for special "tags" and chemical modification of the protein. Furthermore, the thiol group can be used to direct the protein coupling reaction with the surface away from the active centers of the enzyme. Immobilization on the surface is conducted as follows: first the sulfhydryl group (s) are created on the protein surface by reduction of disulfide bonds, or after chemical modification of the primary amines by introducing SH-groups with specific reagents. Then, these sulfhydryl groups are covalently bind to the surface modified (activated) with maleimide. Although disulfide bond between two cysteines in proteins are very stable, they can be restored by reducing agents (R—SH) such as dithiothreitol (DTT), 2-mercaptoethanol, etc.

In some embodiments, for immobilization to maleimide activated surfaces the existing sulfhydryl groups located on the surface of the polymerase can be used, or new cysteines can be created in a predetermined position on the protein surface, based on data of three-dimensional structure of the enzyme. To create new Cys residues it is preferred to replace the surface located serines (Ser) (isosteric and polar amino acid) and alanines (Ala) (small hydrophobic amino acid), as such substitutions is least to affect the protein structure. If necessary, "buried" into the protein and uninvolved in disulfide bond formation Cys residues can be eliminated by the replacement, for example, with Ser and Ala.

In some embodiments, the binding of polymerases having a sulfhydryl group to the sensor surface comprising gold (Au), a chemical reaction based on the self-assembled monolayer (SAM) of alkanethiols with head functional groups, such as amine or carboxyl group, can be used. Sulfur atoms of alkanethiols react with the gold to form a strong, stable bonds, while the methylene chains promote self-assembly of alkanethiol layer due to Van der Waals forces. Then, the SAM with the terminal amine groups is modified with an amine-sulfhydryl crosslinker Sulfo-SMCC (sulfosuccinimidyl 4-(N-maleimidomethyl) cyclohexane-1-carboxylate), which contains NHS-ester and a maleimide reactive groups at opposite ends. As a result, the activated SAM with terminal maleimide groups is created, which is ready to covalently bind the enzyme having exposed sulfhydryl group(s).

In some embodiments, the binding of polymerase with sulfhydryl group(s) to the sensor surface comprising silicon dioxide, can be achieved by the use of linear heterobifunctional PEG reagent, having a maleimide and silane: MAL-PEG-silane, for example manufactured by Creative PEG Works Inc., USA (Ogorzalek, T. L, Examining the Behavior of Surface Tethered Enzymes, Diss. University of Michigan, 2015). Maleimide reacts with a sulfhydryl group, and silane—with a hydroxylated surface of silicon dioxide. PEG moiety inhibits nonspecific binding of charged molecules, such as DNA and proteins to the surface.

A more detailed description of the sequencing apparatus embodiments implementing single-molecule sequencing method, which are also an object of the present invention, is provided below.

The apparatus comprises a sensor chip matrix cells, which is the main component of the device monomolecular sequencing (sequencer) in all its variants of embodiment.

Each chip matrix cell organize the execution of the polymerization of one single-stranded fragment of nucleic acid procedures, comprising immobilized onto a prepared surface sensor cell complex "polymerase matrix DNA primer", the results of embedding polymerase nucleotides during the polymerization reaction, single-stranded DNA fragments (hereinafter—reaction) each cell in the matrix of transformed cells useful signal sensor and recorded analog-digital cell circuit; DNA fragments in the polymerization reaction of the matrix cells occur independently.

Depending on the sequencing task the following options exist:
  the rate of incorporation of nucleotides can be chosen simultaneously for all cells of the array, in a wide range: from 1 nucleotide per second or less, and up to 50-60 nucleotides per second or more, by controlling the values of reaction parameters, such as temperature, pH of the solution, the concentration of the nucleotides in the reaction mixture, the variant of genetic modification of a particular polymerase;

the integrated circuit (chip) of array with an appropriate number of sensor cells can be chosen (may contain from less than 1,048,576 to 256,000,000 and more cells in the array);

one-array or four-array embodiment of a sequencer can be chosen for use in sequential or parallel sequencing method, respectively.

In some embodiments, the rate of nucleotide incorporation is 0.1-2 nucleotides per second. In some embodiments, the rate of nucleotide incorporation is 1-10 nucleotides per second. In some embodiments, the rate of nucleotide incorporation is 10-50 nucleotides per second. In some embodiments, the rate of nucleotide incorporation is 50-100 nucleotides per second.

Integrated circuit of array of sensor cells can be manufactured by a standard CMOS semiconductor process or by customized technological process (depending on the type of sensor construction used). Providing access of the biomaterial to the surface of the sensor of each cell of array is implemented via a set of standard technological operations, stipulated by the process, and the subsequent processing of these surfaces in some way, embodiments of which are described in "Approaches and immobilization technologies".

For example, the sensor cell array chip can both, contain all the blocks listed below, and contain only a part of them. One of possible variants of the block diagram of the sensor cell array chip shown in FIG. 10.

1. Sensor cell array includes:
1.1. Sensor cells arranged in rows and columns in an array, each of which consists of:
1.1.1. Electronic sensor No. 1, forming the desired signal;
1.1.2. Electronic sensor No. 2, which forms the background signal;
1.1.3. Differential charge amplifier connected to the sensors;
1.1.4. Amplifier (repeater);
1.1.5. Schmitt trigger (to avoid interference of the input signal noise with the output signal)
1.1.6. The clock frequency divider, the flip-flop clocking frequency circuit;
1.1.7. Clock frequency trigger (e.g., D flip-flop with the output of the tri-state), for overwriting a signal output from the Schmitt trigger to cell output circuit;
1.2. Temperature sensor with a measuring circuit and the data transfer to the controller chip.
1.3. The vertical shift register receiving data from the cells output circuit—for each column of the matrix cells.
1.4. The horizontal shift register transferring data from the vertical registers to the output USB interface.
2. The data communication controller with the data processing and display device (computer) by USB interface which provides output data from each cell of the matrix to the computer. The data communication controller controls the values of the reference voltages and by the frequency of the clock pulses, which are necessary for the operation of the analog-digital circuits of the matrix cells, controls chip temperature and an aqueous solution above its surface (or just only the temperature of the aqueous solution above of the matrix chip surface).
3. The clock frequency generator generates the frequency grid for analog-to-digital circuits and for sensor cell array data transfer registers controlled by a controller.
4. The reference voltage source provides the necessary currents and voltages for analog-digital circuits of array cells, for data transfer registers.
5. The bias electrode and the voltage source for it, which is controlled by the controller.
6. USB Interface for transferring data between a computer and a microcircuit.

Figure 11:
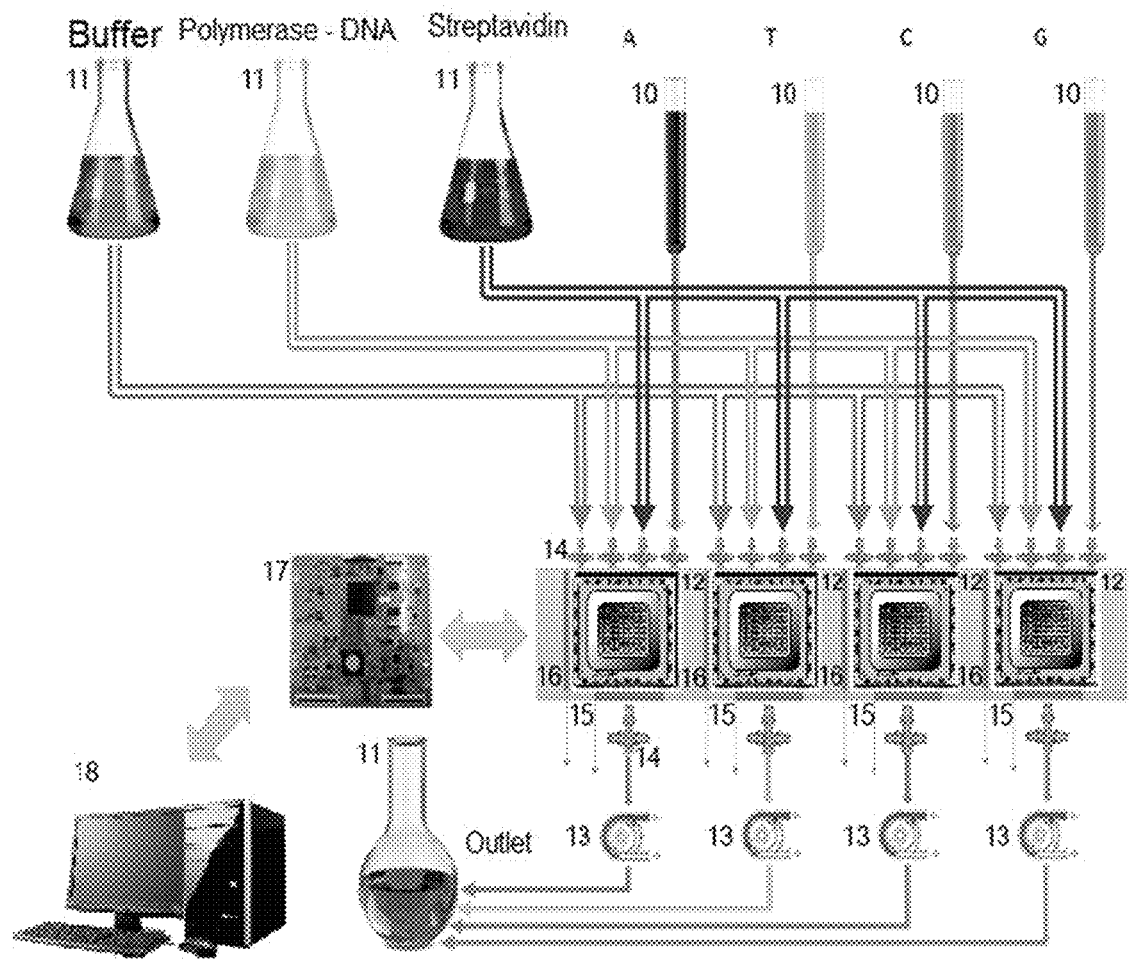
FIG. 11 is a block diagram of apparatus with 4 microchip arrays of one embodiment of single molecule label-free method of nucleic acid sequencing. Integrated circuit of array of sensor cells with a lid of microfluidic device is a major component of single molecule sequencing apparatus 12, microfluidic device comprises four small volume tanks 10 to contain the four aqueous solutions with the reaction mixtures; three large volume tanks 11 to contain, respectively, the buffer, complexes, such as "DNA polymerase-DNA fragment-primer", liquid waste; pump 13 with an electric drive circuit for each microcircuit of sequencing apparatus; shut-off valves 14 with electric drive, providing the possibility of separate feeding of buffer solution, solution with the reagents for immobilization of complexes, and the reaction mixture solution to the surface of the array microcircuit 12; electrodes 15 for measuring the conductivity of the solution at the outlet of the nozzle of each microchip lid 12; Peltier element 16 (which is part of the working solution temperature maintaining device) for each microchip 12 of sequencing apparatus; microfluidic device and each microchip 12 of sequencing apparatus operate under control of the controller 17 and the data processing and display device (computer) 18. The controller 17 functions may be implemented within the microchip 12.
Figure 12:
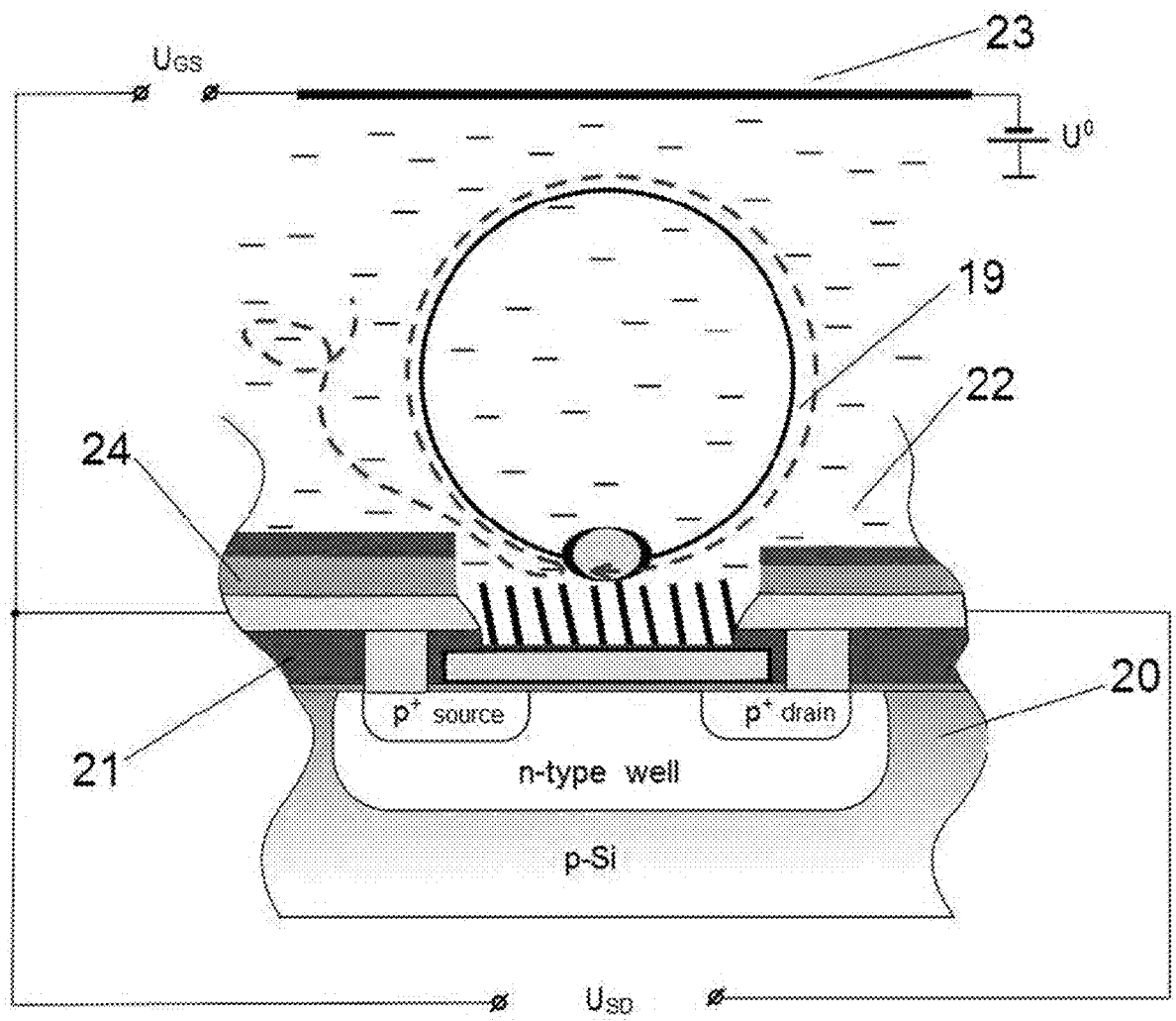
FIG. 12 depicts a structural diagram of a sensor cell of the array with the ternary complex immobilized on the surface of the sensor. The complex "polymerase-primer-DNA fragment" immobilized on the sensor surface, designated as 19, the p-type silicon substrate from which the sensor is manufactured, an analog-digital cell circuit, an array of cells, the analog-digital circuit of microchips, etc. denoted by the number 20, number 21 denotes the insulating dielectric layers (e.g., silicon dioxide, $SiO_2$), the number 22 denotes an aqueous solution of the reaction mixture, providing the polymerization reaction of DNA fragment, the number 23 denotes the bias electrode, an insulating passivation layer 24 to isolate the entire surface of the cell except the sensor surface from the solution.

EXAMPLE embodiment of 4-array block diagram of apparatus embodying the single-molecule sequencing method illustrated in FIG. 11.

Integrated circuit of array of sensor cells with a microfluidic device lid 12 is the main component of the apparatus of single-molecule sequencing.

An integral part of the sequencing apparatus in any of its variants of structural embodiment is a microfluidic device that provides:
  feeding the aqueous solutions on the surface of array chips to immobilize complexes on the surface of the sensor of cell array,
  feeding the aqueous solutions of the reaction mixtures on the surface chip arrays 12 to provide the reactions in the array cells,
  supplying a buffer solution to the surface of chip arrays 12 to prepare these surfaces for immobilization and sequencing procedures,
  measuring the conductivity of the solution at the lid outlet of chip array 12 to determine the quality of washing of the chip surface 12 with the buffer,
  temperature control of the array microcircuit 12 and the aqueous solution above it by means of the Peltier element by the controller microcircuit based on temperature sensor readings; temperature value to be maintained, transmitted to the controller microcircuit by the data processing and display device (PC);
  draining fluids from the surface of the chip array 12.

The structure of a microfluidic device (shown in FIG. 11) may include:
  four tanks of small volume for placement of the four solutions 10 with the reaction mixture;
  a large volume tank 11 for containing a buffer solution,
  a large volume tank 11 for containing complexes, such as "Polymerase-Primer-Template DNA",
  a large volume tank 11 to contain a solution therein of substances needed to prepare the surface of the array to immobilize complexes on the surface of the sensor cells of array microcircuit,
  a large volume tank 11 to drain fluids from the surface of the array chip;
  a lid of sensor cell array chip for a single-array of the sequencing apparatus, and four lids for arrays of sensor cells chip for a 4-array sequencing apparatus—to hold solutions on the chip array surface,
  electrically driven pump 13 for each microcircuit 12 of sequencing apparatus;
  shut-off valve 14 with an electric drive, providing the possibility for separate feeding of buffer solution with the substances for immobilization of the complexes, and solution with the reaction mixture to the surface of the array microcircuit 12;
  Peltier element 16 (which is part of the device for maintaining the temperature of working solution) for each array chip of the sequencing apparatus;
  semiconductor type temperature sensor integrated into the microcircuit of the chip together with the circuit generating an electric signal corresponding to the sensor readings; temperature sensor can be discrete, of semiconductor or other type, and integrated into the lid of arrays of sensor cells, together with the integrated circuit generating an electrical signal;
  electrodes 15 for measuring the conductivity of the solution at the outlet of each nozzle cap of chip 12.

Microfluidic device, and each microcircuit 12 of the array of sensor cells operate under the control of the controller 17, and data processing and display device (PC) 18 of sequencing apparatus, which are also an integral part of the sequencing apparatus. The processing and data display device 18, comprising one or more processors, serves to receive, process and store data on the sequencing of nucleic acids, as well as to control all sequencing procedures. Alternatively, the microfluidic device and microcircuit may operate under the control of the controller chip, wherein the corresponding commands are transmitted by the data processing and display device (PC).

Data storage can be a hard disk drive (HDD), solid state drive (SSD), a flash memory (NAND-flash, EEPROM, Secure Digital, etc.), optical disk (CD, DVD, Blue Ray), a mini disk, or their combination.

Although the invention has been described with the reference to the disclosed embodiments, it will be apparent to those skilled in the art that the specific and in-detail described experiments are given only for the purposes of illustrating the present invention and should not be construed as in any way limiting the scope of the invention. It should be understood that the implementation of various modifications without departing is possible.

The following examples of the device are presented in order to disclose the characteristics of the present invention and should not be construed as in any way limiting the scope of the invention and the essence of the present invention.

Example 1. ROLLING Circle Replication (RCR) by Ternary Complex "Polymerase-Primer-Template DNA" Works on the Solid Surface of the Sensor To construct a single-stranded circular DNA template for the DNA synthesis by Phi29 polymerase, 10 ng of Ultramer oligonucleotide with the length of 177 nt (Integrated DNA Technologies Inc., USA) was used as a template for PCR. Reaction was carried out in the reaction mixture in 50 µl volume containing 2×Q5 Polymerase mix (New England Biolabs, Inc., USA), a template, and 500 nM of forward and reverse PCR primers.

Thermocycling was carried out under the following conditions: 98° C. for 30 seconds; then 30 cycles—98° C. 10 sec, 58° C. 30 sec, 72° C. 40 sec; further 72° C. for 2 minutes. On completion of PCR the double stranded DNA products were purified using a DNA purification kit and eluted with 50 µl of 50 mM Tris pH 8.0.

2 pmoles of PCR product were mixed with 100 nM of "bridge"-oligonucleotide, denatured by heating for 3 minutes at 95° C., followed by a flash cooling in ice for 3 minutes, and circularized by ligating for 1 hour at 37° C. in 1× TA buffer (33 mM Tris-acetate pH 7.5, 66 mM potassium acetate, 10 mM magnesium acetate, and 0.5 mM DTT) supplemented with 1 mM ATP, and 2 units/µl T4 DNA ligase (New England Biolabs, Inc., USA). For the digestion of remnants of un-circularized PCR product and excess of "bridge"-oligonucleotide" the Exonuclease I and Exonuclease III (both from Enzymatics, Inc., USA) were added to ligation mixture to a final concentration of 0.7 units/µl and 1 unit/µl, respectively, and the digestion reaction continued for 30 min at 37° C. The reaction was stopped by addition of EDTA to a final concentration of 25 mM.

Single-stranded covalently closed circles (ssCircles) were purified from the reaction mixture using NucleoSpin® Gel and PCR Clean-Up Kit (Clontech, Takara Co., Japan).

In this example, "bridge" oligonucleotide is also used as a primer for the RCR, from which DNA synthesis is initiated by Phi29 DNA polymerase. For assembly of ternary complexes "Polymerase-Primer-Template DNA", first, 100 fmoles of ssCircles were mixed with "bridge" oligonucleotide (final concentration 0.5 µmole) in a buffer of 10 mM Tris pH 8.0/25 mM NaCl/0.1 mM EDTA, heated to 94° C. for 3 min, cooled to 52° C. for 5 min, and then slowly cooled to 30° C. The resulting complexes "Primer-Template" were obtained. Then, 10× loading buffer was added to complexes to result in 1× final concentration: 50 mM Tris-HCl/10 mM $(NH4)_2SO_4$/4 mM DTT/0.05% Tween 80, pH 7.5. Then Phi29 DNA polymerase exo$^-$ (D66A) bearing N-terminal biotin-tag has been added to the complexes, creating a 2-fold excess of "Primer-Template" complex in relation to the polymerase. The mixture was incubated at 10° C. for 15 minutes to form ternary complexes. The method of attachment of biotin tag to polymerase is well known in the art (e.g., Beckett D., et al, Protein Sci, 1999 April; 8 (4): 921-9; Fairhead and Howarth, Methods Mol Biol, 2015, 1266: 171-184).

The ternary complexes were placed inside a flow cell made of PEGylated by PEG-silane (2-[methoxy (polyethyleneoxy) 6-9 propyl] trimethoxysilane, MPEOPS, MW=460-590, Gelest Inc., USA) glass slide, a thin cover glass modified with PEG-biotin (MicroSurfaces Inc., USA), and the pressure-sensitive adhesive with 100 micrometer thickness (PSA, 3M Inc., USA), which plays a role of a spacer. Before adding ternary complexes, the protein streptavidin was immobilized on biotinylated PEG layer by adding 20 µl 0.1 mg/ml streptavidin, dissolved in a buffer containing 10 mM Tris-HCl/50 mM NaCl pH 8.0. After one minute-incubation, the excess of streptavidin was removed from the flow cell via washing with 100 µl of the same buffer. Thereafter ternary complexes were added to the cell for 15 minutes at 10° C. and immobilized on PEG-Biotin-Streptavidin surface. As a control, the ternary complexes were also placed into the second flow cell, whose surface was not treated with streptavidin. Unbound complexes were removed by washing of the flow cells with 200 µl 1× loading buffer. Then, to start the RCR reaction in the flow cell 1× loading buffer solution supplemented with 10 mM $MgCl_2$ (final concentration) and 400 nM dNTP (final concentration of each nucleotide) was added. RCR reaction continued for 20 minutes at 30° C. The reaction was stopped by adding 25 mM EDTA pH 8.0 solution.

Figure 6A:
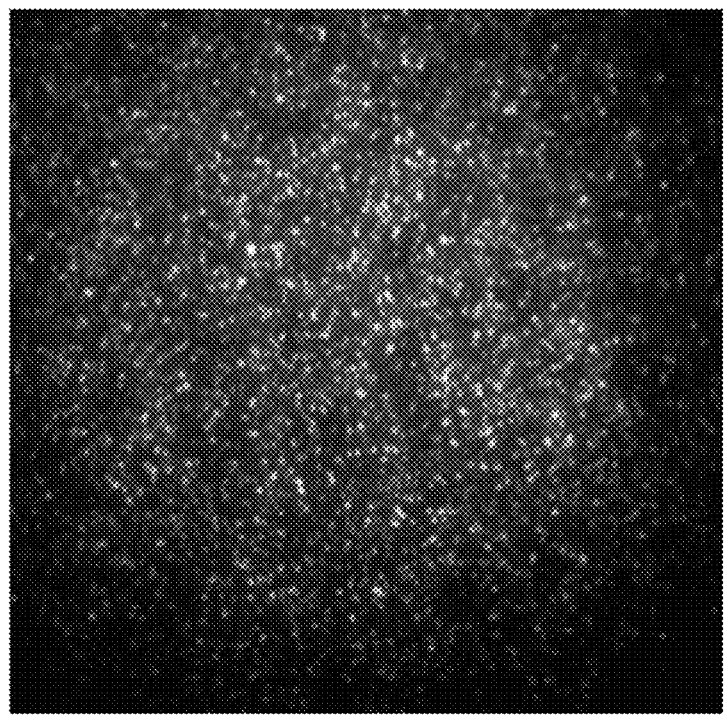
FIG. 6A shows an image acquired by Zeiss Axiovert fluorescent microscope of DNA synthesis reaction products obtained via the mechanism of "rolling circle replication» by Phi29 polymerases which are immobilized as part of the ternary complexes on the surface of the coverglass; products of DNA synthesis are stained with intercalating dye GelStar. The ability of the polymerase Phi29, immobilized on a solid surface, to carry out DNA synthesis using circular template DNA has been demonstrated.
Figure 6B:
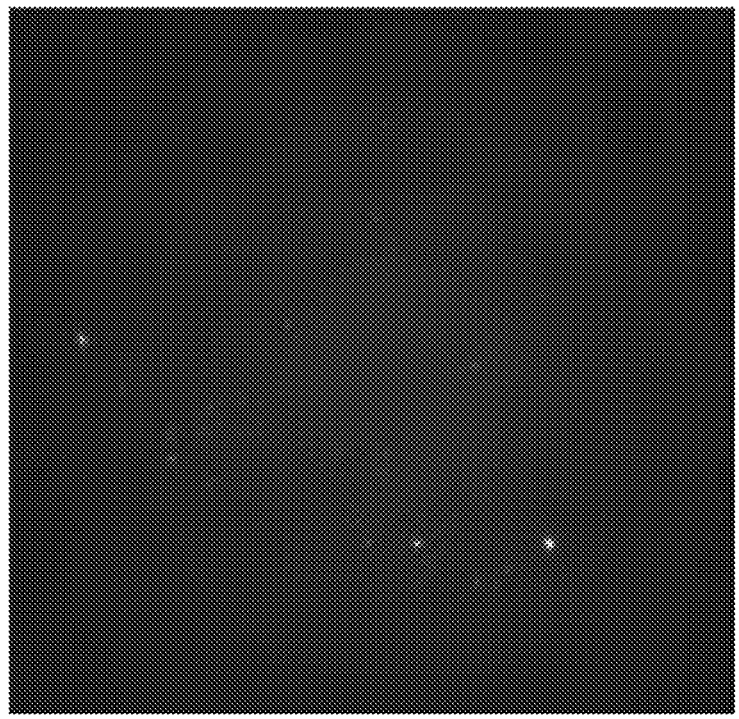
FIG. 6B shows an image acquired by the fluorescent microscope Zeiss Axiovert, where few visible reaction products of DNA synthesis resulted from those ternary complexes which were nonspecifically immobilized on PEG-biotin surface of the cover glass.

To visualize the products of DNA synthesis reaction mediated by Phi29 polymerase at the chip surface, the reaction products were stained with DNA intercalating dye GelStar Stain (Lonza Rockland Inc., Rockland, USA), diluted 10,000-fold in buffer: 10 mM Tris-HCl/50 mM NaCl pH 8.0. Immediately after adding the dye to the flow cell the chip was placed on the fluorescence microscope Zeiss Axiovert, illuminated with 480 nanometer laser, and product's fluorescence was recorded on a digital camera. The results of this experiment are presented in FIG. 6A and demonstrate the ability of immobilized Phi29 DNA Polymerase to carry out DNA synthesis from circular template on the surface. The control coverglass was not passivated with streptavidin and therefore not able to bind the ternary complex, and this leads to the absence of visible products of DNA polymerase synthesis. Some few products that are visible on the control surface, are due to a weak unspecific binding of ternary complexes with PEG-biotin surface (see. FIG. 6B).

Example 2. The Semiconductor Sensor and Circuit of Cell Array Fabricated by Semiconductor CMOS Technology Examples of possible designs of the sensor cell shown in FIG. 12-14, 16, 17, including the scheme, realizing the function of stochastic resonance shown in FIG. 15.

The polymerization reaction of a DNA fragment of polymerase complex 19, 25, 31, 38, immobilized on the cell surface of the sensor, due to the interaction of the polymerase with the reagents of the reaction mixture 22, 28, 34, 41, is accompanied by the separation and localization of negative charge (electron) and the free proton in proximity of the activated segment of DNA fragment. Thus, the result of the reaction is the generation of a pair of electron-proton, followed by localization of electron on activated segment of the DNA fragment and the drift of a proton in an aqueous solution of the reaction mixture in an electric field of the cell in the direction of the bias electrode 23, 29, 35, 42, which is connected to source voltage controlled with a controller of microcircuit of array of cell sensors. During the proton drift its shielding by the negative ions of solution (e.g., OH—) occurs at the characteristic time Tep. In addition, a localized electron residing within the diffusion layer, for some characteristic time Tee also will be shielded by solution ions. Thus, on the receiving electrode (i.e. in the volume of the gate region of the channel of transistor, which reads the charge, —further, the reading electrode), during a characteristic drift time Td of the proton in the working solution increases the amount of charge induced by the superposition of the fields from localized on activated segment of DNA fragment negative charge and positive charge of the proton that is drifting from the place of charges separation in external field in the direction of displacement electrode aggravated by developing shielding of proton by hydroxyl ions. Thus, the fundamentally important factor providing the possibility of occurrence of induced potential at sense electrodes, is the presence of an electric field in an aqueous solution, which increases the drift velocity of a proton, which ensures a large value for the characteristic time Tep of complete screening of protons by negative solution ions. The electric field in the aqueous solution created by the applied bias potential to the electrode which is located, e.g., on the inner side of the chip cover. The bias voltage is given a controlled voltage source (power supply) with respect to the common electrode potential (in Figures not shown). The source of bias voltage is controlled by the microcircuit controller having feedback from analog-to-digital circuit of cell. Once all preparatory operations to the sequencing are completed, the processing and display device (PC) transmits data to the controller microcircuit that the polymerization reactions of DNA fragments, with high probability, have begun in the cells After decoding these data controller microcircuit analyzes the meaning of logical values in the sequence of time intervals from the output of analog-to-digital cell circuit, in series with a time delay, controls the voltage increase onto the voltage source output (power) offset from zero volts to a value which provides registration and signal shaping. Mechanism inducing charge on the surface of the FET gate during the polymerization reaction the DNA fragment and registering the result of its formation is described, for example, in Nadar Pourmand (Pourmand N., et al, Proc Natl Acad Sci USA, 2006 Apr. 25. 103 (17): 6466-70; Pourmand N., et al, A label-free CMOS DNA microarray based on charge sensing, in Proceedings of the IEEE Instrumentation and Measurement Technology Conference, Victoria, BC, Canada, May 12-15, 2008).

The polymerization reaction of the DNA fragment in the cell is organized in such a way that occurs on average a few, for example, five complementary nucleotide embeddings per second. Each nucleotide embedding accompanied by the separation of one pair of charges. The fact of the separation of each pair the charges are recorded and converted by the cell sensor into an electrical signal, which is firstly amplified by a differential charge amplifier, from the output of which is fed to the comparator with a positive feedback (Schmitt trigger); from the output of which the signal is already digitized, for example, by using of D-trigger, by setting its output to the state of logical "1".

Functionally, the induced potential at the gate of the field effect transistor modulates the amplitude of the current in the channel of the transistor, the drain of which is connected to differential charge amplifier; other input of the differential amplifier connected, for example, to the drain of a sensor field-effect transistor, the transistor of which form the background signal of FIG. 14. The output of the differential amplifier is connected to the input of an amplifier, the purpose of which is to obtain such amplitude of the signal, that sufficient to switch the Schmitt trigger or comparator in a state of logical "1". Schmitt trigger output connected to the D-flip-flop input, which is clocked by the clock cell dividing circuit with the frequency of the internal chip oscillator, overwriting the logical values ("1" and "0") from the Schmitt trigger output to the D-trigger output with a frequency exceeding the frequency of the nucleotides embedding during the polymerization reaction, for example, in four times. As a result, the output of the analog-digital circuit will form the sequences of discrete time intervals similar to sequences shown in FIG. 5A:

logical "1" denotes the time intervals when by sensor and analog-digital circuit of the cell the signals of charge separation were registered near the reading electrode. To match recorded facts of the separation of pairs of charges with their cause (by embedding complementary polymerase nucleotide) helps the knowledge a priori the rate of three species of nucleotide embedding, the concentration of which is normal in an aqueous solution of the reaction mixture. First, the values of the parameters of the aqueous solution of the reaction mixtures, such as pH, solution temperature, nucleotide concentrations of all kinds, which provide the desired rate of polymerization of the DNA fragment are calculated. Then the values of these parameters are set for working solutions before starting the sequencing.

First, the values of the parameters of the aqueous solution of the reaction mixtures, such as pH, solution temperature, nucleotide concentrations of all kinds, which provide the desired rate of polymerization of the DNA fragment are calculated. Then the values of these parameters are set for working solutions before starting the sequencing.

The electric field at the interface "reading electrode—solution" determined by the superposition of the fields from the charges mentioned above: localized on the active segment of the negative charge DNA fragment the value of one electron charge, and the positive charge of the drifting proton, and can be represented by the expression:

$$E(x=0) = -\frac{q}{\varepsilon \cdot \varepsilon_o \cdot x_m^2} + \frac{q}{\varepsilon \cdot \varepsilon_o \cdot (x_m + \mu_p \cdot E \cdot t)^2}$$

Here μp is the proton mobility in the electrolyte, E is the superposition of the fields in the electrolyte near the reading electrode, t is the time, xm is the distance from the site of electron localization on the DNA fragment to the interface plane "electrode—solution" (x=0), ε is the dielectric constant of the solution, q is the elementary charge, E is the vacuum dielectric constant.

Over time, the field on the reading electrode tends to the maximum equal to:

$$E(t, x = 0) = -\frac{q}{4\cdot\pi\cdot\varepsilon\cdot\varepsilon_{om}\cdot x_m^2} + \frac{q}{4\cdot\pi\cdot\varepsilon\cdot\varepsilon_0\cdot(x_{om}+_m\mu_p\cdot E\cdot t)^2} \rightarrow -\frac{q}{4\cdot\pi\cdot\varepsilon\cdot\varepsilon\cdot x^2}\bigg|_{t\rightarrow\infty}$$

To determine whether a semiconductor sensor can register the result of the separation of one pair of charges the corresponding calculations were performed.

The cell parameters were estimated for the dimensions of the reading electrode (gate field-effect transistor) 30 nm×100 nm, for an aqueous solution with pH=7.5 concentration protons and ions (OH$^{-1}$) was taken equal to ~N (H$^+$)≈N (OH$^{-1}$)≈3.3×10$^{-10}$ mol/cm$^3$ (1 cm$^{-3}$ is N (H$^+$)=N (OH$^{-1}$)≅2×10$^{14}$ pieces), i.e. distance between them (ions hydroxyl groups and protons) in an aqueous solution $r_o$=(N$_{ion}$)$^{-1/3}$≈2×10$^{-5}$ cm=0.2 μm=2×10$^{-7}$ m; the diffusion coefficient of the proton in the aqueous solution is assumed to be D$_p$=9.3×10$^{-5}$ cm$^2$/V·s, the diffusion coefficient of the ion of the hydroxyl group is assumed to be D$_{OH}$=5×10$^{-5}$ cm$^2$/V*s; for the dielectric constant of the aqueous solution was taken to be 30.

Drift characteristics of protons and ions (OH$^-$) in aqueous solution (characteristic the shielding times of these charges) will be determined by the minimum electrical field E*=q/{[(Nion)$^{-1/3}$]$^2$*ε$_0$ε4π. The characteristic shielding time of these charges with the concentration of ions N ions in an aqueous solution was estimated as t*=[N(H$^+$)]$^{-1/3}$/(μSAE*), where $r_0$=[N(H)$^+$]$^{-1/3}$=[N(OH)]$^{-1/3}$—the average distance between mutually identical and mutually unlikely ions of hydroxyl groups (OH$^-$) and protons (H$^+$); the mobility of ions of hydroxyl groups (OH$^-$) and protons (H$^+$) was calculated and equal to p$_p$=3.54·10$^{-7}$ m$^2$/V*s, μ$_{OH}^-$=1.075·10$^{-7}$ m$^2$/V*s.

Estimated value of the minimum electric field E* from the drifting proton, which, interacting with negative ions of the solution, will determine the proton shielding time:

$$E*=q/\{[(N_{ion})^{-1/3}]^2\varepsilon_0\varepsilon 4\pi=(1.6\times 10^{-19})/\{[2\times 10^{-7}]^2\times 8.85\times 10^{-12}\times 30\times 4\times 3.14\}=1.1\times 10^3 V C/m$$

This is the minimum field (the field at the maximum distances between the proton and hydroxyl group), which will determine the proton shielding time.

For the case of the location of the active segment of the DNA fragment in the diffusion parts (but outside the undersurface part (the Helmholtz layer of the double layer)) of the double layer the estimated time of the potential of the reading electrode to saturation, which is determined by the proton drift velocity in the diffusion part of the double layer:

$$T_e>T_p=r_0/(\mu_p\cdot E)\approx(2\cdot 10^{-7}/3.54\cdot 10^{-7}\cdot 5\times 10^3)\approx 2\times 10^{-4}\,_{sec,where}E**\approx 5\times 10^3\,V/m$$

this is a lower bound; it is clear that the estimate of the time of proton shielding from above will be an order of magnitude less. It is also clear that if the time of proton shielding after its formation as a result of the separation of a pair of charges tends to zero, then it is questioned itself the possibility of an induced potential appearance on the reading electrode.

If we set the distance from the reading electrode to offset electrode, under negative potential, for example, 0.5 V, is equal to 1 mm, then the average value of the electric field in this gap will be 5 V/cm (or 500 V/m). Then the proton drift time in the external field can be estimated as:

$$T_2=(2\times_m)/(\mu_p E_{ext})=2\cdot 10^{-8}/(3.54\cdot 10^{-7}\cdot 500)\approx 10^{-4}\,sec$$

During this time, the proton leaves the charge separation site x$_m$ at a distance:

$$L(T_2)=\mu_p\cdot E*\cdot T_2=3.54\times 10^{-7}\times 500\times 10^{-4}=1.8\times 10^{-8}$$
m=18 nm Thus, the effect of the electric field of the drifting proton on the charge induction process on the reading electrode decreases over time over due to proton drift, and not due to its screening by mobile ions of water solution (hydroxyl groups, OH$^-$). Charge that induced on the capacity of the reading electrode is converted to potential that modulates the current in the channel field-effect transistor, which, in turn, can be read into an external circuit through charge-sensitive (electrometric) amplifier.

For a reading electrode with 30 nm×100 nm measurements, and a distance between the location of the electron on the DNA fragment after charge separation and the surface of the reading electrode at 20 nm, and the dielectric constant water solution equal to 30, for the capacity of the reading electrode we obtain the value C$_e$=4×10$^{-16}$ F. Note that the capacity of the good charge-sensitive (electrometric) amplifier has the value of C$_{in}$≈10$^{-15}$ F. With the specified cell parameters and taking into account the emerging capacitive divider, the value induced potential will be 4×10$^{-4}$ V, and the output voltage electrometric amplifier will be equal to 14.5×10$^{-6}$ V. Note that in solution with greater ionic strength, for the location of the localization of an electron on DNA fragment after charge separation in the diffusion part of the double layer, the distance between this place and the surface of the reading electrode is necessary will decrease, which will lead to a greater magnitude of the induced potential on the capacity of the reading electrode is less than 4×10$^{-4}$ V.

Evaluation of electrical noise at the accepted values of the parameters of the cell and the reaction mixture showed the following values:
shot noise current~3.5×10$^{-15}$ A,
thermal noise voltage~4.2 μV,
generation-recombination (GR) noise current~2.5·10$^{-17}$ A,
generation-recombination (GR) noise voltage~24 nV.

Thus, the results of the analysis and calculation of the values of electrophysical parameters of the physic-chemical processes accompanying the DNA fragment sequencing process in the cell confirms the possibility of recording the result of the separation of one pairs of charges that accompanies nucleotide incorporation by polymerase into DNA fragment being polymerized, and registration method and its circuit implementation are proposed also.

The specified dimensions of the reading electrode (transistor gate), design sensor, cell, analog-digital circuit of the cell, matrix of cells, matrix chip sensor cells as a whole can be implemented by means of industrial semiconductor technology, for example, using TSMC technology with technological standards for the transistor gate length 28 nm and less.

Example 3. Nanosized Sensor Based on Nanowire FET

Nanoscale sensor based on nanowire field effect transistor designed to record the results of splitting up pairs of charges near the sensor surface after each incorporation of nucleotides by polymerase into the polymerized DNA fragment in composition with the immobilized polymerase complex at the surface of the nanowire 44.

The block diagram of the nanowire transistor with immobilized triple complex is shown in FIG. 16, and consists of a planar thin film metal nanostructures deposited on the dielectric layer 49, covering substrate 45; thin film metal electrode nanostructure (contacts to the nanowire) 46 together with the metal channel-nanowire 50 is formed on a dielectric substrate by photo- and electron lithography with using photo- and electronic resist, also as with technology of etching exposed areas and technologies of metal sputtering by the magnetron or thermal method.

The control electrode can also serve as a conductive sublayer (for example, doped silicon), which is under the dielectric layer 49. In order to eliminate contact of the supply electrodes with the aqueous solution in the microfluidic cell they are covered with a thin layer of dielectric 51 applied through a mask. Also, by numbers 44, 47, 48 respectively, immobilized polymerase complex, an aqueous solution of the reaction mixture and the displacement electrode is shown.

The conductivity of the transistor channel depends on the electric field, in which the nanowire (NW) is located. Local field variations with sufficient magnitudes are also able to change the conductivity of the nanowire, which allows registering with such a local charge change device in nanowires, as well as accession to (or detachment from) the nanowire surface small charged particles.

Nanowire transistor can be implemented on the basis of SOI technology. SOI material (silicon on an insulator) is a monocrystalline layer silicon, separated from the silicon substrate by a layer of silicon oxide. In this top silicon layer the nanostructures of various configurations can be formed. Using SOI material the suspended NW can be made. First by the lithography the NW structure is formed in the upper silicon layer. Then the sample is placed in a solution of hydrofluoric acid. As a result, located under the NW $SiO_2$ layer is eliminated. In this case, wide areas of silicon serve as a mask for etching $SiO_2$, and thin wire is suspended due to the "underfill" under it, due to isotropy of the etching process of $SiO_2$.

Due to the large area of the supply electrodes (several $mm^2$) current leakage through the dielectric layer of the SOI plate became significant (more than 10 pA) and for its blocking the thickening of the dielectric layer in two successive deposition of $SiO_2$ with a thickness of 200 nm over the entire surface of the chip, except the central region 80×80 $\mu m^2$ with nanostructures was produced (in FIGS. 20 and 21, the border of the additional insulating layer is visible). As a result of the improvement the leakage from the substrate to the contact pads almost disappeared when the applied voltage up to 10 V.

After thickening the dielectric layer by the methods of photolithography and magnetron sputtering a large-sized part of the structure containing feed Ti electrodes with a thickness of 100-160 nm was formed. As a gate electrode the lower layer of silicon (substrate) was used.

At the final stage of production for measurements in liquid environment to isolate all open conductive surfaces of the transistor structure by sputtering a 200 nm thick $SiO_2$ layer was used. Insulation layer covered Ti electrodes and most of the area of the silicon contact pads, leaving open channel-nanowire transistor. FIG. 21 shows the final view of the formed structures of nanowire transistors in the central area of the chip.

Depending on the technological requirements, the NW geometry in the transistor may be implemented in various forms, for example, in linear or in V-shaped.

The conductivity of the p-type semiconductor channel is determined by the expression:

$$\sigma \approx q\mu_p p_{p0}$$

where p is the hole mobility. Sensor sensitivity can be characterized the dimensionless parameter p, $$\frac{\Delta\sigma}{\sigma} = \frac{q\mu_p \Delta p_p}{q\mu_p p_{p0}}$$

where p is the modulation of the hole concentration due to potential change.

This parameter corresponds to the volume ratio between that part of the nanowire, where the concentration is effectively modulated by the electrical potential, and the rest volume. It can be seen that it will be maximized when the Debye shielding length in the semiconductor is much larger than $$\frac{\Delta\sigma}{\sigma} = \frac{p_{p0}\left(e^{-\frac{q\Delta\varphi}{k_B T}} - 1\right)}{p_{p0}} \approx -\frac{q}{k_B T}\Delta\varphi$$

the nanowire radius $\lambda_D \gg R$. This parameter can be present explicitly:

where $\Delta\varphi$ corresponds to the change in potential in the nanowire, which is described function above, and thus it is possible to obtain an estimate of the maximum sensor sensitivity on a nanowire field-effect transistor.

FIG. 17 shows the calculated electrical potential distribution for the case of a single particle carrying a unit charge. FIG. 17A shows the distribution potential on the z=φ (x, y) plane perpendicular to the nanowire axis, with the beginning coordinates in the center of the nanowire. Values of potential near a charged particle not shown, because in this area the potential tends to infinity. FIG. 17B shows a graph of equipotential lines; in the center of closed curves the charged particle is placed; the dotted line shows the nanowire boundary.

The potential distribution profile along the axis connecting the center of the nanowire with the center of the particle is shown in FIG. 18. Calculations are made for the following parameters:

the particle is located at a distance of h=6 nm from the nanowire, whose radius is R=50 nm. Debye shielding length in electrolyte $K_D$=10 HM (ion concentration, C=1 mM), impurity concentration in p-doped silicon channel $N_A = 10^{+15}$ $cm^{-3}$.

The potential distribution is represented along the axis connecting the center of the nanowire with the center of a charged particle, and normalized to the value of the potential on the surface nanowires from the particle.

Figure 3A:
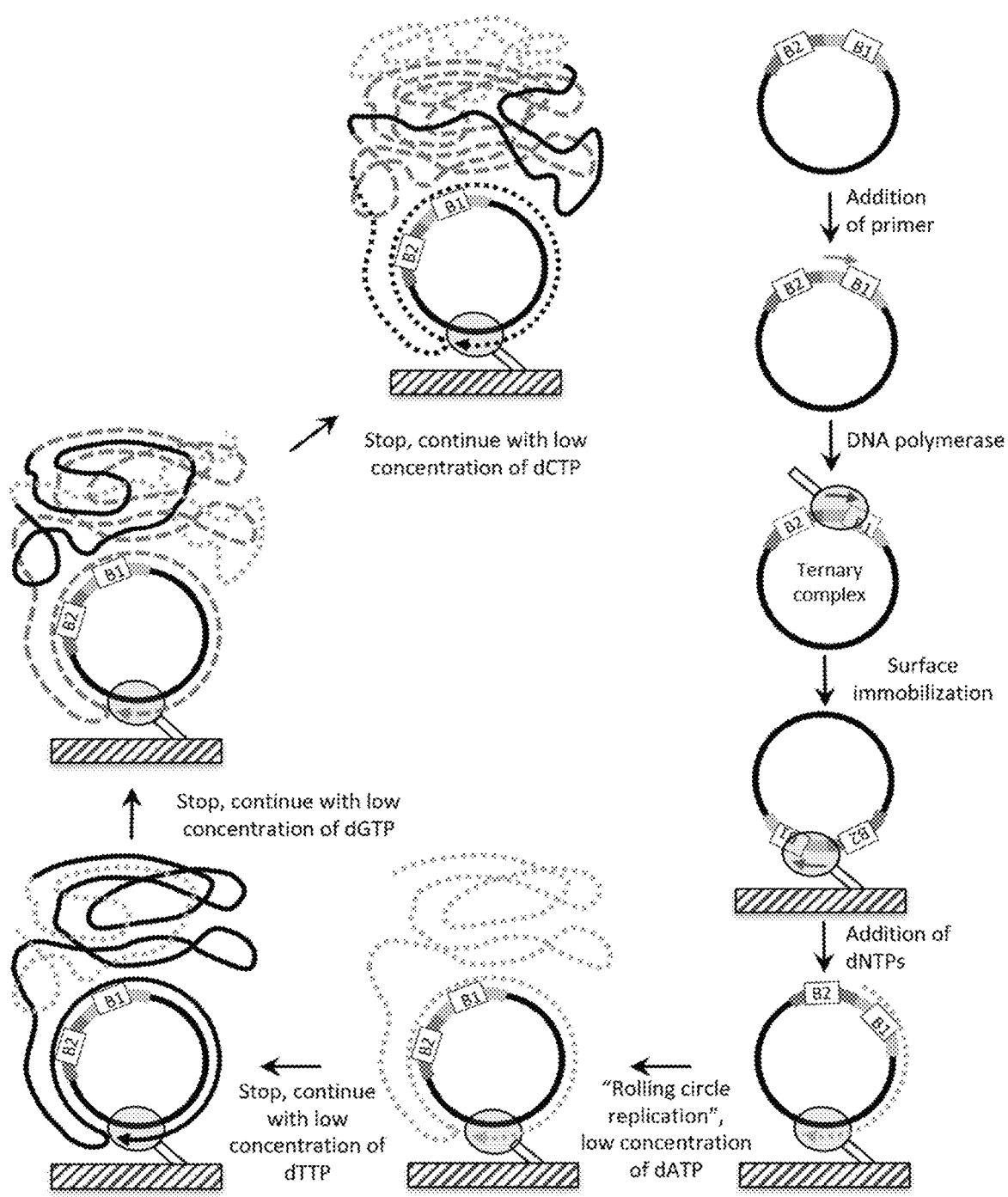
FIG. 3A is a schematic representation of the sequence of steps in the sequencing procedure of the preferred embodiments of the invention; serial sequencing procedure: the sequential addition four reaction mixtures of nucleoside triphosphates, wherein each of the mixtures has one type of nucleoside triphosphates in a concentration limiting synthesis rate.
Figure 3B:
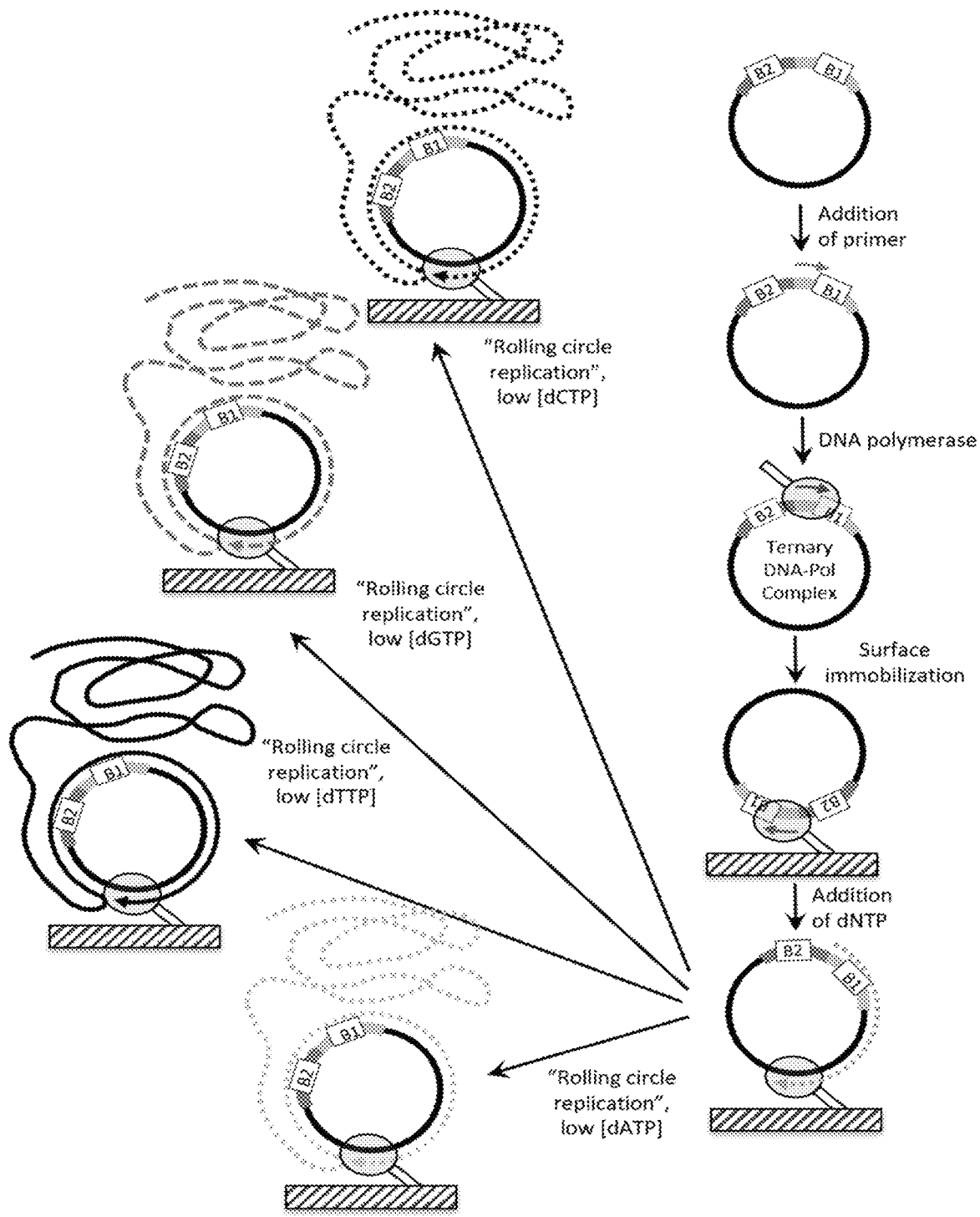
FIG. 3B is a schematic representation of the sequence of steps in the sequencing procedure of the preferred embodiments of the invention; parallel sequencing procedure: a preliminary separation of complexes comprising four parts, their immobilization on the surface of the four sensor cell arrays, followed by the asynchronous addition of one of four different nucleoside triphosphates reaction mixtures on the surface of the cell array of each of the four chips.
Figure 4:
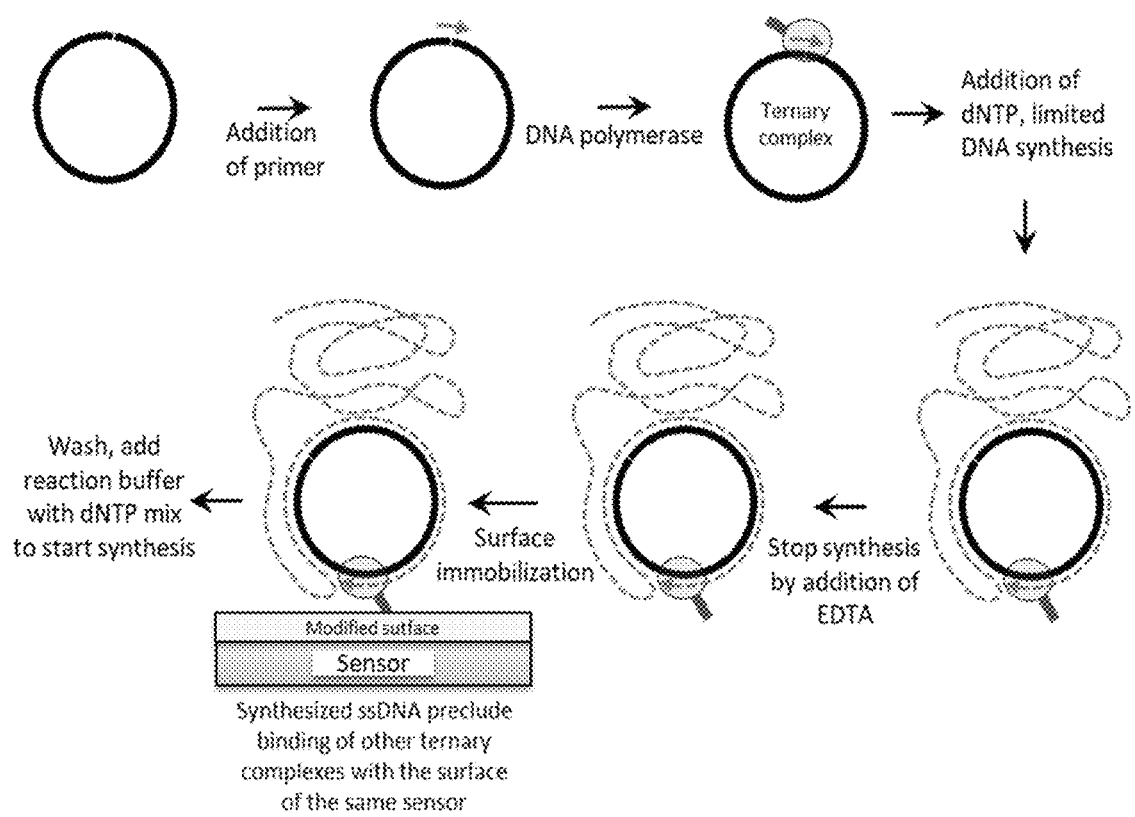
FIG. 4 schematically shows a variant of the procedure of immobilization of single polymerase complex on the surface of the sensor, the start and stop of polymerization of circularized nucleic acid fragment.

In the case of the detection of individual charged objects, the field of a single electron penetrates deep into the nanowire and is able to completely "pinch" the conductive channel due to the smallness of the transverse dimensions of the semiconductor nanowire, as shown in FIG. 3d in the article [J. Saifi, et al. Direct observation of single-charge detection capability of nanowire field-effect transistors//Nature Nanotechnology. 2010. —September Vol. 5, no. 10. P. 737-741]. Sensitivity of the sensor in this mode can be extremely high. In the article shows that in the case of detection with the help of a nanowire of single electrons located in charge traps on the surface of a specially prepared sample, charge sensitivity reaches a value of $4*10^{-5}$ e/√Hz at cryogenic temperatures. At room temperatures in [Denis E. Presnov, et al. A highly pH-sensitive nanowire field-effect transistor based on silicon on insulator/Beilstein J. Nanotechnol. 2013, 4, 330-335] the limiting charge sensitivity of the nanowire transistor was estimated as $5*10^{-3}$ e/√Hz.

The design features of the device can significantly simplify the method of its manufacturing, avoiding time-consuming and complex processes of alloying and annealing, required for the formation of ohmic contacts to the silicon regions of the drain and the source of the transistor. The capabilities of the applied SOI material also allow to form a suspended nanowire channel, partially removing the $SiO_2$ sublayer, which is a source of charge fluctuations that increase their own noise transistor. A transistor with a suspended nanowire channel will have greater sensitivity both by reducing its own noise and by increasing the working surface of the nanowire.

Individual nanowire transistors can be placed in an integrated structure, which is a microcircuit with an array of nanowire transistors with an address bus that allows for individual measurement on each nano transistor, as shown in FIG. 19.

Example 4. Nanoscale Sensor Based on a Single-Electron Transistor Designed to Generate a Signal from the Result of the Splitting Up of a Pair of Charges in After Incorporation Each of Nucleotide by Polymerase in a Polymerizing DNA Fragment A electronic nanostructure consisting of two ultra-small tunnel junctions connected in series C1 and C2, between which is located an electrode (island), connected to the control electrode (gate) through a capacitor Cg, as shown below FIG. 22, is called a Single-electron transistor.

The current-voltage characteristic of the device shown in figure FIG. 23A. This device has a characteristic region Coulomb blockade (solid line) at voltages ½V½<$V_{off}$=e/Cs ($C_S$—the total capacitance of the transistor island) and zero voltage at the control electrode when the electron tunneling not occurs because of the adverse energy such a process.

At voltages $V_g$ at the gate electrode, corresponding to $C_0V_g=Q_g$=e/2+ne tunneling is possible at any V in which case the current-voltage characteristic of the transistor has not region Coulomb blockade (dashed line). In this connection, the dependence of the transistor current I (V=const) the magnitude of the polarization charge $Q_g$ on to the central island, called modulation characteristic has the form of a periodic function with a period of one electron charge e, i.e. I ($Q_0$+e)=I ($Q_0$) (FIG. 26). The process of correlated electron tunneling at voltages of the order of V and less is characterized by the fact that electrons come and go from the island of the transistor one after another. For this reason, the transistor is called one-electron.

In order for single-electron effects to be clearly distinguishable against the background of thermal and quantum fluctuations, the characteristic values for the electrostatic (Coulomb) energy of the system ($e^2/2C_S$) must significantly exceed the values of the energies characteristic of thermal (kT) and quantum (~1/τ, where τ=RC) fluctuations, i.e. the following conditions must be met:

$$\frac{e^2}{2C_\Sigma} \gg kT, R \gg R_q = \frac{\pi\hbar}{2e^2} \cong 6.5 \text{ kOhm} \qquad (1)$$

wherein $R_q$ quantum resistance, R—resistance tunnel junctions.

Single-electron transistor is characterized by extremely high sensitivity to a change in the charge on the central island. Even a slight change in the charge dQ islands, which may be substantially less than the electron charge e, leads to a noticeable change dI transistor current (see. FIG. 23B) and can be registered. This property is a single-electron transistor can be used as a unique electrometer with subelectronic sensitivity.

As follows from formula (1), the characteristic dimensions of the elements of single-electron devices, which determine their capacity, directly affect the operating temperature of the devices. Evaluating the characteristic values of the capacitances and sizes of tunnel junctions necessary for normal operation of single-electron devices at room temperature T=300 K using this formula, we obtain the capacitance $C=10^{-18}$–$10^{-19}$ F and, accordingly, dimensions on the order of nanometers. Such a single-electron transistor can be created by using as an "island" single molecule. This is the basis of model molecular single-electronics.

The minimum value of the noise level in the single-electron transistor, and consequently, the maximum sensitivity is achieved when the bias voltage V, slightly above threshold Voff Coulomb blockade. In addition, minimum noise is a function of the measured charge Qx.

In addition to optimizing parameters of the transistor and its operation modes, obtained expression for estimating the maximum sensitivity of the single-electron transistor at the low-frequency fluctuations registered transistor current. In cases where the own capacitance of the signal source at zero voltage of the capacitance equal Cs, a measured charge Qx, as shown in the equivalent circuit diagram of a single-electron transistor, FIG. 24, the maximum sensitivity estimate of a single-electron transistor can be represented by the expression:

$$(\delta Q_x)_{min} \cong \frac{\sqrt{S_I(0)\Delta f}}{(dI/dQ)}\left(1 + \frac{C_s}{C_g}\right), \qquad (2)$$

where S I (0)—spectral density fluctuations of tunneling current at low frequencies. The magnitude of the measured charge is determined by fluctuations of the number of tunnels events in each of transistor transitions.

In the case of classical noise, the result (2) is simplified when the intrinsic capacitance of the charge source Cs is small, and the resistance and capacitance of its transitions are the same (C=C1=C2, R=R1=R2):

$$(\delta Q_x)_{min} \cong 5.4 C\sqrt{kTR\Delta f} \qquad (3)$$

Equation (2) takes a simple form in the case of a large signal source capacitance $C_s$, when the charge source convenient $$\delta V_x = \delta Q_x/C_s$$

described as a voltage source—):

$$(\delta V_x)_{min} \cong 2.7\sqrt{kTR\Delta f},$$

where R=min (R1, R2).

As can be seen from the formulas (3) and (4), transistor noise decreases with decreasing temperature and resistance transition, but at T=0, play a significant role is the quantum fluctuations are not represented by the formula (2). Evaluation of absolute minimum quantum noise gives:

$$(\delta Q_x)_{min} \cong \sqrt{\hbar C_\Sigma \Delta f \frac{R_q}{R}} \quad (5)$$

There are at least two ways to reduce the quantum noise in the single-electron transistor. One way—selection operating point transistor close to e/2, when V~Vt (where Vt—modulated Coulomb blockade threshold), in this case, the probability sotunneling decreases with decreasing Vt, so that the contribution of the quantum noise is minimal. Sotunneling called quantum transition of an electron from one outer electrode to the other through the virtual intermediate and energetically unfavorable state charged transistor island). The second method—use of a highly asymmetric single-electron transistor (R1>>R2). Classic noise in the transistor depends primarily on the smaller of the resistances, thus increasing the second resistance is not essential. However, so-tunneling time is proportional to 1/R1R2, and accordingly, it decreases with an increase of more resistances. Note that, in one of the slopes of the modulation characteristic of an asymmetric transistor increases the value of the derivative $dI/dQ_g$, which leads to an increase in the output signal.

The spectrum noise of the single-electron transistor has a pronounced component of 1/f. The experimental values of noise planar geometry transistors are of the value $$10^{-3} \div 10^{-4} e/\sqrt{Hz}$$

at a frequency f=10 Hz [Wei Lu, Zhongqing Ji, Loren Pfeiffer, K W West & A J Rimberg, Real-time detection of electron tunneling in a quantum dot, Nature, V. 423, 2003, PP 422-425.].

Numerous experiments have shown that the limiting characteristics of single-electron devices determined by level the fluctuations of the polarization background charge, which at low frequencies dominate their natural components.

In most cases, excessive noise in the single-electron transistor is the charge nature. It is shown that the output noise level in the single-electron transistor is dependent on the operating point (i.e. from the transform coefficient dI/dQs), moreover, value of the noise is maximal at the maximum value of the derivative. At the same time, when converted into charge units noise level is approximately the same for all operating points. This indicates that recorded excessive noise is the nature of charge, i.e. output noise of transistor is a reaction transistor to the charge fluctuations in its immediate surroundings.

One of the manifestations noise of charges background is telegraphic noise of current with random switching between two, three or more levels that have an equivalent jump value of up to 0.2e. Telegraph noise is a type of noise that often manifests itself in single-electron structures. His observation and study allowed to conclude that the nature of the excess noise associated with the combined influence of the charge duplex fluctuations, distributed in large numbers in the thickness of the dielectric surrounding the transistor island and is apparently associated with the imperfection structure of this environment.

The task of creating a molecular transistor is divided into two sub-tasks. The first—the creation of electrodes nano-gap between them, which would allow to explore nanometer-sized objects. The second—the room and fixing of a single molecule between these electrodes.

Nano-gap may be formed in various ways:
a method of "mechanically controlled break nanowires", "advanced" e-beam lithography,
electrochemical methods, such as deposition of metal to a preformed gap or gap creation by etching:
electromigration,
ablation lithography by transmission electron microscope, ion-beam lithography,
a method that uses molecular beam epitaxy.

FIG. 25 is a schematic representation monomolecular transistor having pendant electrodes: M—molecule deposited in the gap and fixed there by means of SH-groups.

FIG. 26 shows a photograph of the SOI structure with hanging electrodes above the substrate.

FIG. 27 shows a photograph of the nanostructure with a single-electron transistor nano-gap is prepared by electron-beam lithography.

FIG. 28 shows a photograph nano-gap obtained by electromigration (elektrotrepping).

FIG. 29 shows a photograph nano-gap obtained by ion-beam lithography (FIB-technology).

FIG. 30 shows a photograph of the nanostructure made of 16 cells transistors with nano-gaps.

FIG. 31 shows a photograph of one of the 16 cells on the basis of a transistor with nano-gap.

FIG. 32 shows a photograph of the center electrode formed in the island-structure of the single-electron transistor nanowires.

FIG. 33 shows a photograph of fabricated nano-gap for creating a molecular single-electron transistor.

FIG. 34 shows the current-voltage characteristic of the transistor structure with nano-gap; form leakage current shows that nano-gap has formed.

To date, single-electron transistors have a maximum sensitivity of the charge. Known publications describing single-electron transistor circuit for detecting single molecules, e.g., streptavidin [Nakajima, A.; Kudo, T.; Furuse, S. Biomolecule detection based on Si single electron transistors for practical use. Appl. Phys. Lett. 2013, 103.].

Example 5. Nanosized Sensor Circuit with the Stochastic Resonance

Optionally, to increase the signal level to noise level in the chip matrix cell circuit diagram can be added, which implements a stochastic resonance mode consists of the semiconductor element (or element groups) having a transfer characteristic or the current-voltage characteristic with the area bistability comprising a bias circuit (reference operating point) at the constant current containing noise source (generator) comprising generating circuit of output signal. Scheme stochastic resonance is realized by connecting the signal source and the bias circuit (reference operating point) at the constant current noise source (generator) to the input of the semiconductor element (device or group of elements) that realizes the transfer characteristic or the current-voltage characteristic with bistability region and connection the output of the semiconductor element (device or group of elements) that realizes the transfer characteristic or the current-voltage characteristic of a region bistability, to the input of the cell circuit, wherein an output digital signal is formed.

The case of embodiment of the sensor cell, utilizing stochastic resonance to detect separation facts of charges is illustrated in FIG. 15. The circuit includes a FET cell sensor, polymerase molecule in the complex 38 is immobilized on the gate, a bipolar transistor V1, as well as voltage sources U0 (bias voltage), $U_{sup}$ (supply voltage for sensor circuit) and UN (noise voltage). The output signal is taken from $U_{out}$ contacts.

A FET cell sensor and a bipolar transistor V1 together form a Schmitt trigger, which implements S-shaped transfer characteristic $U_{out}=F(U_{in})$ $U_{in}$ herein means the potential difference between the circuit ground and the gate of the FET. S-shaped transfer characteristic in the circuit formed by the presence of positive voltage loop realized by supplying the amplified signal from the drain of the FET (p$^+$— drain in FIG. 15) to the base of a bipolar transistor V1 through the circuit of the resistive divider R5-R4, and the amplified signal at the source of the FET circuit (p$^+$—source in FIG. 15) through a common resistor R3. Scheme parameters (type and characteristics of the transistor V1 and the values of resistors R1-R5) are selected in a such way for providing the appearance of bistability characteristic transfer circuit [1]. When the input signal $R_{in}$ circuit U is defined as the sum of the noise signal UN and the signal, i.e. potential induced on the gate of the FET, as described in "DETAILED DESCRIPTION OF THE INVENTION" section. The joint action of the voltage signal induced at the gate of the FET and the noise signal by the action of the latter is changed (modulated), the probability of finding a Schmitt trigger circuit between two stable states within the bistable region of the transfer characteristic. This leads to the appearance at the circuit output (voltage $U_{out}$) voltage pulses at timings when the potential is induced on the FET gate. Parameters (distribution statistics, variance) UN noise signal is set in such a way as to ensure that the stochastic resonance mode described above [2-5], i.e. that occurred in the circuit amplification ratio "signal to noise", which is manifested in the form of voltage pulses on the output of the circuit. Thus, the sensor circuit, without providing any amplification of the useful signal voltage at the same time increases the ratio of "signal to noise" that makes a weak useful signal available for further processing.

In any device forming voltage UN noise with desired characteristics may be used as the noise source. As examples of such sources (but not limited to) may be considered various circuits in the shift registers, including analog-to-digital conversion on the output of the noise generator by thermal or breakdown sources (enhanced thermal current noise through a resistance or noise breakdown current back biased pn-junction, etc.).

The signal from the output circuit based on stochastic resonance effect is applied for further amplification, normalization and conversion to digital form. FIG. 15 shows how for these purposes $U_{out}$ signal is supplied to an integrator (low pass filter) Yi1, and then—by a normalizing amplifier Yi2 and comparator Yi3, from the output of which formed pulses are applied to D-flip-flop Yi4. From the output of D-flip-flop in time sampled digital signal DATA is supplied to the matrix circuit corresponding to a data bus for further transfer to the computer. The above sensor circuit on the basis of stochastic resonance can be used similarly for the circuit of FIG. 14, a two-channel version that will be subtracted from the signal level of the background potential of the working solution.

Example 6. The Formation of Primary Signals and their Transformation into a Nucleotide Sequence of DNA the Fragment that is Sequenced FIG. 5 shows the main steps of forming and converting data of the nucleotide sequence of the DNA fragment of the following composition: AACGTCTTCAGGGCTAGCACCAT (SEQ ID NO: 5).

Figure 5A:
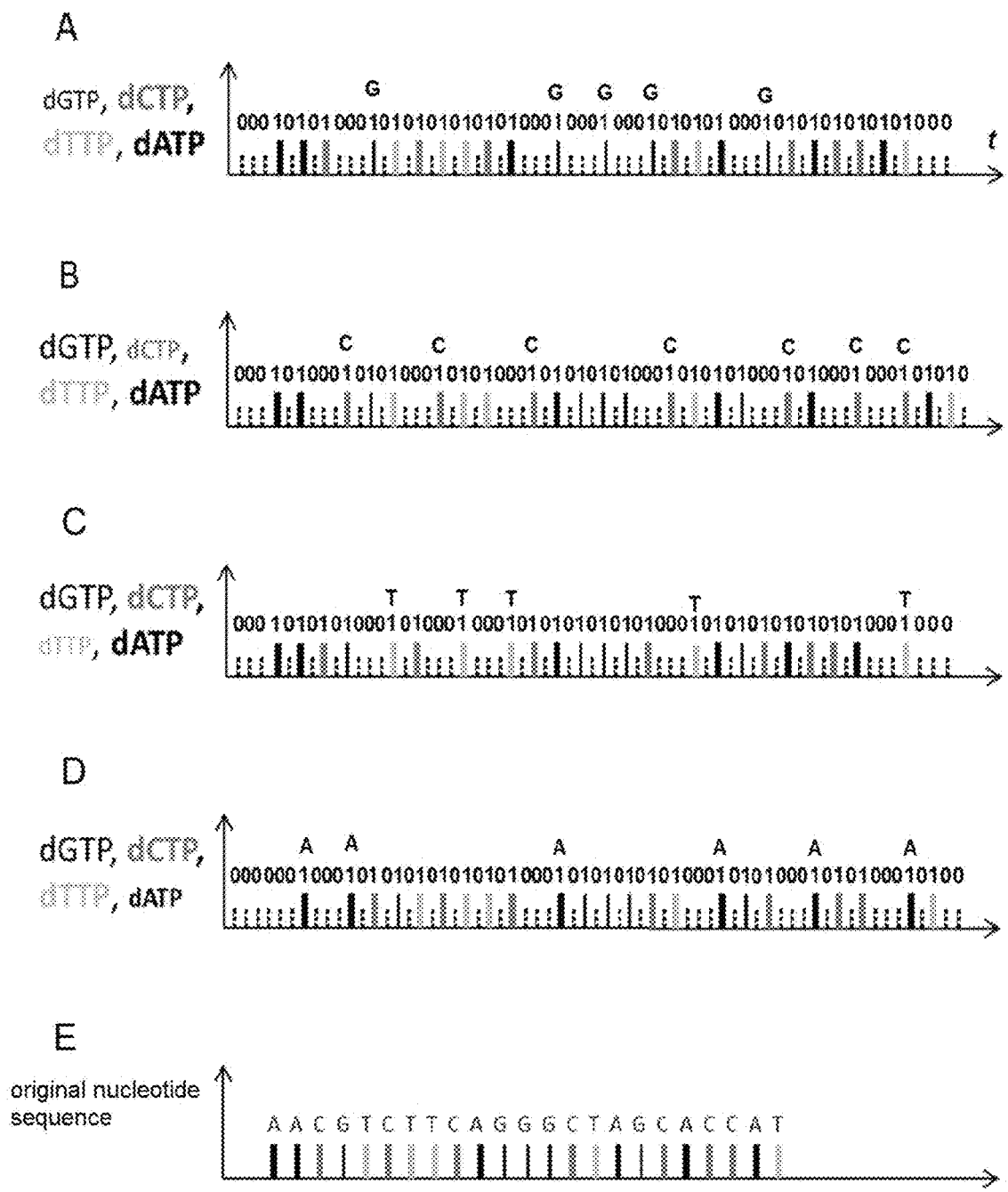
FIG. 5A shows the time sequence of discrete time intervals for the serial sequencing apparatus with one microchip, which are formed by cell microcircuit as a result of the polymerization of the same DNA fragment as a part of the complex sequentially in four reaction mixtures each containing reduced concentrations of nucleotides of only one type, name of which is written in a smaller font next to Y axis; logical ones "1" mark the time intervals at which the sensor cell registered the events of charge separation during the reaction.
Figure 5B:
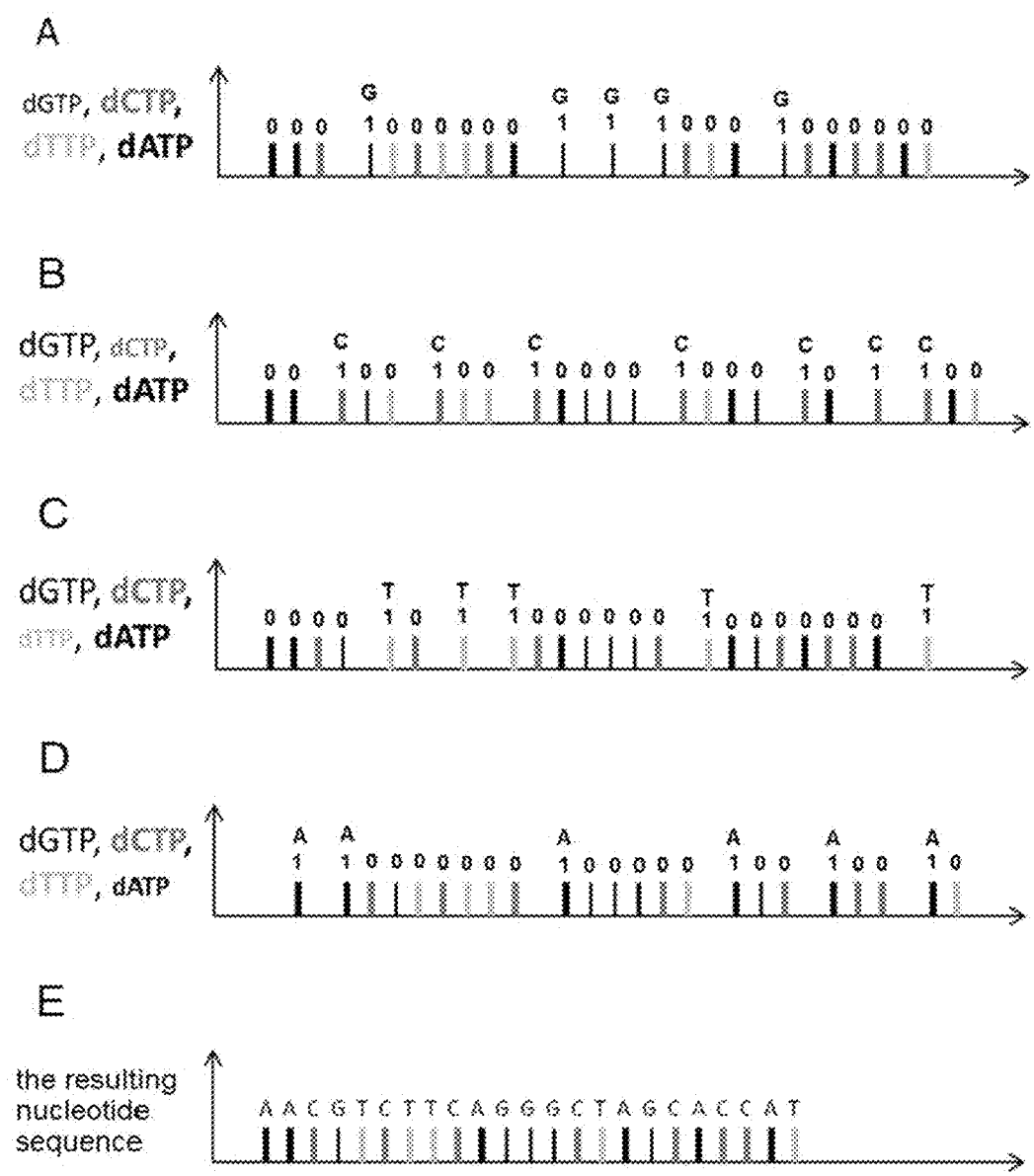
FIG. 5B is a diagram of formation of the resulting nucleotide sequence of the fragment from the 4 sequences, each obtained in the previous data processing step (see FIG. 5A).

Analog to digital cell circuit generates a temporal sequence of discrete time intervals, each of which denotes a logical "1" unit or logical "0" unit, moreover, the logical unit "1" denotes those intervals the time when the sensor of the cell registered the fact of splitting up of one pair of charges, accompanying the embedding nucleotide by polymerase in the DNA fragment polymerizing, and was formed the corresponding signal. If the polymerization of the specified DNA fragment as part of a complex immobilized on the surface of the cell sensor is carried out sequentially in four different reaction mixtures, characterized in that in each of them the concentration of nucleotides of only one species is reduced, and in each mixture this species different from similar kind in other mixtures, then the cell circuit will consistently form four time sequences, which (four above) are shown in FIG. 5A. It can see that on each time sequence the number of discrete time intervals indicated by the logical zero "0" is different before each interval indicated by the logical unit "1"; conventionally, we can talk about short and long-time intervals before the incorporation of nucleotides. These time sequences in real time (i.e., during their formation) are transmitted to a computer in which the special software reads, adds, compares and analyzes the length of time intervals prior to insertion of each nucleotide, i.e. It determines the number of discrete time intervals, the designated logical zero "0" before each time interval designated by the logical unit of "1". According to the algorithm sequencing, long (in average) time intervals are observed before the incorporation of nucleotides species whose concentration has been lowered against the normal concentration of the other three types of nucleotides in the reaction mixture. Since at the stage of sample preparation the name of the kind of nucleotides is known, the concentration of which is reduced for each reaction mixture, then at the first stage of data conversion the computer program converts each time sequence into a sequence of logical units "1" and logical zeros "0"; and now the logical unit "1" indicates each long interval of time corresponding to the embedding of nucleotides of the species, the concentration of which has been lowered in the corresponding reaction mixture and is known, now the logical zero "0" denotes short time intervals corresponding to the embedding of nucleotides of species whose concentration was normal in the same reaction mixture. The thus obtained sequence of logical units "1" and logic zeros "0" are shown in FIG. 5B. In the next stage of data conversion, the computer program compares the data on locations of nucleotides known species on each of four consecutive logical units "1" and zeros, "0" to each other, and by process of elimination, following the rule that at one position in the nucleotide fragment sequences DNA nucleotide can be disposed of only one type, —forming the resultant nucleotide sequence of the sequencing fragment DNA: AACGTCTTCAGGGCTAGCACCAT. In the next stage of data conversion, the computer program compares the data on the locations of nucleotides of known species on each of the four sequences of logical units "1" and zeros "0" with each other, and use the method of exception, following the Rule that in one position in the nucleotide fragments of the DNA the nucleotide can be located only of one kind, the resulting nucleotide sequence of the DNA is formed: AACGTCTCAGGGCACCAT.

Example 7. The Block Diagram of the Microcircuit of the Sensor Cells Array

Figure 10:
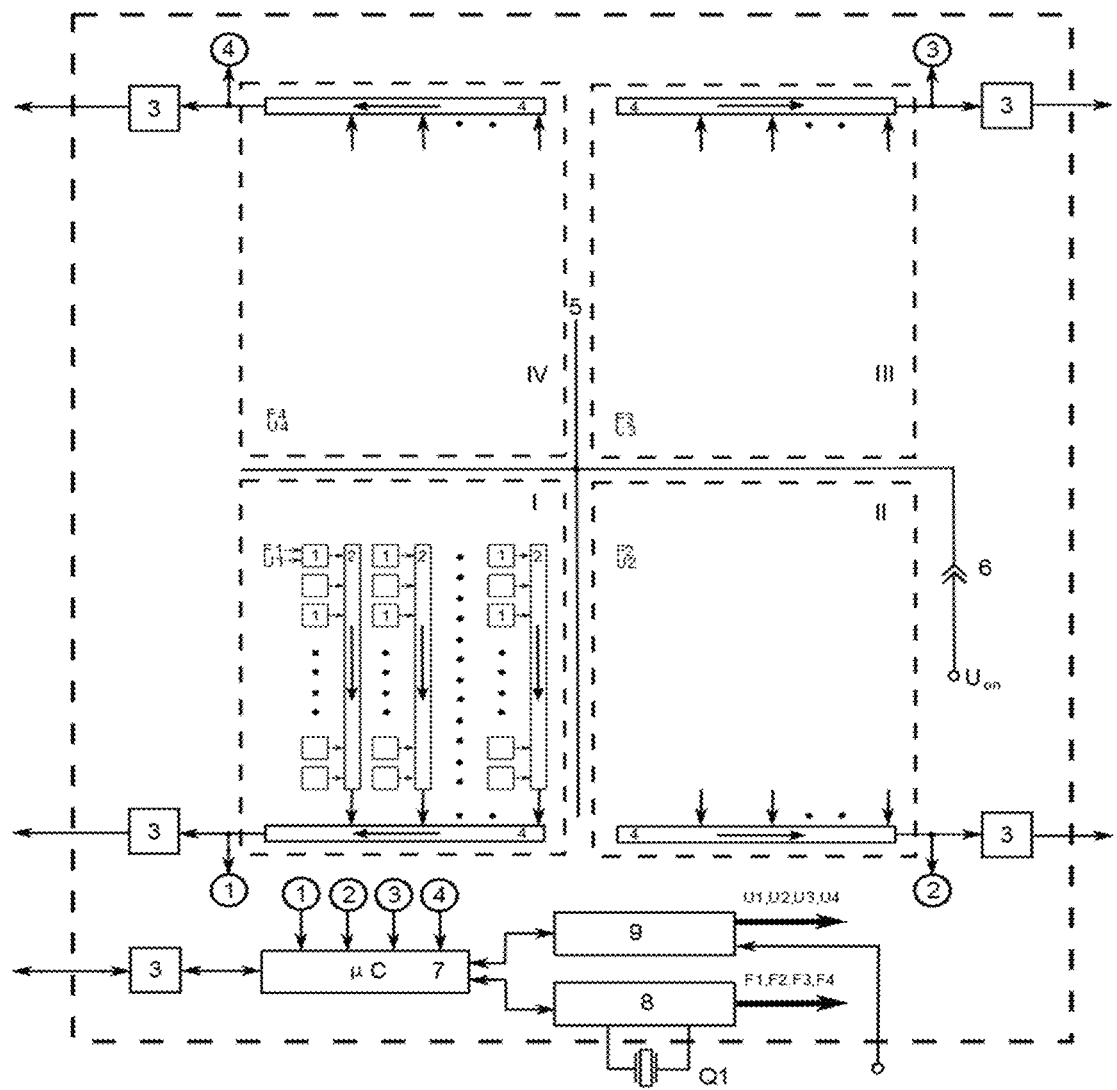
FIG. 10 is a block diagram of the sensor chip matrix cells of one embodiment. Roman numbers I, II, III, IV—denote section of matrix cells, each, e.g., size of 2000×2000 cells; numbers 1, 2, 3, 4 in the circles denote the outputs of the horizontal shift registers outputting digital data from cells arranged respectively in the sections I, II, III, IV. The numbers in the rectangular (square) shape: 1—cell of sensor; 2—vertical shift register is transferring the digital data from the cells of sensors of the matrix sections; 3—USB data interface between a computer and the IC; 4—horizontal shift register is transferring digital data from cells of vertical shift registers to USB data interface; 5—electrode offset potential set at which the voltage source, which is regulated by the controller; 6—connector between voltage source circuits and bias electrode, which is located on the lid chip; 7—controller operation mode control circuits; 8—adjustment clock generator, which is connected outside the chip quartz resonator; 9—regulated secondary power supply.

The block diagram of the microcircuit of the sensor cells array is shown in FIG. 10. The integrated microcircuit is intended for use as part of a device that implements a single-molecule nucleic acid sequencing method. The microcircuit of the sensor cells array can comprise, for example, 16000000 sensor cells that are arranged in a matrix with the number of columns and rows of 4000×4000 is divided into four sections; a block circuit diagram presented below. Roman numbers I, II, III, IV—is designated section of sensor cells matrix, each, e.g., size of 2000×2000 cells; numbers 1, 2, 3, 4 in the circles denote the outputs of the horizontal shift registers outputting digital data from cells arranged respectively in the sections I, II, III, IV. The numbers in the rectangular (square) shape: 1—sensor cell; 2—vertical shift register transferring the digital data from the sensor cells of the matrix sections arranged in a row; 3—USB data interface between a computer and the IC; 4—horizontal shift register of digital data transfer from vertical shift registers of one section of the matrix of sensor cells; 5—the bias electrode, the potential of which is set by the voltage source, which is controlled by the controller; 6—connector between voltage source of microcircuits and bias electrode, which is located on the lid chip; 7—controller operation modes of operation of microcircuit; 8—adjustable oscillator clock of frequency, to which is connected from the outside of the chip quartz resonator; 9—regulated secondary power supply.

The information output circuit from the array cells is functionally organized similarly to the information output circuit in a CCD with horizontal charge transfer. The output state of the D-trigger of the digital circuit of each cell located in the matrix column is rewritten into a vertical shift register intended for transferring logical data ("1" or "0") to a horizontal shift register, from which data via the USB interface are transferred to the computer. The microcircuit controller provides data exchange with a personal computer via USB interface, provides data analysis from each output cell array register, on the basis of which it controls the frequency of clock pulses and the voltage value that ensures the operation of the electrical circuitry of each. Through the USB interface microcircuit of the cells array receives supply voltage 5 V. Supply voltage can be supplied to the chip from an independent power source, such as from a battery. Pre-installed on the computer a special driver that provides coordination with the personal computer at the level of the software operation of the controller microcircuit of the cells array. This driver provides the primary parameter setting circuit of the cells array, operational management and operation of data exchange between the microcircuit and the computer. Due to the high data rate interface is used with high capacity, for example, USB 2.0 (400 Mbps).

Example 8. A Numerical Experiment to Determine the Quality of Time Delays Before Embedding Nucleotides in the Reactions of DNA Polymerization in the Sequencing Process by the Proposed Method Numerical experiments to determine the time delays before to embedding of nucleotides during DNA polymerization reaction for different concentration ratios of nucleotides of 4 kinds were performed based on cellular automata [Margolus N., T. Toffoli machines cellular automata: Trans. from English. —M: Mir, 1991. 280 s; Margolus, N., Physics-like models of computation, Physica D 10, 8195 (1984)] using the developed kinetic model the diffusion process in a DNA polymerization reaction [Manturov A O, Grigoryev A V, DNA SEQUENCING BY SYNTHESIS BASED ON ELONGATION DELAY DETECTION, Progress in Biomedical Optics and Imaging—Proceedings of SPIE Optical Technologies in Biophysics and Medicine XVI; Laser Physics and Photonics XVI; and Computational Biophysics. 2014. pp 94481T].

Figure 7:
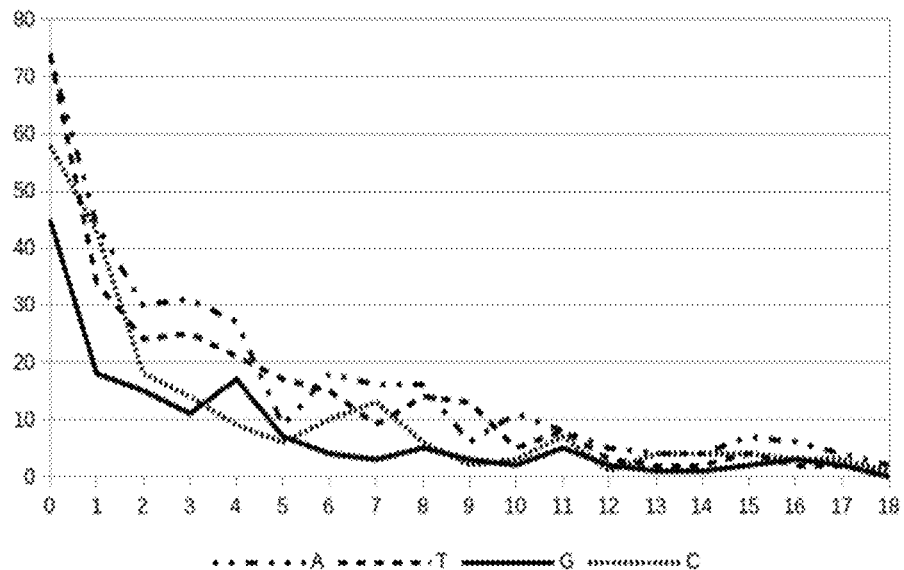
FIG. 7 shows the distribution of time delays for each type of nucleotide. By X-axis—the extent of delay in units of time, Y axis—the number of delays determined on the axis X durations obtained by numerical experiments. Shows the situation when the concentration of each type of nucleotide in the reaction mixture is the same.
Figure 8:
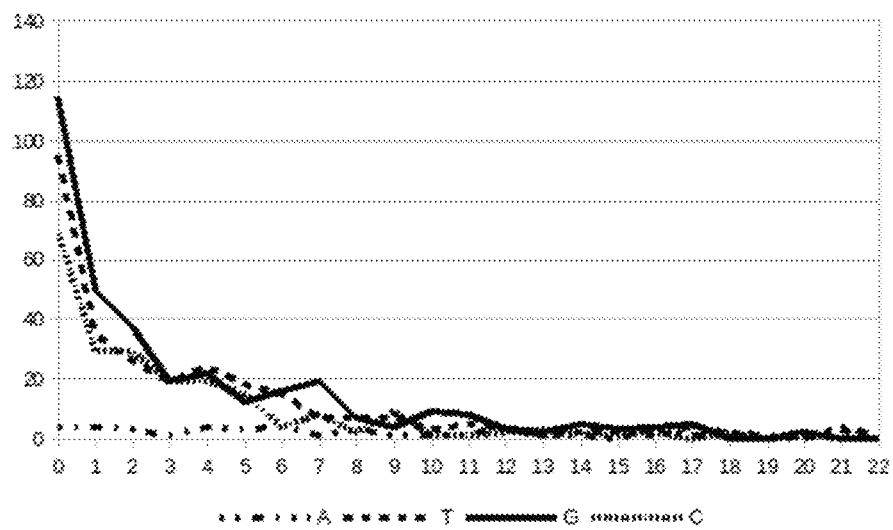
FIG. 8 shows the distribution of time delays for each type of nucleotides (for X axis—the extent of delay in units of time, Y axis—number of delays determined on axis X durations) provided 100-fold decrease of the concentration of one type of nucleotides, —type A nucleotide in the reaction mixture.
Figure 9A:
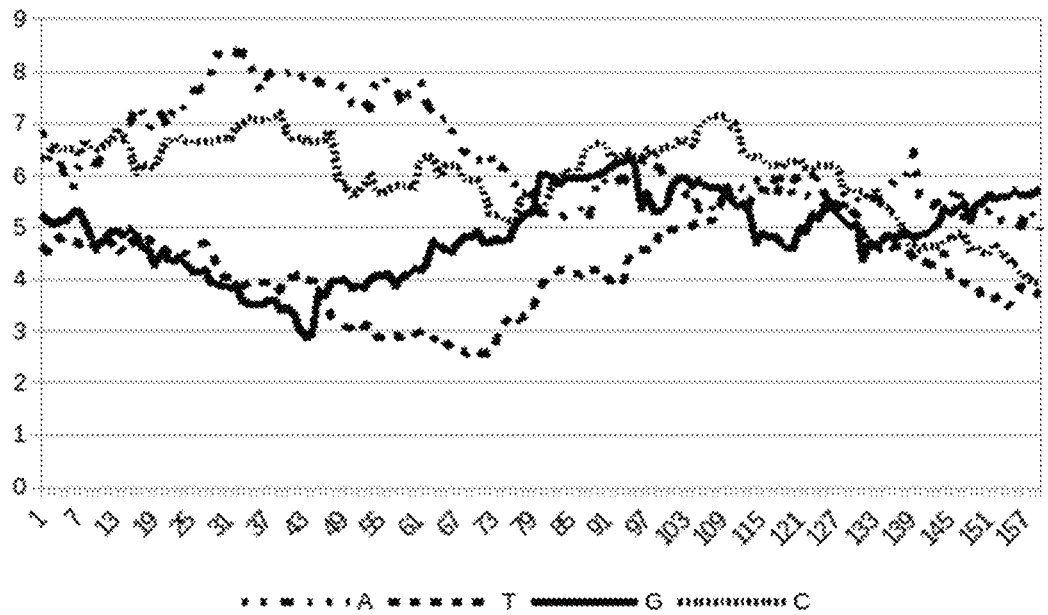
FIG. 9A shows the distribution of average values of delay for the case where the concentration of each nucleotide species in solution is identical (on X axis—the delay number, on Y axis—the average delay value in units of time, calculated for the current number of delay).
Figure 9B:
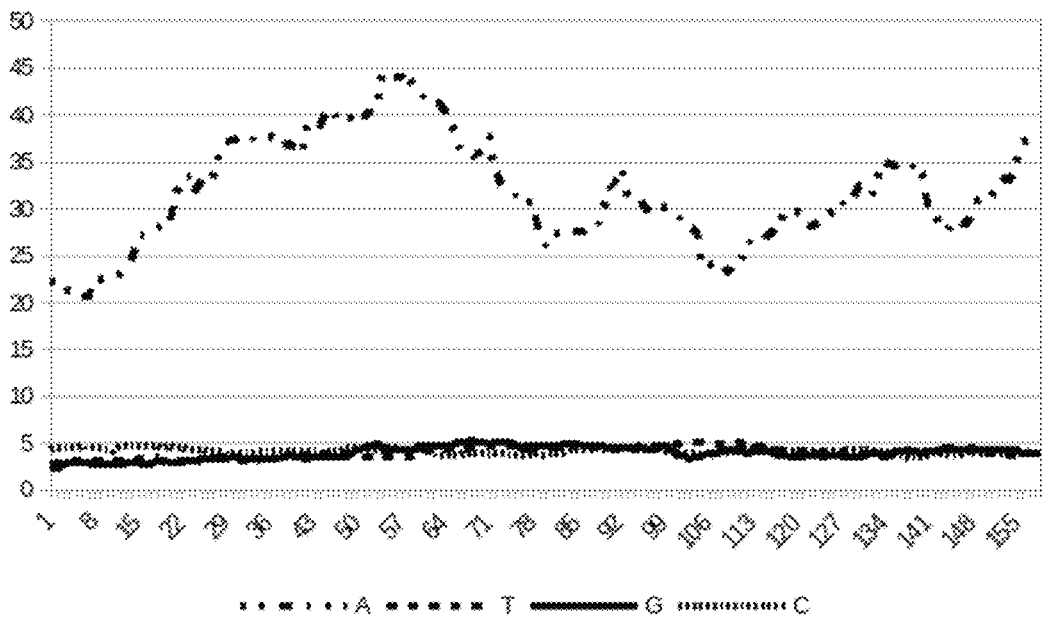
FIG. 9B shows the distribution of average values of time delay for each kind of nucleotides, provided 10-fold decrease of nucleotide concentration of one type, —nucleotide species A in the reaction mixture (in X-axis—the delay number, on Y axis—the average delay value in units of time, calculated for the current number of delay).

Time delay is the time when the polymerase waits for the complementary nucleotide to arrive at the Assembly site in order to insert it into the polymerized DNA fragment. The distribution of time delays for each type of nucleotide is presented in FIG. 7; on X-axis indicated the amount of delay in units of time, Y axis—the number of time delays defined on the x-axis duration obtained by numerical experiments. As seen from the figure: the majority of delays equal to zero for the case where the concentration of each type of nucleotide in the reaction mixture of the same. If the concentration of one type of nucleotide in the reaction mixture will be reduced against the normal concentration nucleotides other species, numerical experiments show distribution represented in FIG. 8. From of this distribution can be seen that reducing the concentration of A type nucleotide reduces the number of short time delays for these nucleotides and increases the amount of short time delays for other types of nucleotides. The average delay time for the 4 nucleotide types during DNA polymerization reaction is shown in FIG. 9A. The average delay time is calculated using a sliding window of 50 cycles cellular automaton. On Y axis in the graphs shows the calculated average value of the delay in arbitrary units for the current delay number. FIG. 9A shows the results of the calculation when the concentration of nucleotides of all 4 species is the same in the reaction mixture. FIG. 9B shows the results of calculations, when the concentration of A type nucleotide 10 times less than the normal concentration nucleotides other 3 species; this graph shows that the delay for nucleotides depleted kind on average, longer than for other types of nucleotides. The calculations were performed for an oligonucleotide whose nucleotide sequence is presented below.

FIG. 9B shows that a certain threshold value, for example, the number 15, will unambiguously separate the time delays for the depleted type of nucleotides and for the not depleted type of nucleotides. The effect presented in FIGS. 9A and 9B shows average time of delays in each position of the nucleotide sequence of DNA after K series of independent experiments. By averaging experimental data for a reaction mixture that has been depleted in nucleotides of type A, it is possible to accurately determine the position of nucleotides of type A in the nucleotide sequence of the DNA fragment to which the nucleotides have been attached. By turns, depleting the nucleotides of other species, the positions of the nucleotides of these species are determined in the nucleotide sequence of the same DNA fragment in a similar way.

Sequence Listing applied in numerical experiments:

```
SEQ ID NO: 1 - ultramer-oligonucleotide used for
obtaining a single-stranded circular DNA (IDT
Inc., USA)
5'-/Phos/CATGTAGTGTACGATCCGACTTTACTTCAGCGTCCGTCGCA

AGGAAATCTAGCCGTCGAGGCGCTATTGGAGACTAGCTGACACCACCGTG

CCAACTGAAGAAGGGCAGCTATGCGTCCTGTTGACAATTATCTTTAACTC

GTTTATTGGTTAGTCAAGGTCCAAGCCTGCTATGGA-3'

SEQ ID NO: 2 - Direct PCR primer
5'-/Phos/CATGTAGTGTACGATCCGACTT-3'

SEQ ID NO: 3 - Reverse PCR primer
5'-TCCATAGCAGGCTTGGACCT-3'

SEQ ID NO: 4 - Oligonucleotide-"bridge"
5'-GTACACTACATGTCCATAGCAGGCTTG-3'
```

Example 9. Numerical Experiment of DNA Reconstruction

The sequencing algorithm is based on the diffusion mechanism of nucleotide movement to the assembly site, where the polymerase integrates complementary nucleotides into the polymerized fragment of the nucleic acid, and on the hypothesis that in average the ratio of time intervals before the integration of a nucleotide with reduced concentration to the time intervals before the integration of a nucleotide with a normal concentration will be as big as the difference in their concentrations. To test this hypothesis, a mathematical model was developed and numerical experiments were conducted, the results of which confirmed the accuracy of the hypothesis.

Numerical experiments on the nucleotide DNA sequence recovery were performed on the basis of two software modules: the module from the Example 8, which was used to generate time delays before the integration of each nucleotide during the polymerization reaction of the DNA fragment, and the module that recovers the original nucleotide sequence of the DNA fragment from these time delays values.

The module for recovering of the original nucleotide DNA sequence statistically processes the results from several independent experiments. Tables 1, 2, 3 show statistically processed results from 2,000 experiments on the calculation of the accuracy of the looped nucleotide sequences of DNA fragments in the form of a "dumbbell" recovery: for the DNA fragments matrix of length 1,000, 2,000, 3,000 and 5,000 nucleotides linked by the "bridge" of 25 nucleotides on each side of the "dumbbell".

The proposed sequencing algorithm does not require labels for nucleotides, since useful information is the time interval before each nucleotide is integrated.

The sequencing algorithm is unique because unlike most well-known sequencing algorithms, the procedure for generating a useful signal and the procedure for its identification i.e. determining the type of nucleotides which this signal corresponds to. Due to this property, the algorithm allows you to choose the accuracy of the sequencing result that is required. In this case, the more time is given for the sequencing procedure, the more accurate result can be obtained. Depending on the problem being solved, at the sample preparation stage can be formed conditions that will provide the desired sequencing result.

The characteristics of the molecules involved in the sequencing procedure impose their limitations on the parameters of the sequencing results, and the estimates can be given provided that the Phi29 polymerase, that has a processivity of 80,000 nucleotides, is used.

The calculations results for the 1:10 ratio of concentration of one nucleotide type to three other types showed that the accuracy of DNA fragment sequencing is 86.9138% in average for fragments of 2,000 nucleotides, and this accuracy is almost independent of the fragment length, since the result of the integration of each nucleotide does not depend on the results of integration of other nucleotides in the same polymerizable nucleic acid fragment. Table 1 with the results of calculations at a ratio of 1:10 concentration of one type of nucleotide to three others with statistical processing of 2,000 numerical experiments for nucleic acid fragments of 2,000 nucleotides, organized in the form of a "dumbbell", is presented below:

TABLE 1

| Number of runs | Number of fragments not fully restored | Min. number | Max number | Average number | Recovery accuracy |
|---|---|---|---|---|---|
| 1 | 2000 | 209 | 317 | 261 | 86.9138 |
| 2 | 2000 | 32 | 76 | 52 | 97.3516 |
| 3 | 2000 | 2 | 22 | 10 | 99.4556 |
| 4 | 1786 | 0 | 8 | 2 | 99.8873 |
| 5 | 637 | 0 | 3 | 0 | 99.981 |
| 6 | 101 | 0 | 2 | 0 | 99.99745 |
| 7 | 10 | 0 | 1 | 0 | 99.99975 |
| 8 | 0 | 0 | 0 | 0 | 100 |

Table 2 with the results of calculations for the 1:10 ratio of the reduced concentration of one type of nucleotide to three others, with statistical processing of 2,000 numerical experiments for nucleic acid fragments of 5,000 nucleotides organized in the form of a "dumbbell", is presented below:

TABLE 2

| Number of runs | Number of fragments not fully restored | Min. number | Max number | Average number | Recovery accuracy |
|---|---|---|---|---|---|
| 1 | 2000 | 581 | 748 | 656 | 86.87644 |
| 2 | 2000 | 94 | 168 | 133 | 97.32191 |
| 3 | 2000 | 12 | 47 | 27 | 99.44684 |
| 4 | 1995 | 0 | 18 | 5 | 99.88082 |
| 5 | 1434 | 0 | 6 | 1 | 99.97508 |
| 6 | 342 | 0 | 3 | 0 | 99.99629 |
| 7 | 44 | 0 | 1 | 0 | 99.99956 |
| 8 | 6 | 0 | 1 | 0 | 99.99994 |
| 9 | 0 | 0 | 0 | 0 | 100 |

The first column of Tables 1 and 2 shows the number of runs, i.e. complete polymerization cycles of the DNA fragment; the second column shows the number of experiments where the nucleotide sequence was not restored with 100% accuracy. The third, fourth, and fifth columns show respectively, minimum, maximum, and average numbers of nucleotides, that were not recovered in the sequenced DNA fragments. The sixth column shows the averaged over 2,000 experiments accuracy of the sequenced DNA fragments recovery.

It is clear that if you set the ratio of concentrations, for example, 1:20, then accuracy increases after one reading, i.e. we can change time for accuracy. The corresponding calculation results with statistical processing of 2,000 numerical experiments for nucleic acid fragments of 2,000 nucleotides organized in the form of a "dumbbell" are shown in Table 3 below:

TABLE 3

| | The multiplicity of reduction of one type of nucleotides against the other three | | | |
|---|---|---|---|---|
| | 10 times | 20 times | 50 times | 100 times |
| Accuracy after first run | 86.9138 | 94.7988 | 98.7043 | 99.5886 |
| Number of runs for 99% accuracy | 3 | 2 | 2 | 1 |
| Number of runs for 99.9% accuracy | 5 | 3 | 2 | 2 |
| Number of runs for 99.99% accuracy | 6 | 4 | 3 | 2 |
| Number of runs for 99.9999% accuracy | 8 | 5 | 4 | 3 |
| The duration of one run in nominal units | 40800 | 71019 | 162080 | 313856 |

The length of the sequenced fragment depends on the polymerase processability and the chosen sequencing device: one-matrix or four-matrix.

In the first case, there is one microcircuit matrix with cells. Each cell contains a "polymerase-DNA fragment" complex immobilized on sensor. The four reaction solutions are feeding onto the microcircuit surface alternately, within each of them the concentration of only one type of nucleotide is lowered, and each time a different type. In this case, because the polymerase works in the same cell, but with 4 different reaction solutions, —it can integrate only 20,000 nucleotides in one reaction solution; depending on the desired accuracy of DNA fragment sequencing, you can select, for example, a DNA fragment with the length of 5,000 nucleotides, perform 4 polymerization cycles and obtain an accuracy of 99.88%; or you can take a fragment of 3,000 nucleotides and get an accuracy of 99.997%, etc.

In the second case, the above reaction solutions are each fed on the surface of their own microcircuit in which cells complexes with the clones of the original DNA fragments are immobilized on the sensors; in this case one polymerase works in the same cell with only one reaction solution and can integrate 80,000 nucleotides. In this case DNA fragments with the length of 10,000 or more nucleotides can be sequenced, again depending on the desired accuracy.

LITERATURE USED

1. Trajkovic L. J. and Willson A. N., Jr. Complementary two-transistor-circuits and negative differential Resistance//IEEE Trans. Circuits Syst., vol. 37, pp. 1258-1266, October 1990.
2. Kramers H. A. Brownian motion in a field of force and the diffusion model of chemical reactions. Physica v. 7(4), p. 284-304. —1940.
3. Renzi R., Sutera A., Vulpiani A. The Mechanism of Stochastic Resonance. Journal of Physics A: Mathematical and General, 1981, 14: 453-457.
4. Fauve S., Heslot F. Stochastic resonance in a bistable system. Physics Lett. A 97 (1-2).-1983. p. 5-7,
5. Gammaitoni L. et al. Stochastic resonance. Reviews of Modern Physics, Vol. 70, No. 1, January 1998. p. 223-287.

We claim:

1. A method for determining a nucleotide sequence of a nucleic acid molecule comprising at least the following steps:
   (a) obtaining a sample prepared from the nucleic acid molecule without amplification of said molecule by polymerase chain reaction, wherein the sample constitutes a plurality of circularized nucleic acid fragments;
   (b) immobilizing on a solid surface complexes consisting of at least said circularized nucleic acid fragments obtained from the nucleic acid molecule and a polymerase, having an affinity for nucleic acids, wherein each individual complex is immobilized in a different sensor cell, and all sensor cells constitute an array of sensor cells; each sensor cell contains a nanoscale charge-sensitive sensor configured to detect release of a hydrogen ion during incorporation by the polymerase of a nucleotide into a growing nucleic acid strand; the solid surface is a sensor cell surface, and said immobilization retains functionality of the polymerase and ensures that the polymerase is retained in the close proximity to the sensor within the entire process of determining the nucleotide sequence;
   (c) providing conditions for a functional activity of said polymerase, consisting in catalyzing an addition of nucleotides to the growing nucleic acid strand, wherein providing conditions for the functional activity of the polymerase include:
      addition to a sensor cell of a mixture of two or more types of unlabeled deoxyribonucleotides selected from the group consisting of deoxyadenosine triphosphate, deoxyguanosine triphosphate, deoxycytidine triphosphate, and deoxytimidine triphosphate, or
      addition to the sensor cell of a mixture of two or more types of unlabeled ribonucleotides selected from the group consisting of adenosine triphosphate, guanosine triphosphate, cytidine triphosphate, and uridine triphosphate,
   wherein in said mixture a nucleotide of one type is present in a much lower concentration than the other types of nucleotides;
   (d) registering by the sensor a release of a hydrogen ion that occurs as a result of separation of one pair of charges during an incorporation by the polymerase of a nucleotide into the growing nucleic acid strand, and determining time intervals between each successive registered event of hydrogen ion release, wherein a site of the incorporation is located within an electrical field formed by an electrical double layer on the sensor cell surface or within an electrical field formed as a superposition of the electrical double layer field and a potential applied to an electrode of the sensor;
   (e) repeating steps (c) and (d) at least one more time, wherein the type of the nucleotide present in the added nucleotide mixture in much smaller concentration as compared with the other types, changes at each repetition, and different nucleotide mixtures are added sequentially to the same the sensor cell;
   (f) determining the nucleotide sequence of said nucleic acid molecule based on an analysis of the time intervals between each event of hydrogen ion releases registered at steps (d) and (e), where each hydrogen ion release occurred as a result of incorporation by the polymerase of said unlabeled nucleotides into the growing nucleic acid strand.

2. A method according to claim 1, wherein
   circularized nucleic acid fragments defined under (a) have at least one single-stranded portion;
   complexes defined under (b) and immobilized on the solid surface, further include a sequencing primer having a nucleotide sequence complementary to said single-stranded region; and
   conditions for the functional activity of the polymerase in the steps (c) and (e) further include conditions ensuring a duplex formation between the sequencing primer and the complementary region of said circularized single-stranded nucleic acid fragment.

3. The method of claim 2, wherein the nucleic acid is DNA; the polymerase having an affinity for nucleic acids is a DNA polymerase; and the nucleotides added in step (c) and (d) are deoxyadenosine triphosphate, deoxyguanosine triphosphate, deoxycytidine triphosphate, and deoxytimidine triphosphate.

4. The method of claim 3, wherein the DNA polymerase has a strand-displacement activity.

5. The method of claim 1, wherein the polymerase having an affinity for nucleic acids is an RNA polymerase; and nucleotides added in step (c) and (d), are adenosine triphosphate, guanosine triphosphate, cytidine triphosphate, and uridine triphosphate.

6. The method of claim 3, wherein at steps (c) and (d) deoxynucleotide triphosphates of four different types, namely deoxyadenosine triphosphate, deoxyguanosine triphosphate, deoxycytidine triphosphate, and deoxytimidine triphosphate, which constitutes together a mixture of deoxynucleotide triphosphates, are added to the surface of the sensor.

7. The method of claim 6, wherein at the steps (c) and (d) there is a provision of four different conditions for the functional activity of the polymerase, namely, an addition of four different deoxynucleoside triphosphates mixtures to the sensor surface.

8. The method of claim 7, wherein each of the four different conditions for the functional activity of the polymerase is present continuously for a time interval sufficient for synthesis of at least one copy of a circularized DNA fragment.

9. A method according to claim 8, wherein each of the four different conditions for the functional activity of the polymerase is present continuously for a time interval sufficient for synthesis of at least five copies of a circularized DNA fragment.

10. The method of claim 9, wherein the analysis of the time intervals used to determine the nucleotide sequence of said nucleic acid molecule comprises at least three steps:
1) converting sequences of time intervals between each registered event of released hydrogen ion that occurred as a result of incorporation of unlabeled nucleotides into the growing nucleic acid strand by the polymerase, into sequences of logical zeros and ones, wherein in each such sequence the logical ones denote events of incorporation of the type of nucleotides, the concentration of which was known and lowered in the reaction mixture corresponding to this sequence, and the logical zeros denote types of nucleotides whose concentration was normal in the same reaction mixture;
2) forming nucleotide sequences of the nucleic acid fragments from the four sequences of logical zeros and ones obtained after the first step of data conversion for each nucleic acid fragment;
3) converting the nucleotide sequences of nucleic acid fragments into the nucleotide sequence of said nucleic acid molecule.

11. An apparatus for determining a nucleotide sequence of a nucleic acid molecule by an implementation of the method according to claim 1, comprising:
a) at least one chip with an array of sensor cells and an analog-to-digital circuit;
b) a microfluidic device for providing a supply of working solutions to the sensor cells of the chip;
c) a data processing and display device to control operating modes of the microfluidic device and the chip to convert data of output sequences from the array of cells into the nucleotide sequence of said nucleic acid molecule;
d) an electrode located on a lid of the chip that forms an electric field with a strength enough to allow registration of a released hydrogen ion;
wherein the apparatus is characterized by the following:
i) each cell of the array comprises:
a sensor with a surface that comprises no more than a single polymerase complex immobilized on the surface, the complex comprising a polymerizable DNA fragment and a polymerase having an affinity for nucleic acids, the sensor being capable of registering an event of a single hydrogen ion release due to charge separation in an aqueous solution occurring as a result of an incorporation of a nucleotide into the polymerizable DNA fragment of the complex, the sensor additionally being capable of generating signals corresponding to registered events of released hydrogen ions, wherein a site of the incorporation is located within the electric field formed as a superposition of an electrical double layer field on the sensor surface and an electric field resulting from a potential applied to the electrode;
an analog-to-digital cell circuit to generate an output sequence of discrete time intervals corresponding to sensor signals; and
ii) the analog-to-digital circuit of the chip with the array of sensor cells comprises:
circuitry forming currents, voltages and clock frequencies required for operation of the analog-digital circuits of the array of cells;
circuitry for transmitting output sequences from the array of cells to the data processing and display device;
circuitry for decoding data received from the data processing and display device.

12. The apparatus of claim 11, which further includes a means of maintaining working temperature of a solution over the surface of the chip array, which is controlled by the data processing and display device.

13. The apparatus of claim 11 wherein the sensor is designed as a nanowire field effect transistor, a single-electron transistor, a diode, a field effect transistor, or a semiconductor structure representing an electronic circuit with an S-shaped or N-shaped voltage-current or transfer characteristic.

14. The apparatus of claim 13, which includes exactly one chip with the array of sensor cells.

15. The apparatus of claim 14, wherein the data processing and display device converts the data output sequences from the cells of chip array into the nucleotide sequence of said nucleic acid molecule in three successive steps.

16. The apparatus of claim 11, which includes four chips with the array of sensor cells.

17. The apparatus of claim 16, wherein the data processing and display device converts the data into the nucleotide sequence of the nucleic acid molecule in four successive stages.

* * * * *